(12) United States Patent
Crooke et al.

(10) Patent No.: US 7,888,324 B2
(45) Date of Patent: Feb. 15, 2011

(54) ANTISENSE MODULATION OF APOLIPOPROTEIN B EXPRESSION

(75) Inventors: Rosanne M. Crooke, Carlsbad, CA (US); Mark J. Graham, San Clemente, CA (US)

(73) Assignee: Genzyme Corporation, Cambridge, MA (US)

( * ) Notice: Subject to any disclaimer, the term of this patent is extended or adjusted under 35 U.S.C. 154(b) by 0 days.

(21) Appl. No.: 09/920,033

(22) Filed: Aug. 1, 2001

(65) Prior Publication Data

US 2003/0087853 A1 May 8, 2003

(51) Int. Cl.
*A61K 31/70* (2006.01)
*C07H 21/04* (2006.01)

(52) U.S. Cl. ............... 514/44; 536/24.3; 536/24.31; 536/24.5

(58) Field of Classification Search .......... 536/23.1, 536/24.3, 24.33, 24.5; 435/6, 325, 375, 455, 435/458; 514/44
See application file for complete search history.

(56) References Cited

U.S. PATENT DOCUMENTS

| | | | |
|---|---|---|---|
| 5,220,006 A | 6/1993 | Ross et al. | |
| 5,434,058 A | 7/1995 | Davidson et al. | |
| 5,618,674 A * | 4/1997 | Sanchez-Pescador et al. | 435/6 |
| 5,656,612 A * | 8/1997 | Monia | 514/44 |
| 5,712,257 A | 1/1998 | Carter | |
| 5,786,206 A | 7/1998 | Smith et al. | |
| 5,801,154 A | 9/1998 | Baracchini et al. | |
| 5,945,290 A * | 8/1999 | Cowsert | 435/6 |
| 5,998,148 A | 12/1999 | Bennett et al. | |
| 6,033,910 A | 3/2000 | Monia et al. | |
| 6,096,516 A | 8/2000 | Kwak et al. | |
| 6,156,315 A | 12/2000 | Goldberg et al. | |
| 6,172,216 B1 * | 1/2001 | Bennett et al. | 536/24.5 |
| 6,184,212 B1 | 2/2001 | Miraglia et al. | |
| 6,512,161 B1 * | 1/2003 | Rouy et al. | 800/3 |
| 6,534,277 B1 * | 3/2003 | Hancock et al. | 435/6 |
| 6,949,367 B1 | 9/2005 | Dempcy et al. | |
| 2003/0087853 A1 | 5/2003 | Crooke et al. | |
| 2003/0215943 A1 | 11/2003 | Crooke et al. | |
| 2004/0214325 A1 | 10/2004 | Crooke et al. | |
| 2004/0241651 A1 | 12/2004 | Olek et al. | |
| 2005/0009088 A1 | 1/2005 | Crooke et al. | |
| 2005/0287558 A1 | 12/2005 | Crooke et al. | |
| 2006/0009410 A1 | 1/2006 | Crooke et al. | |
| 2006/0035858 A1 | 2/2006 | Geary et al. | |

FOREIGN PATENT DOCUMENTS

| | | |
|---|---|---|
| EP | 0332435 | 9/1989 |
| EP | 0530794 | 3/1993 |
| EP | 0 911 344 A1 | 4/1999 |
| WO | WO 97/35538 A2 | 10/1997 |
| WO | WO 98/20166 | 5/1998 |
| WO | WO 98/32846 A3 | 7/1998 |
| WO | WO 98/36641 A1 | 8/1998 |
| WO | WO 99/18237 | 4/1999 |
| WO | WO 99/18986 | 4/1999 |
| WO | WO 99/35241 | 7/1999 |
| WO | WO0000504 A1 * | 1/2000 |
| WO | WO 00/56916 | 9/2000 |
| WO | WO 00/56920 | 9/2000 |
| WO | WO 01/12789 A2 | 2/2001 |
| WO | WO 01/30354 A1 | 3/2001 |
| WO | WO 01/30395 A1 | 5/2001 |
| WO | WO 01/52902 A1 | 7/2001 |
| WO | WO 01/77384 A3 | 10/2001 |
| WO | WO 02/26768 A3 | 4/2002 |
| WO | WO 03/011887 A3 | 2/2003 |
| WO | WO 03/074723 A3 | 9/2003 |
| WO | WO 03/097662 A1 | 11/2003 |
| WO | WO 2004/044181 A3 | 5/2004 |
| WO | WO 2005/049621 A1 | 6/2005 |

OTHER PUBLICATIONS

Tang et al. The inhibitory effect of antisnse oligonucleotides on apoplipoprotein B expression in liver cells of rat. Zhongguo Dongmai Yinghua ZaZhi Bianjibu (Chinese Journal), (1999), vol. 7, No. 4, pp. 315-318.*
Branch, TIBS, vol. 23, 1998, pp. 45-50.*
Agrawal et al. Antisense therapeutics: is it as simple as complementary base recognition? Molecular Medicine Today, Feb. 2000, vol. 6, pp. 72-81.*
John Rossi, Introductory Remarks on the General Application of Antisense RNAs and RIbozymes. Methods: A Companion to Methods in Enzymology. vol. 5, pp. 1-5, 1993.*
Tang et al. The Inhibition of Antisense Oligodeoxynucleotides on the Expression of Apolipoprotein B in Rat Liver Cells. Chinese Journa of Arteriosclerosis. vol. 7, No. 4, 1997. Translation.*
Tang et al. see IDS of Oct. 27, 2003.*
GenBank Accession No. NM_000384 , Oct. 31, 2000, (Huang et al.).*
Borén et al., "A Simple and Efficient Method for Making Site-directed Mutants, Deletions, and Fusions of Large DNA Such as P1 and BAC Clones", *Genome Research* 1996 1123-1130.
Davidson et al., "Apolipoprotein B:mRNA Editing, Lipoprotein Assembly, and Presecretory Degradation", *Annu. Rev. Nutr.* 2000 20:169-193.
Farese et al., "Knockout of the mouse apolipoprotein B gene results in embryonic lethality in homozygotes and protection against diet-induced hypercholesterolemia in heterozygotes", *Proc. Natl. Acad. Sci. USA* 1995 92:1774-1778.
Deeb et al., "Chromosomal localization of the human apolipoprotein B gene and detection of homologous RNA in monkey intestine", *Proc. Natl. Acad. Sci. USA* 1986 83:419-422.

(Continued)

*Primary Examiner*—Janet L Epps-Smith
(74) *Attorney, Agent, or Firm*—Jones Day

(57) ABSTRACT

Antisense compounds, compositions and methods are provided for modulating the expression of apolipoprotein B. The compositions comprise antisense compounds, particularly antisense oligonucleotides, targeted to nucleic acids encoding apolipoprotein B. Methods of using these compounds for modulation of apolipoprotein B expression and for treatment of diseases associated with expression of apolipoprotein B are provided.

20 Claims, No Drawings

OTHER PUBLICATIONS

Hajjar et al., "The Role of Lipoprotein(a) In Atherogenesis and Thrombosis", *Annu. Rev. Med.* 1996 47:423-442.

Innerarity et al., "Familial defective apolipoprotein B-00:Low density lipoproteins with abnormal receptor binding", *Proc. Natl. Acad. Sci. USA* 1987 84:6919-6923.

Katan et al., "Characteristics of Human Hypo- and Hyperresponders to Dietary Cholesterol", *American Journal of Epidemiology* 1987 125 (3):387-399.

Kim et al., "Genetically modified mice for the study of apolipoprotein B", *Journal of Lipid Research* 1998 39:703-723.

Law et al., "Human apolipoprotein B-100:Cloning, analysis of liver mRNA, and assignment of the gene to chromosome 2", *Proc. Natl. Acad. Sci. USA* 1985 82:8340-8344.

McCormick et al., "Transgenic Mice Expressing Human ApoB95 and ApoB97", *The Journal of Biological Chemistry* 1997 272(38):23616-23622.

Nishina et al., "Synthetic low and high fat diets for the study of atherosclerosis in the mouse", *Journal of Lipid Research* 1990 31:859-869.

Nowak-Göttl et al., "Lipoprotein (a):Its Role in Childhood Thromboembolism", *Pediatrics* 1997 99(6):1-3.

Sandkamp et al., "Lipoprotein(a) Is an Independent Risk Factor for Myocardial Infarction at a Young Age", *Clin. Chem.* 1990 36/1:20-23.

Seed et al., "Relation of Serum Lipoprotein(a) Concentration and Apolipoprotein(a) Phenotype to Coronary Heart Disease in Patients with Familial Hypercholesterolemia", *The New England Journal of Medicine* 1990 1494-1498.

Véniant et al., "Susceptibility to Atherosclerosis in Mice Expressing Exclusively Apolipoprotein B48 or Apolipoprotein B100", *J. Clin. Invest.* 1997 100(1):180-188.

Vessby et al., "Diverging Effects of Cholestyramine on Apolipoprotein B and Lipoprotein Lp(a)", *Atherosclerosis* 1982 44:61-71.

Branch, A.D., "A good antisense molecule is hard to find," *TiBS* 23: 45-50 (1998).

Tang et al., "The Inhibition of Antisense Oligodeoxynucleotides on the Expression of Apolipoprotein B in Rat Liver Cells," *Chinese Journal of Arteriosclerosis* 7(4) (1999) (English translation).

Tanaka et al., "Regulation of Apolipoprotein B Production and Secretion in response to the Change of Intracellular Cholesteryl Ester Contents in Rabbit Hepatocytes," *The Journal of Biological Chemistry* 268(17): 12713-12718 (1993).

U.S. Appl. No. 60/159,462, Eggerman et al.

Parrish et al., Molecular Cell 2000, vol. 6, pp. 1077-1087 (2000).

Hammond et al., Post-transcriptional gene silencing by double-stranded RNA, Nature Genetics 2001, vol. 2: 110-119 (Feb. 2001).

Patil et al., DNA-based therapeutics and DNA delivery systems: A comprehensive review, 2005. The AAPS Journal, vol. 7, pp. E61-E77.

De Mesmaeker, et al. 1995. *Backbone Modifications in Oligonucleotides and Peptide Nucleic Acid Systems.* Current Opinion in Structural Chemistry, 5: 343-355.

Supplementary Partial European Search Report from PCT/US0224247 dated Jul. 27, 2006.

EMBL Accession No. A23827, Apr. 2, 1995.
EMBL Accession No. A13429, Oct. 5, 1994.
EMBL Accession No. A97152, Jan. 26, 2000.
GENESEQ Accession No. AAA07969, Jan. 29, 2001.
EMBL Accession No. AR 152836, Aug. 9, 2001.
EMBL Accession No. 113154, Aug. 2, 1995.
GENESEQ Accession No. AAA28208, Jan. 29, 2001.
GENESEQ Accession No. AAV39607, Sep. 28, 1998.

Crooke, S. T., "Basic Principles of Antisense Therapeutics," *Antisense Research and Application* (1998) Springer-Verlag Press, Berlin, pp. 1-50.

EMBL Accession No. L27195, Jan. 6, 1994.

Graham, M. J. et al., "Inhibition of ApoB-100 as a Therapeutic Strategy for the Treatment of Hyperlipidermias," *AHA Abstract* (2002) ID: 548.

Huang, L.-S. et al., "Hypobetalipoproteinemia due to an apolipoprotein B gene exon 21 deletion derived by Alu-Alu recombination,"*J. Biol. Chem.* (1989) 264(19):11394-11400.

Jen, K.-Y. et al., "Suppression of Gene Expression by Targeted Disruption of Messenger RNA: Available Options and Current Strategies," *Stem Cells* (2000) 18:307-319.

Latorra, D. et al., "Enhanced Allele-Specific PCR Discrimination in SNP Genotyping Using 3' Locked Nucleic Acid (LNA) Primers," *Hum. Mutat.* (2003) 22:79-85.

Ma, D. D. F. et al., "Synthetic oligonucleotides as therapeutics: the coming of age," *Biotechnology Annual Review* (2000) 5:155-196.

Petersen, M. et al., "Locked Nucleic Acid (LNA) Recognition of RNA: NMR Solution Structures of LNA:RNA Hybrids," *J. Am. Chem. Soc.* (2002) 124(21):5974-5982.

Simeonov, A. et al., "Single nucleotide polymorphism genotyping using short, fluorescently labeled locked nucleic acid (LNA) probes and fluorescence polarization detection," *Nucleic Acids. Res.* (2002) 30(17):e91.

Skrapari, L. et al., "Glibenclamide improves postprandial hypertriglyceridaemia in Type 2 diabetic patients by reducing chylomicrons but not the very low-density lipoprotein subfraction levels," *Diabetic Med.* (2001) 18:781-785.

Chin, A., "On the Preparation and Utilization of Isolated and Purified Oligonucleotides" Document purportedly located on a CD-ROM and contributed to the public collection of the Katherine R. Everett Law Library of the University of North Carolina on Mar. 14, 2002.

Eggerman et al., "Use of Oligonucleotides to Target Nucleic Acid Sequences Encoding Apolipoprotein B to Decrease Serum Apolipoprotein B and Cholesterol Levels" *Federal Register*, 2000, vol. 65:110.

Bennett et al., "Antisense Oligonucleotides as a Tool for Gene Functionalization and Target Validation," *Biochimica et Biophysica Acta*, 1999, vol. 1489:18-30.

EMBL Accession No. L24258, Sep. 18, 1993.

James, W., "Towards gene-inhibition therapy; a review of progress and prospects in the field of antiviral antisense nucleic acids and ribozymes," *Antiviral Chemistry and Chemotherapy*, Apr. 1991, vol. 2, No. 4:191-214.

Milner et al., "Selecting effective antisense reagents on combinatorial oligonucleotide arrays," *Nature Biotechnology*, Jun. 1997, vol. 15:537-541.

NCBI Search Results, (ISPH-0592) dated Oct. 30, 2007, *Mamm. Genom*, 1995, vol. 6 (3):192-195.

New England Biolabs, 1998/1999 Catalog, pp. 121 and 284.

Rojanasakul, Y, "Antisense Oligonucleotide Therapeutics: Drug Delivery and Targeting," *Advanced Drug Delivery Reviews*, 1996, vol. 18, pp. 115-131, XP002913878.

Rubies-Prat et al., "Low-density lipoprotein particle size, triglyceride-rich lipoproteins, and glucose tolerance in non-diabetic men with essential hypertension" *Clinical and Experimental Hypertension*, 2001, vol. 23:489-500.

Smith et al., "Rational selection fo antisense oligonucleotide sequences," *European Journal of Pharmaceutical Sciences*, 2000, vol. 11, No. 3, 191-198, XP002372482.

Yu et al., "Pharmacokinetics and Pharmacodynamics of an Antisense Phosphorothioate Oligonucleotide Targeting Fas mRNA in Mice," *J. Pharmacol. Exp. Ther.*, 2001, vol. 296-388-395.

Advisory Action for U.S. Appl. No. 10/712,795 dated Apr. 28, 2008.
Final Rejection Office Action for U.S. Appl. No. 10/712,795 dated Apr. 9, 2007.
Final Rejection Office Action for U.S. Appl. No. 10/712,795 dated Jan. 8, 2008.
Office Action for U.S. Appl. No. 10/712,795 dated Apr. 14, 2006.
Office Action for U.S. Appl. No. 10/712,795 dated Oct. 10, 2006.
Office Action for U.S. Appl. No. 10/712,795 dated Jul. 26, 2007.
Advisory Action for U.S. Appl. No. 10/920,612 dated Oct. 16, 2007.
Advisory Action for U.S. Appl. No. 10/920,612 dated Feb. 26, 2009.
Final Rejection Office Action for U.S. Appl. No. 10/920,612 dated Mar. 28, 2007.
Final Rejection Office Action for U.S. Appl. No. 10/920,612 dated Aug. 7, 2008.
Office Action for U.S. Appl. No. 10/920,612 dated Aug. 8, 2006.
Office Action for U.S. Appl. No. 10/920,612 dated Dec. 12, 2007.

Office Action for U.S. Appl. No. 11/123,656 dated Jun. 13, 2007.
Office Action for U.S. Appl. No. 11/123,656 dated Dec. 13, 2007.
Office Action for U.S. Appl. No. 11/123,656 dated Dec. 3, 2008.
Office Action for U.S. Appl. No. 11/123,656 dated Sep. 9, 2009.
Advisory Action for U.S. Appl. No. 11/200,710 dated Sep. 13, 2007.
Final Rejection Office Action for U.S. Appl. No. 11/200,710 dated May 15, 2007.
Final Rejection Office Action for U.S. Appl. No. 11/200,710 dated Jan. 13, 2009.
Office Action for U.S. Appl. No. 11/200,710 dated Sep. 28, 2006.
Office Action for U.S. Appl. No. 11/200,710 dated May 21, 2008.
Non-final Office Action for U.S. Appl. No. 11/200,710 dated Apr. 15, 2010.
Non-final Office Action for U.S. Appl. No. 11/573,537 dated Jun. 18, 2010.
Final Rejection Office Action for U.S. Appl. No. 10/147,196 dated Mar. 24, 2004.
Final Rejection Office Action for U.S. Appl. No. 10/147,196 dated Feb. 1, 2005.
Final Rejection Office Action for U.S. Appl. No. 10/147,196 dated May 17, 2006.
Office Action for U.S. Appl. No. 10/147,196 dated Jul. 11, 2003.
Office Action for U.S. Appl. No. 10/147,196 dated Aug. 12, 2004.
Office Action for U.S. Appl. No. 10/147,196 dated Aug. 17, 2005.
Office Action for U.S. Appl. No. 10/147,196 dated Jan. 25, 2007.
Final Rejection Office Action for U.S. Appl. No. 11/124,020 dated Jul. 30, 2010.
Advisory Action for U.S. Appl. No. 11/124,020 dated Aug. 11, 2009.
Final Rejection Office Action for U.S. Appl. No. 11/124,020 dated Jan. 26, 2009.
Office Action for U.S. Appl. No. 11/124,020 dated Jan. 14, 2008.
Office Action for U.S. Appl. No. 11/124.020 dated Dec. 2, 2009.
Office Action for U.S. Appl. No. 11/969,096 dated Oct. 28, 2009.
Final Office Action for U.S. Appl. No. 11/969,096 dated Jul. 15, 2010.
ISA, International Search Report dated Aug. 31, 2004 for application No. PCT/US03/36411.
EPO, Supplementary Partial European Search Report for Application No. 03789763.4 dated Jul. 26, 2006.
EPO, Supplementary European Search Report for Application No. 03789763.4 dated Jul. 26, 2006.
ISA, International Search Report dated Apr. 10, 2006 for Application No. PCT/US05/028342.
ISA, International Search Report for Application PCT/US00/29223 dated Dec. 26, 2000.
EPO, Supplementary Partial European Search Report for application No. 027761201.9 dated Jul. 3, 2006.
EPO, Supplementary European Search Report for 027761201.9 dated Jul. 3, 2006.
EPO, European Search Report for application No. 09015376.8 dated Feb. 8, 2010.
ISA, International Search Report dated Oct. 22, 2003 for Application No. PCT/US03/15493.
ISA, International Search Report for dated Jul. 28, 2008 Application PCT/US08/058072.
ISA, International Search Report dated Apr. 21, 2008 for Application No. PCT/US07/68401.
ISA, Communication Relating to the Results of the Partial International Search PCT/US07/68401 dated Jan. 30, 2008.
ISA, International Search Report dated Mar. 13, 2008 for Application PCT/US07/68403.
ISA, International Search Report dated Mar. 13, 2008 for Application PCT/US07/68404.
ISA, International Search Report dated Apr. 24, 2008 for Application PCT/US07/68410.
ISA, International Search Report dated Apr. 24, 2008 for Application PCT/US07/68412.
ISA, International Search Report dated Apr. 25, 2008 for Application PCT/US07/68415.

* cited by examiner

ANTISENSE MODULATION OF APOLIPOPROTEIN B EXPRESSION

FIELD OF THE INVENTION

The present invention provides compositions and methods for modulating the expression of apolipoprotein B. In particular, this invention relates to compounds, particularly oligonucleotides, specifically hybridizable with nucleic acids encoding apolipoprotein B. Such compounds have been shown to modulate the expression of apolipoprotein B.

BACKGROUND OF THE INVENTION

Lipoproteins are globular, micelle-like particles that consist of a non-polar core of acylglycerols and cholesteryl esters surrounded by an amphiphilic coating of protein, phospholipid and cholesterol. Lipoproteins have been classified into five broad categories on the basis of their functional and physical properties: chylomicrons, which transport dietary lipids from intestine to tissues; very low density lipoproteins (VLDL); intermediate density lipoproteins (IDL); low density lipoproteins (LDL); all of which transport triacylglycerols and cholesterol from the liver to tissues; and high density lipoproteins (HDL), which transport endogenous cholesterol from tissues to the liver.

Lipoprotein particles undergo continuous metabolic processing and have variable properties and compositions. Lipoprotein densities increase without decreasing particle diameter because the density of their outer coatings is less than that of the inner core. The protein components of lipoproteins are known as apoliproteins. At least nine apolipoproteins are distributed in significant amounts among the various human lipoproteins.

Apolipoprotein B (also known as ApoB, apolipoprotein B-100; ApoB-100, apolipoprotein B-48; ApoB-48 and Ag(x) antigen), is a large glycoprotein that serves an indispensable role in the assembly and secretion of lipids and in the transport and receptor-mediated uptake and delivery of distinct classes of lipoproteins. The importance of apolipoprotein B spans a variety of functions, from the absorption and processing of dietary lipids to the regulation of circulating lipoprotein levels (Davidson and Shelness, *Annu. Rev. Nutr.*, 2000, 20, 169-193). This latter property underlies its relevance in terms of atherosclerosis susceptibility, which is highly correlated with the ambient concentration of apolipoprotein B-containing lipoproteins (Davidson and Shelness, *Annu. Rev. Nutr.*, 2000, 20, 169-193).

Two forms of apolipoprotein B exist in mammals. ApoB-100 represents the full-length protein containing 4536 amino acid residues synthesized exclusively in the human liver (Davidson and Shelness, *Annu. Rev. Nutr.*, 2000, 20, 169-193). A truncated form known as ApoB-48 is colinear with the amino terminal 2152 residues and is synthesized in the small intestine of all mammals (Davidson and Shelness, *Annu. Rev. Nutr.*, 2000, 20, 169-193).

ApoB-100 is the major protein component of LDL and contains the domain required for interaction of this lipoprotein species with the LDL receptor. In addition, ApoB-100 contains an unpaired cysteine residue which mediates an interaction with apolipoprotein(a) and generates another distinct atherogenic lipoprotein called Lp(a) (Davidson and Shelness, *Annu. Rev. Nutr.*, 2000, 20, 169-193).

In humans, ApoB-48 circulates in association with chylomicrons and chylomicron remnants and these particles are cleared by a distinct receptor known as the LDL-receptor-related protein (Davidson and Shelness, *Annu. Rev. Nutr.*, 2000, 20, 169-193). ApoB-48 can be viewed as a crucial adaptation by which dietary lipid is delivered from the small intestine to the liver, while ApoB-100 participates in the transport and delivery of endogenous plasma cholesterol (Davidson and Shelness, *Annu. Rev. Nutr.*, 2000, 20, 169-193).

The basis by which the common structural gene for apolipoprotein B produces two distinct protein isoforms is a process known as RNA editing. A site specific cytosine-to-uracil editing reaction produces a UAA stop codon and translational termination of apolipoprotein B to produce ApoB-48 (Davidson and Shelness, *Annu. Rev. Nutr.*, 2000, 20, 169-193).

Apolipoprotein B was cloned in 1985 (Law et al., *Proc. Natl. Acad. Sci. U.S.A.*, 1985, 82, 8340-8344) and mapped to chromosome 2p23-2p24 in 1986 (Deeb et al., *Proc. Natl. Acad. Sci. U.S.A.*, 1986, 83, 419-422).

Disclosed and claimed in U.S. Pat. No. 5,786,206 are methods and compositions for determining the level of low density lipoproteins (LDL) in plasma which include isolated DNA sequences encoding epitope regions of apolipoprotein B-100 (Smith et al., 1998).

Transgenic mice expressing human apolipoprotein B and fed a high-fat diet were found to develop high plasma cholesterol levels and displayed an 11-fold increase in atherosclerotic lesions over non-transgenic littermates (Kim and Young, *J. Lipid Res.*, 1998, 39, 703-723; Nishina et al., *J. Lipid Res.*, 1990, 31, 859-869).

In addition, transgenic mice expressing truncated forms of human apolipoprotein B have been employed to identify the carboxyl-terminal structural features of ApoB-100 that are required for interactions with apolipoprotein(a) to generate the Lp(a) lipoprotein particle and to investigate structural features of the LDL receptor-binding region of ApoB-100 (Kim and Young, *J. Lipid Res.*, 1998, 39, 703-723; McCormick et al., *J. Biol. Chem.*, 1997, 272, 23616-23622).

Apolipoprotein B knockout mice (bearing disruptions of both ApoB-100 and ApoB-48) have been generated which are protected from developing hypercholesterolemia when fed a high-fat diet (Farese et al., *Proc. Natl. Acad. Sci. U.S.A.*, 1995, 92, 1774-1778; Kim and Young, *J. Lipid Res.*, 1998, 39, 703-723). The incidence of atherosclerosis has been investigated in mice expressing exclusively ApoB-100 or ApoB-48 and susceptibility to atherosclerosis was found to be dependent on total cholesterol levels. Whether the mice synthesized ApoB-100 or ApoB-48 did not affect the extent of the atherosclerosis, indicating that there is probably no major difference in the intrinsic atherogenicity of ApoB-100 versus ApoB-48 (Kim and Young, *J. Lipid Res.*, 1998, 39, 703-723; Veniant et al., *J. Clin. Invest.*, 1997, 100, 180-188).

Elevated plasma levels of the ApoB-100-containing lipoprotein Lp(a) are associated with increased risk for atherosclerosis and its manifestations, which may include hypercholesterolemia (Seed et al., *N. Engl. J. Med.*, 1990, 322, 1494-1499), myocardial infarction (Sandkamp et al., *Clin. Chem.*, 1990, 36, 20-23), and thrombosis (Nowak-Gottl et al., *Pediatrics*, 1997, 99, E11).

The plasma concentration of Lp(a) is strongly influenced by heritable factors and is refractory to most drug and dietary manipulation (Katan and Beynen, *Am. J. Epidemiol.*, 1987, 125, 387-399; Vessby et al., *Atherosclerosis*, 1982, 44, 61-71). Pharmacologic therapy of elevated Lp(a) levels has been only modestly successful and apheresis remains the most effective therapeutic modality (Hajjar and Nachman, *Annu. Rev. Med.*, 1996, 47, 423-442).

Disclosed and claimed in U.S. Pat. No. 6,156,315 and the corresponding PCT publication WO 99/18986 is a method for inhibiting the binding of LDL to blood vessel matrix in a subject, comprising administering to the subject an effective amount of an antibody or a fragment thereof, which is capable of binding to the amino-terminal region of apolipoprotein B, thereby inhibiting the binding of low density lipoprotein to blood vessel matrix (Goldberg and Pillarisetti, 2000; Goldberg and Pillarisetti, 1999).

Disclosed and claimed in U.S. Pat. No. 6,096,516 are vectors containing cDNA encoding murine recombinant antibodies which bind to human ApoB-100 for the purpose of for diagnosis and treatment of cardiovascular diseases (Kwak et al., 2000).

Disclosed and claimed in PCT publication EP 911344 is a monoclonal antibody which specifically binds to ApoB-48 and does not specifically bind to ApoB-100, which is useful for diagnosis and therapy of hyperlipidemia and arterial sclerosis (Uchida and Kurano, 1998).

Disclosed and claimed in PCT publication WO 01/30354 are methods of treating a patient with a cardiovascular disorder, comprising administering a therapeutically effective amount of a compound to said patient, wherein said compound acts for a period of time to lower plasma concentrations of apolipoprotein B or apolipoprotein B-containing lipoproteins by stimulating a pathway for apolipoprotein B degradation (Fisher and Williams, 2001).

Disclosed and claimed in U.S. Pat. No. 5,220,006 is a cloned cis-acting DNA sequence that mediates the suppression of atherogenic apolipoprotein B (Ross et al., 1993).

Disclosed and claimed in PCT publication WO 01/12789 is a ribozyme which cleaves ApoB-100 mRNA specifically at position 6679 (Chan et al., 2001).

To date, strategies aimed at inhibiting apolipoprotein B function have been limited to Lp(a) apheresis, antibodies, antibody fragments and ribozymes. However, with the exception of Lp(a) apheresis, these investigative strategies are untested as therapeutic protocols. Consequently, there remains a long felt need for additional agents capable of effectively inhibiting apolipoprotein B function.

Antisense technology is emerging as an effective means of reducing the expression of specific gene products and may therefore prove to be uniquely useful in a number of therapeutic, diagnostic and research applications involving modulation of apolipoprotein B expression.

The present invention provides compositions and methods for modulating apolipoprotein B expression, including inhibition of the alternative isoform of apolipoprotein B, ApoB-48.

SUMMARY OF THE INVENTION

The present invention is directed to compounds, particularly antisense oligonucleotides, which are targeted to a nucleic acid encoding apolipoprotein B, and which modulate the expression of apolipoprotein B. Pharmaceutical and other compositions comprising the compounds of the invention are also provided. Further provided are methods of modulating the expression of apolipoprotein B in cells or tissues comprising contacting said cells or tissues with one or more of the antisense compounds or compositions of the invention. Further provided are methods of treating an animal, particularly a human, suspected of having or being prone to a disease or condition associated with expression of apolipoprotein B by administering a therapeutically or prophylactically effective amount of one or more of the antisense compounds or compositions of the invention.

DETAILED DESCRIPTION OF THE INVENTION

The present invention employs oligomeric compounds, particularly antisense oligonucleotides, for use in modulating the function of nucleic acid molecules encoding apolipoprotein B, ultimately modulating the amount of apolipoprotein B produced. This is accomplished by providing antisense compounds which specifically hybridize with one or more nucleic acids encoding apolipoprotein B. As used herein, the terms "target nucleic acid" and "nucleic acid encoding apolipoprotein B" encompass DNA encoding apolipoprotein B, RNA (including pre-mRNA and mRNA) transcribed from such DNA, and also cDNA derived from such RNA. The specific hybridization of an oligomeric compound with its target nucleic acid interferes with the normal function of the nucleic acid. This modulation of function of a target nucleic acid by compounds which specifically hybridize to it is generally referred to as "antisense". The functions of DNA to be interfered with include replication and transcription. The functions of RNA to be interfered with include all vital functions such as, for example, translocation of the RNA to the site of protein translation, translation of protein from the RNA, splicing of the RNA to yield one or more mRNA species, and catalytic activity which may be engaged in or facilitated by the RNA. The overall effect of such interference with target nucleic acid function is modulation of the expression of apolipoprotein B. In the context of the present invention, "modulation" means either an increase (stimulation) or a decrease (inhibition) in the expression of a gene. In the context of the present invention, inhibition is the preferred form of modulation of gene expression and mRNA is a preferred target.

It is preferred to target specific nucleic acids for antisense. "Targeting" an antisense compound to a particular nucleic acid, in the context of this invention, is a multistep process. The process usually begins with the identification of a nucleic acid sequence whose function is to be modulated. This may be, for example, a cellular gene (or mRNA transcribed from the gene) whose expression is associated with a particular disorder or disease state, or a nucleic acid molecule from an infectious agent. In the present invention, the target is a nucleic acid molecule encoding apolipoprotein B. The targeting process also includes determination of a site or sites within this gene for the antisense interaction to occur such that the desired effect, e.g., detection or modulation of expression of the protein, will result. Within the context of the present invention, a preferred intragenic site is the region encompassing the translation initiation or termination codon of the open reading frame (ORF) of the gene. Since, as is known in the art, the translation initiation codon is typically 5'-AUG (in transcribed mRNA molecules; 5'-ATG in the corresponding DNA molecule), the translation initiation codon is also referred to as the "AUG codon," the "start codon" or the "AUG start codon". A minority of genes have a translation initiation codon having the RNA sequence 5'-GUG, 5'-UUG or 5'-CUG, and 5'-AUA, 5'-ACG and 5'-CUG have been shown to function in vivo. Thus, the terms "translation initiation codon" and "start codon" can encompass many codon sequences, even though the initiator amino acid in each instance is typically methionine (in eukaryotes) or formylmethionine (in prokaryotes). It is also known in the art that eukaryotic and prokaryotic genes may have two or more alternative start codons, any one of which may be preferentially utilized for translation initiation in a particular cell type or tissue, or under a particular set of conditions. In the context of the invention, "start codon" and "translation initiation codon" refer to the codon or codons that are used in vivo to initiate translation of an mRNA molecule transcribed from a gene encoding apolipoprotein B, regardless of the sequence(s) of such codons.

It is also known in the art that a translation termination codon (or "stop codon") of a gene may have one of three sequences, i.e., 5'-UAA, 5'-UAG and 5'-UGA (the corresponding DNA sequences are 5'-TAA, 5'-TAG and 5'-TGA, respectively). The terms "start codon region" and "translation initiation codon region" refer to a portion of such an mRNA or gene that encompasses from about 25 to about 50 contiguous nucleotides in either direction (i.e., 5' or 3') from a translation initiation codon. Similarly, the terms "stop codon region" and "translation termination codon region" refer to a portion of such an mRNA or gene that encompasses from about 25 to about 50 contiguous nucleotides in either direction (i.e., 5' or 3') from a translation termination codon.

The open reading frame (ORF) or "coding region," which is known in the art to refer to the region between the translation initiation codon and the translation termination codon, is also a region which may be targeted effectively. Other target regions include the 5' untranslated region (5'UTR), known in the art to refer to the portion of an mRNA in the 5' direction from the translation initiation codon, and thus including nucleotides between the 5' cap site and the translation initiation codon of an mRNA or corresponding nucleotides on the gene, and the 3' untranslated region (3'UTR), known in the art to refer to the portion of an mRNA in the 3' direction from the translation termination codon, and thus including nucleotides between the translation termination codon and 3' end of an mRNA or corresponding nucleotides on the gene. The 5' cap of an mRNA comprises an N7-methylated guanosine residue joined to the 5'-most residue of the mRNA via a 5'-5' triphosphate linkage. The 5' cap region of an mRNA is considered to include the 5' cap structure itself as well as the first 50 nucleotides adjacent to the cap. The 5' cap region may also be a preferred target region.

Although some eukaryotic mRNA transcripts are directly translated, many contain one or more regions, known as "introns," which are excised from a transcript before it is translated. The remaining (and therefore translated) regions are known as "exons" and are spliced together to form a continuous mRNA sequence. mRNA splice sites, i.e., intron-exon junctions, may also be preferred target regions, and are particularly useful in situations where aberrant splicing is implicated in disease, or where an overproduction of a particular mRNA splice product is implicated in disease. Aberrant fusion junctions due to rearrangements or deletions are also preferred targets. It has also been found that introns can also be effective, and therefore preferred, target regions for antisense compounds targeted, for example, to DNA or pre-mRNA.

Once one or more target sites have been identified, oligonucleotides are chosen which are sufficiently complementary to the target, i.e., hybridize sufficiently well and with sufficient specificity, to give the desired effect.

In the context of this invention, "hybridization" means hydrogen bonding, which may be Watson-Crick, Hoogsteen or reversed Hoogsteen hydrogen bonding, between complementary nucleoside or nucleotide bases. For example, adenine and thymine are complementary nucleobases which pair through the formation of hydrogen bonds. "Complementary," as used herein, refers to the capacity for precise pairing between two nucleotides. For example, if a nucleotide at a certain position of an oligonucleotide is capable of hydrogen bonding with a nucleotide at the same position of a DNA or RNA molecule, then the oligonucleotide and the DNA or RNA are considered to be complementary to each other at that position. The oligonucleotide and the DNA or RNA are complementary to each other when a sufficient number of corresponding positions in each molecule are occupied by nucleotides which can hydrogen bond with each other. Thus, "specifically hybridizable" and "complementary" are terms which are used to indicate a sufficient degree of complementarity or precise pairing such that stable and specific binding occurs between the oligonucleotide and the DNA or RNA target. It is understood in the art that the sequence of an antisense compound need not be 100% complementary to that of its target nucleic acid to be specifically hybridizable. An antisense compound is specifically hybridizable when binding of the compound to the target DNA or RNA molecule interferes with the normal function of the target DNA or RNA to cause a loss of utility, and there is a sufficient degree of complementarity to avoid non-specific binding of the antisense compound to non-target sequences under conditions in which specific binding is desired, i.e., under physiological conditions in the case of in vivo assays or therapeutic treatment, and in the case of in vitro assays, under conditions in which the assays are performed.

Antisense and other compounds of the invention which hybridize to the target and inhibit expression of the target are identified through experimentation, and the sequences of these compounds are hereinbelow identified as preferred embodiments of the invention. The target sites to which these preferred sequences are complementary are hereinbelow referred to as "active sites" and are therefore preferred sites for targeting. Therefore another embodiment of the invention encompasses compounds which hybridize to these active sites.

Antisense compounds are commonly used as research reagents and diagnostics. For example, antisense oligonucleotides, which are able to inhibit gene expression with exquisite specificity, are often used by those of ordinary skill to elucidate the function of particular genes. Antisense compounds are also used, for example, to distinguish between functions of various members of a biological pathway. Antisense modulation has, therefore, been harnessed for research use.

For use in kits and diagnostics, the antisense compounds of the present invention, either alone or in combination with other antisense compounds or therapeutics, can be used as tools in differential and/or combinatorial analyses to elucidate expression patterns of a portion or the entire complement of genes expressed within cells and tissues.

Expression patterns within cells or tissues treated with one or more antisense compounds are compared to control cells or tissues not treated with antisense compounds and the patterns produced are analyzed for differential levels of gene expression as they pertain, for example, to disease association, signaling pathway, cellular localization, expression level, size, structure or function of the genes examined. These analyses can be performed on stimulated or unstimulated cells and in the presence or absence of other compounds which affect expression patterns.

Examples of methods of gene expression analysis known in the art include DNA arrays or microarrays (Brazma and Vilo, *FEBS Lett.*, 2000, 480, 17-24; Celis, et al., *FEBS Lett.*, 2000, 480, 2-16), SAGE (serial analysis of gene expression) (Madden, et al., *Drug Discov. Today*, 2000, 5, 415-425), READS (restriction enzyme amplification of digested cDNAs) (Prashar and Weissman, *Methods Enzymol.*, 1999, 303, 258-72), TOGA (total gene expression analysis) (Sutcliffe, et al., *Proc. Natl. Acad. Sci. U.S.A.*, 2000, 97, 1976-81), protein arrays and proteomics (Celis, et al., *FEBS Lett.*, 2000, 480, 2-16; Jungblut, et al., *Electrophoresis*, 1999, 20, 2100-10), expressed sequence tag (EST) sequencing (Celis, et al., *FEBS Lett.*, 2000, 480, 2-16; Larsson, et al., *J. Biotechnol.*, 2000, 80, 143-57), subtractive RNA fingerprinting (SuRF) (Fuchs, et al., *Anal. Biochem.*, 2000, 286, 91-98; Larson, et al., *Cytometry*, 2000, 41, 203-208), subtractive cloning, differential display (DD) (Jurecic and Belmont, *Curr. Opin. Microbiol.*, 2000, 3, 316-21), comparative genomic hybridization (Carulli, et al., *J. Cell Biochem. Suppl.*, 1998, 31, 286-96), FISH (fluorescent in situ hybridization) techniques (Going and Gusterson, *Eur. J. Cancer*, 1999, 35, 1895-904) and mass spectrometry methods (reviewed in (To, *Comb. Chem. High Throughput Screen*, 2000, 3, 235-41).

The specificity and sensitivity of antisense is also harnessed by those of skill in the art for therapeutic uses. Antisense oligonucleotides have been employed as therapeutic moieties in the treatment of disease states in animals and man. Antisense oligonucleotide drugs, including ribozymes, have been safely and effectively administered to humans and numerous clinical trials are presently underway. It is thus established that oligonucleotides can be useful therapeutic modalities that can be configured to be useful in treatment regimes for treatment of cells, tissues and animals, especially humans.

In the context of this invention, the term "oligonucleotide" refers to an oligomer or polymer of ribonucleic acid (RNA) or deoxyribonucleic acid (DNA) or mimetics thereof. This term includes oligonucleotides composed of naturally-occurring nucleobases, sugars and covalent internucleoside (backbone) linkages as well as oligonucleotides having non-naturally-occurring portions which function similarly. Such modified or substituted oligonucleotides are often preferred over native forms because of desirable properties such as, for example, enhanced cellular uptake, enhanced affinity for nucleic acid target and increased stability in the presence of nucleases.

While antisense oligonucleotides are a preferred form of antisense compound, the present invention comprehends other oligomeric antisense compounds, including but not limited to oligonucleotide mimetics such as are described below. The antisense compounds in accordance with this invention preferably comprise from about 8 to about 50 nucleobases (i.e. from about 8 to about 50 linked nucleosides). Particularly preferred antisense compounds are antisense oligonucleotides, even more preferably those comprising from about 12 to about 30 nucleobases. Antisense compounds include ribozymes, external guide sequence (EGS) oligonucleotides (oligozymes), and other short catalytic RNAs or catalytic oligonucleotides which hybridize to the target nucleic acid and modulate its expression.

As is known in the art, a nucleoside is a base-sugar combination. The base portion of the nucleoside is normally a heterocyclic base. The two most common classes of such heterocyclic bases are the purines and the pyrimidines. Nucleotides are nucleosides that further include a phosphate group covalently linked to the sugar portion of the nucleoside. For those nucleosides that include a pentofuranosyl sugar, the phosphate group can be linked to either the 2', 3' or 5' hydroxyl moiety of the sugar. In forming oligonucleotides, the phosphate groups covalently link adjacent nucleosides to one another to form a linear polymeric compound. In turn the respective ends of this linear polymeric structure can be further joined to form a circular structure, however, open linear structures are generally preferred. Within the oligonucleotide structure, the phosphate groups are commonly referred to as forming the internucleoside backbone of the oligonucleotide. The normal linkage or backbone of RNA and DNA is a 3' to 5' phosphodiester linkage.

Specific examples of preferred antisense compounds useful in this invention include oligonucleotides containing modified backbones or non-natural internucleoside linkages. As defined in this specification, oligonucleotides having modified backbones include those that retain a phosphorus atom in the backbone and those that do not have a phosphorus atom in the backbone. For the purposes of this specification, and as sometimes referenced in the art, modified oligonucleotides that do not have a phosphorus atom in their internucleoside backbone can also be considered to be oligonucleosides.

Preferred modified oligonucleotide backbones include, for example, phosphorothioates, chiral phosphorothioates, phosphorodithioates, phosphotriesters, aminoalkyl-phosphotriesters, methyl and other alkyl phosphonates including 3'-alkylene phosphonates, 5'-alkylene phosphonates and chiral phosphonates, phosphinates, phosphoramidates including 3'-amino phosphoramidate and aminoalkylphosphoramidates, thionophosphoramidates, thionoalkylphosphonates, thionoalkylphosphotriesters, selenophosphates and boranophosphates having normal 3'-5' linkages, 2'-5' linked analogs of these, and those having inverted polarity wherein one or more internucleotide linkages is a 3' to 3', 5' to 5' or 2' to 2' linkage. Preferred oligonucleotides having inverted polarity comprise a single 3' to 3' linkage at the 3'-most internucleotide linkage i.e. a single inverted nucleoside residue which may be abasic (the nucleobase is missing or has a hydroxyl group in place thereof). Various salts, mixed salts and free acid forms are also included.

Representative United States patents that teach the preparation of the above phosphorus-containing linkages include, but are not limited to, U.S. Pat. Nos. 3,687,808; 4,469,863; 4,476,301; 5,023,243; 5,177,196; 5,188,897; 5,264,423; 5,276,019; 5,278,302; 5,286,717; 5,321,131; 5,399,676; 5,405,939; 5,453,496; 5,455,233; 5,466,677; 5,476,925; 5,519,126; 5,536,821; 5,541,306; 5,550,111; 5,563,253; 5,571,799; 5,587,361; 5,194,599; 5,565,555; 5,527,899; 5,721,218; 5,672,697 and 5,625,050, certain of which are commonly owned with this application, and each of which is herein incorporated by reference.

Preferred modified oligonucleotide backbones that do not include a phosphorus atom therein have backbones that are formed by short chain alkyl or cycloalkyl internucleoside linkages, mixed heteroatom and alkyl or cycloalkyl internucleoside linkages, or one or more short chain heteroatomic or heterocyclic internucleoside linkages. These include those having morpholino linkages (formed in part from the sugar portion of a nucleoside); siloxane backbones; sulfide, sulfoxide and sulfone backbones; formacetyl and thioformacetyl backbones; methylene formacetyl and thioformacetyl backbones; riboacetyl backbones; alkene containing backbones; sulfamate backbones; methyleneimino and methylenehydrazino backbones; sulfonate and sulfonamide backbones; amide backbones; and others having mixed N, O, S and $CH_2$ component parts.

Representative United States patents that teach the preparation of the above oligonucleosides include, but are not limited to, U.S. Pat. Nos. 5,034,506; 5,166,315; 5,185,444; 5,214,134; 5,216,141; 5,235,033; 5,264,562; 5,264,564; 5,405,938; 5,434,257; 5,466,677; 5,470,967; 5,489,677; 5,541,307; 5,561,225; 5,596,086; 5,602,240; 5,610,289; 5,602,240; 5,608,046; 5,610,289; 5,618,704; 5,623,070; 5,663,312; 5,633,360; 5,677,437; 5,792,608; 5,646,269 and 5,677,439, certain of which are commonly owned with this application, and each of which is herein incorporated by reference.

In other preferred oligonucleotide mimetics, both the sugar and the internucleoside linkage, i.e., the backbone, of the nucleotide units are replaced with novel groups. The base units are maintained for hybridization with an appropriate nucleic acid target compound. One such oligomeric compound, an oligonucleotide mimetic that has been shown to have excellent hybridization properties, is referred to as a peptide nucleic acid (PNA). In PNA compounds, the sugar-backbone of an oligonucleotide is replaced with an amide containing backbone, in particular an aminoethylglycine backbone. The nucleobases are retained and are bound directly or indirectly to aza nitrogen atoms of the amide portion of the backbone. Representative United States patents that teach the preparation of PNA compounds include, but are not limited to, U.S. Pat. Nos. 5,539,082; 5,714,331; and 5,719,262, each of which is herein incorporated by reference. Further teaching of PNA compounds can be found in Nielsen et al., *Science,* 1991, 254, 1497-1500.

Most preferred embodiments of the invention are oligonucleotides with phosphorothioate backbones and oligonucleosides with heteroatom backbones, and in particular —$CH_2$—NH—O—$CH_2$—, —$CH_2$—N($CH_3$)—O—$CH_2$— [known as a methylene (methylimino) or MMI backbone], —$CH_2$—O—N($CH_3$)—$CH_2$—, —$CH_2$—N($CH_3$)—N($CH_3$)—$CH_2$— and —O—N($CH_3$)—$CH_2$—$CH_2$— [wherein the native phosphodiester backbone is represented as —O—P—O—$CH_2$—] of the above referenced U.S. Pat. No. 5,489,677, and the amide backbones of the above referenced U.S. Pat. No. 5,602,240. Also preferred are oligonucleotides having morpholino backbone structures of the above-referenced U.S. Pat. No. 5,034,506.

Modified oligonucleotides may also contain one or more substituted sugar moieties. Preferred oligonucleotides comprise one of the following at the 2' position: OH; F; O-, S-, or N-alkyl; O-, S-, or N-alkenyl; O-, S- or N-alkynyl; or O-alkyl-O-alkyl, wherein the alkyl, alkenyl and alkynyl may be substituted or unsubstituted $C_1$ to $C_{10}$ alkyl or $C_2$ to $C_{10}$ alkenyl and alkynyl. Particularly preferred are O[($CH_2$)$_n$O]$_m$$CH_3$, O($CH_2$)$_n$O$CH_3$, O($CH_2$)$_n$$NH_2$, O($CH_2$)$_n$$CH_3$, O($CH_2$)$_n$ON$H_2$, and O($CH_2$)$_n$ON[($CH_2$)$_n$$CH_3$)]$_2$, where n and m are from 1 to about 10. Other preferred oligonucleotides comprise one of the following at the 2' position: $C_1$ to $C_{10}$ lower alkyl, substituted lower alkyl, alkenyl, alkynyl, alkaryl, aralkyl, O-alkaryl or O-aralkyl, SH, $SCH_3$, OCN, Cl, Br, CN, $CF_3$, $OCF_3$, $SOCH_3$, $SO_2CH_3$, $ONO_2$, $NO_2$, $N_3$, $NH_2$, heterocycloalkyl, heterocycloalkaryl, aminoalkylamino, polyalkylamino, substituted silyl, an RNA cleaving group, a reporter group, an intercalator, a group for improving the pharmacokinetic properties of an oligonucleotide, or a group for improving the pharmacodynamic properties of an oligonucleotide, and other substituents having similar properties. A preferred modification includes 2'-methoxyethoxy (2'-O—$CH_2CH_2OCH_3$, also known as 2'-O-(2-methoxyethyl) or 2'-MOE) (Martin et al., *Helv. Chim. Acta,* 1995, 78, 486-504) i.e., an alkoxyalkoxy group. A further preferred modification includes 2'-dimethylaminooxyethoxy, i.e., a O($CH_2$)$_2$ON($CH_3$)$_2$ group, also known as 2'-DMAOE, as described in examples hereinbelow, and 2'-dimethylaminoethoxyethoxy (also known in the art as 2'-O-dimethylaminoethoxyethyl or 2'-DMAEOE), i.e., 2'-O—$CH_2$—O—$CH_2$—N($CH_3$)$_2$, also described in examples hereinbelow.

A further preferred modification includes Locked Nucleic Acids (LNAs) in which the 2'-hydroxyl group is linked to the 3' or 4' carbon atom of the sugar ring thereby forming a bicyclic sugar moiety. The linkage is preferably a methelyne (—$CH_2$—)$_n$ group bridging the 2' oxygen atom and the 4' carbon atom wherein n is 1 or 2. LNAs and preparation thereof are described in WO 98/39352 and WO 99/14226.

Other preferred modifications include 2'-methoxy (2'-O—$CH_3$), 2'-aminopropoxy (2'-O$CH_2CH_2CH_2NH_2$), 2'-allyl (2'-$CH_2$—CH=$CH_2$), 2'-O-allyl (2'-O—$CH_2$—CH=$CH_2$) and 2'-fluoro (2'-F). The 2'-modification may be in the arabino (up) position or ribo (down) position. A preferred 2'-arabino modification is 2'-F. Similar modifications may also be made at other positions on the oligonucleotide, particularly the 3' position of the sugar on the 3' terminal nucleotide or in 2'-5' linked oligonucleotides and the 5' position of 5' terminal nucleotide. Oligonucleotides may also have sugar mimetics such as cyclobutyl moieties in place of the pentofuranosyl sugar. Representative United States patents that teach the preparation of such modified sugar structures include, but are not limited to, U.S. Pat. Nos. 4,981,957; 5,118,800; 5,319,080; 5,359,044; 5,393,878; 5,446,137; 5,466,786; 5,514,785; 5,519,134; 5,567,811; 5,576,427; 5,591,722; 5,597,909; 5,610,300; 5,627,053; 5,639,873; 5,646,265; 5,658,873; 5,670,633; 5,792,747; and 5,700,920, certain of which are commonly owned with the instant application, and each of which is herein incorporated by reference in its entirety.

Oligonucleotides may also include nucleobase (often referred to in the art simply as "base") modifications or substitutions. As used herein, "unmodified" or "natural" nucleobases include the purine bases adenine (A) and guanine (G), and the pyrimidine bases thymine (T), cytosine (C) and uracil (U). Modified nucleobases include other synthetic and natural nucleobases such as 5-methylcytosine (5-me-C), 5-hydroxymethyl cytosine, xanthine, hypoxanthine, 2-aminoadenine, 6-methyl and other alkyl derivatives of adenine and guanine, 2-propyl and other alkyl derivatives of adenine and guanine, 2-thiouracil, 2-thiothymine and 2-thiocytosine, 5-halouracil and cytosine, 5-propynyl (—C≡C—$CH_3$) uracil and cytosine and other alkynyl derivatives of pyrimidine bases, 6-azo uracil, cytosine and thymine, 5-uracil (pseudouracil), 4-thiouracil, 8-halo, 8-amino, 8-thiol, 8-thioalkyl, 8-hydroxyl and other 8-substituted adenines and guanines, 5-halo particularly 5-bromo, 5-trifluoromethyl and other 5-substituted uracils and cytosines, 7-methylguanine and 7-methyladenine, 2-F-adenine, 2-amino-adenine, 8-azaguanine and 8-azaadenine, 7-deazaguanine and 7-deazaadenine and 3-deazaguanine and 3-deazaadenine. Further modified nucleobases include tricyclic pyrimidines such as phenoxazine cytidine(1H-pyrimido[5,4-b][1,4]benzoxazin-2(3H)-one), phenothiazine cytidine (1H-pyrimido[5,4-b][1,4]benzothiazin-2(3H)-one), G-clamps such as a substituted phenoxazine cytidine (e.g. 9-(2-aminoethoxy)-H-pyrimido [5,4-b][1,4]benzoxazin-2(3H)-one), carbazole cytidine (2H-pyrimido[4,5-b]indol-2-one), pyridoindole cytidine (H-pyrido[3',2':4,5]pyrrolo[2,3-d]pyrimidin-2-one). Modified nucleobases may also include those in which the purine or pyrimidine base is replaced with other heterocycles, for example 7-deaza-adenine, 7-deazaguanosine, 2-aminopyridine and 2-pyridone. Further nucleobases include those disclosed in U.S. Pat. No. 3,687,808, those disclosed in *The Concise Encyclopedia Of Polymer Science And Engineering,* pages 858-859, Kroschwitz, J. I., ed. John Wiley & Sons, 1990, those disclosed by Englisch et al., *Angewandte Chemie,* International Edition, 1991, 30, 613, and those disclosed by Sanghvi, Y. S., Chapter 15, *Antisense Research and Applications,* pages 289-302, Crooke, S. T. and Lebleu, B., ed., CRC Press, 1993. Certain of these nucleobases are particularly useful for increasing the binding affinity of the oligomeric compounds of the invention. These include 5-substituted pyrimidines, 6-azapyrimidines and N-2, N-6 and O-6 substituted purines, including 2-aminopropyl-adenine, 5-propynyluracil and 5-propynylcytosine. 5-methylcytosine substitutions have been shown to increase nucleic acid duplex stability by 0.6-1.2° C. (Sanghvi, Y. S., Crooke, S. T. and Lebleu, B., eds., *Antisense Research and Applications*, CRC Press, Boca Raton, 1993, pp. 276-278) and are presently preferred base substitutions, even more particularly when combined with 2'-O-methoxyethyl sugar modifications.

Representative United States patents that teach the preparation of certain of the above noted modified nucleobases as well as other modified nucleobases include, but are not limited to, the above noted U.S. Pat. No. 3,687,808, as well as U.S. Pat. Nos. 4,845,205; 5,130,302; 5,134,066; 5,175,273; 5,367,066; 5,432,272; 5,457,187; 5,459,255; 5,484,908; 5,502,177; 5,525,711; 5,552,540; 5,587,469; 5,594,121; 5,596,091; 5,614,617; 5,645,985; 5,830,653; 5,763,588; 6,005,096; and 5,681,941, certain of which are commonly owned with the instant application, and each of which is herein incorporated by reference, and U.S. Pat. No. 5,750,692, which is commonly owned with the instant application and also herein incorporated by reference.

Another modification of the oligonucleotides of the invention involves chemically linking to the oligonucleotide one or more moieties or conjugates which enhance the activity, cellular distribution or cellular uptake of the oligonucleotide. The compounds of the invention can include conjugate groups covalently bound to functional groups such as primary or secondary hydroxyl groups. Conjugate groups of the invention include intercalators, reporter molecules, polyamines, polyamides, polyethylene glycols, polyethers, groups that enhance the pharmacodynamic properties of oligomers, and groups that enhance the pharmacokinetic properties of oligomers. Typical conjugates groups include cholesterols, lipids, phospholipids, biotin, phenazine, folate, phenanthridine, anthraquinone, acridine, fluoresceins, rhodamines, coumarins, and dyes. Groups that enhance the pharmacodynamic properties, in the context of this invention, include groups that improve oligomer uptake, enhance oligomer resistance to degradation, and/or strengthen sequence-specific hybridization with RNA. Groups that enhance the pharmacokinetic properties, in the context of this invention, include groups that improve oligomer uptake, distribution, metabolism or excretion. Representative conjugate groups are disclosed in International Patent Application PCT/US92/09196, filed Oct. 23, 1992 the entire disclosure of which is incorporated herein by reference. Conjugate moieties include but are not limited to lipid moieties such as a cholesterol moiety (Letsinger et al., *Proc. Natl. Acad. Sci. USA*, 1989, 86, 6553-6556), cholic acid (Manoharan et al., *Bioorg. Med. Chem. Let.*, 1994, 4, 1053-1060), a thioether, e.g., hexyl-S-tritylthiol (Manoharan et al., *Ann. N.Y. Acad. Sci.*, 1992, 660, 306-309; Manoharan et al., *Bioorg. Med. Chem. Let.*, 1993, 3, 2765-2770), a thiocholesterol (Oberhauser et al., *Nucl. Acids Res.*, 1992, 20, 533-538), an aliphatic chain, e.g., dodecandiol or undecyl residues (Saison-Behmoaras et al., *EMBO J.*, 1991, 10, 1111-1118; Kabanov et al., *FEBS Lett.*, 1990, 259, 327-330; Svinarchuk et al., *Biochimie*, 1993, 75, 49-54), a phospholipid, e.g., di-hexadecyl-rac-glycerol or triethylammonium 1,2-di-O-hexadecyl-rac-glycero-3-H-phosphonate (Manoharan et al., *Tetrahedron Lett.*, 1995, 36, 3651-3654; Shea et al., *Nucl. Acids Res.*, 1990, 18, 3777-3783), a polyamine or a polyethylene glycol chain (Manoharan et al., *Nucleosides & Nucleotides*, 1995, 14, 969-973), or adamantane acetic acid (Manoharan et al., *Tetrahedron Lett.*, 1995, 36, 3651-3654), a palmityl moiety (Mishra et al., *Biochim. Biophys. Acta*, 1995, 1264, 229-237), or an octadecylamine or hexylamino-carbonyl-oxycholesterol moiety (Crooke et al., *J. Pharmacol. Exp. Ther.*, 1996, 277, 923-937. Oligonucleotides of the invention may also be conjugated to active drug substances, for example, aspirin, warfarin, phenylbutazone, ibuprofen, suprofen, fenbufen, ketoprofen, (S)-(+)-pranoprofen, carprofen, dansylsarcosine, 2,3,5-triiodobenzoic acid, flufenamic acid, folinic acid, a benzothiadiazide, chlorothiazide, a diazepine, indo-methicin, a barbiturate, a cephalosporin, a sulfa drug, an antidiabetic, an antibacterial or an antibiotic. Oligonucleotide-drug conjugates and their preparation are described in U.S. patent application Ser. No. 09/334,130 (filed Jun. 15, 1999) which is incorporated herein by reference in its entirety.

Representative United States patents that teach the preparation of such oligonucleotide conjugates include, but are not limited to, U.S. Pat. Nos. 4,828,979; 4,948,882; 5,218,105; 5,525,465; 5,541,313; 5,545,730; 5,552,538; 5,578,717, 5,580,731; 5,580,731; 5,591,584; 5,109,124; 5,118,802; 5,138,045; 5,414,077; 5,486,603; 5,512,439; 5,578,718; 5,608,046; 4,587,044; 4,605,735; 4,667,025; 4,762,779; 4,789,737; 4,824,941; 4,835,263; 4,876,335; 4,904,582; 4,958,013; 5,082,830; 5,112,963; 5,214,136; 5,082,830; 5,112,963; 5,214,136; 5,245,022; 5,254,469; 5,258,506; 5,262,536; 5,272,250; 5,292,873; 5,317,098; 5,371,241; 5,391,723; 5,416,203; 5,451,463; 5,510,475; 5,512,667; 5,514,785; 5,565,552; 5,567,810; 5,574,142; 5,585,481; 5,587,371; 5,595,726; 5,597,696; 5,599,923; 5,599,928 and 5,688,941, certain of which are commonly owned with the instant application, and each of which is herein incorporated by reference.

It is not necessary for all positions in a given compound to be uniformly modified, and in fact more than one of the aforementioned modifications may be incorporated in a single compound or even at a single nucleoside within an oligonucleotide. The present invention also includes antisense compounds which are chimeric compounds. "Chimeric" antisense compounds or "chimeras," in the context of this invention, are antisense compounds, particularly oligonucleotides, which contain two or more chemically distinct regions, each made up of at least one monomer unit, i.e., a nucleotide in the case of an oligonucleotide compound. These oligonucleotides typically contain at least one region wherein the oligonucleotide is modified so as to confer upon the oligonucleotide increased resistance to nuclease degradation, increased cellular uptake, and/or increased binding affinity for the target nucleic acid. An additional region of the oligonucleotide may serve as a substrate for enzymes capable of cleaving RNA:DNA or RNA:RNA hybrids. By way of example, RNase H is a cellular endonuclease which cleaves the RNA strand of an RNA:DNA duplex. Activation of RNase H, therefore, results in cleavage of the RNA target, thereby greatly enhancing the efficiency of oligonucleotide inhibition of gene expression. Consequently, comparable results can often be obtained with shorter oligonucleotides when chimeric oligonucleotides are used, compared to phosphorothioate deoxyoligonucleotides hybridizing to the same target region. Cleavage of the RNA target can be routinely detected by gel electrophoresis and, if necessary, associated nucleic acid hybridization techniques known in the art.

Chimeric antisense compounds of the invention may be formed as composite structures of two or more oligonucleotides, modified oligonucleotides, oligonucleosides and/or oligonucleotide mimetics as described above. Such compounds have also been referred to in the art as hybrids or gapmers. Representative United States patents that teach the preparation of such hybrid structures include, but are not limited to, U.S. Pat. Nos. 5,013,830; 5,149,797; 5,220,007;

5,256,775; 5,366,878; 5,403,711; 5,491,133; 5,565,350; 5,623,065; 5,652,355; 5,652,356; and 5,700,922, certain of which are commonly owned with the instant application, and each of which is herein incorporated by reference in its entirety.

The antisense compounds used in accordance with this invention may be conveniently and routinely made through the well-known technique of solid phase synthesis. Equipment for such synthesis is sold by several vendors including, for example, Applied Biosystems (Foster City, Calif.). Any other means for such synthesis known in the art may additionally or alternatively be employed. It is well known to use similar techniques to prepare oligonucleotides such as the phosphorothioates and alkylated derivatives.

The antisense compounds of the invention are synthesized in vitro and do not include antisense compositions of biological origin, or genetic vector constructs designed to direct the in vivo synthesis of antisense molecules.

The compounds of the invention may also be admixed, encapsulated, conjugated or otherwise associated with other molecules, molecule structures or mixtures of compounds, as for example, liposomes, receptor targeted molecules, oral, rectal, topical or other formulations, for assisting in uptake, distribution and/or absorption. Representative United States patents that teach the preparation of such uptake, distribution and/or absorption assisting formulations include, but are not limited to, U.S. Pat. Nos. 5,108,921; 5,354,844; 5,416,016; 5,459,127; 5,521,291; 5,543,158; 5,547,932; 5,583,020; 5,591,721; 4,426,330; 4,534,899; 5,013,556; 5,108,921; 5,213,804; 5,227,170; 5,264,221; 5,356,633; 5,395,619; 5,416,016; 5,417,978; 5,462,854; 5,469,854; 5,512,295; 5,527,528; 5,534,259; 5,543,152; 5,556,948; 5,580,575; and 5,595,756, each of which is herein incorporated by reference.

The antisense compounds of the invention encompass any pharmaceutically acceptable salts, esters, or salts of such esters, or any other compound which, upon administration to an animal including a human, is capable of providing (directly or indirectly) the biologically active metabolite or residue thereof. Accordingly, for example, the disclosure is also drawn to prodrugs and pharmaceutically acceptable salts of the compounds of the invention, pharmaceutically acceptable salts of such prodrugs, and other bioequivalents.

The term "prodrug" indicates a therapeutic agent that is prepared in an inactive form that is converted to an active form (i.e., drug) within the body or cells thereof by the action of endogenous enzymes or other chemicals and/or conditions. In particular, prodrug versions of the oligonucleotides of the invention are prepared as SATE [(S-acetyl-2-thioethyl) phosphate] derivatives according to the methods disclosed in WO 93/24510 to Gosselin et al., published Dec. 9, 1993 or in WO 94/26764 and U.S. Pat. No. 5,770,713 to Imbach et al.

The term "pharmaceutically acceptable salts" refers to physiologically and pharmaceutically acceptable salts of the compounds of the invention: i.e., salts that retain the desired biological activity of the parent compound and do not impart undesired toxicological effects thereto.

Pharmaceutically acceptable base addition salts are formed with metals or amines, such as alkali and alkaline earth metals or organic amines. Examples of metals used as cations are sodium, potassium, magnesium, calcium, and the like. Examples of suitable amines are N,N'-dibenzylethylenediamine, chloroprocaine, choline, diethanolamine, dicyclohexylamine, ethylenediamine, N-methylglucamine, and procaine (see, for example, Berge et al., "Pharmaceutical Salts," *J. of Pharma Sci.*, 1977, 66, 1-19). The base addition salts of said acidic compounds are prepared by contacting the free acid form with a sufficient amount of the desired base to produce the salt in the conventional manner. The free acid form may be regenerated by contacting the salt form with an acid and isolating the free acid in the conventional manner. The free acid forms differ from their respective salt forms somewhat in certain physical properties such as solubility in polar solvents, but otherwise the salts are equivalent to their respective free acid for purposes of the present invention. As used herein, a "pharmaceutical addition salt" includes a pharmaceutically acceptable salt of an acid form of one of the components of the compositions of the invention. These include organic or inorganic acid salts of the amines. Preferred acid salts are the hydrochlorides, acetates, salicylates, nitrates and phosphates. Other suitable pharmaceutically acceptable salts are well known to those skilled in the art and include basic salts of a variety of inorganic and organic acids, such as, for example, with inorganic acids, such as for example hydrochloric acid, hydrobromic acid, sulfuric acid or phosphoric acid; with organic carboxylic, sulfonic, sulfo or phospho acids or N-substituted sulfamic acids, for example acetic acid, propionic acid, glycolic acid, succinic acid, maleic acid, hydroxymaleic acid, methylmaleic acid, fumaric acid, malic acid, tartaric acid, lactic acid, oxalic acid, gluconic acid, glucaric acid, glucuronic acid, citric acid, benzoic acid, cinnamic acid, mandelic acid, salicylic acid, 4-aminosalicylic acid, 2-phenoxybenzoic acid, 2-acetoxybenzoic acid, embonic acid, nicotinic acid or isonicotinic acid; and with amino acids, such as the 20 alpha-amino acids involved in the synthesis of proteins in nature, for example glutamic acid or aspartic acid, and also with phenylacetic acid, methanesulfonic acid, ethanesulfonic acid, 2-hydroxyethanesulfonic acid, ethane-1,2-disulfonic acid, benzenesulfonic acid, 4-methylbenzenesulfonic acid, naphthalene-2-sulfonic acid, naphthalene-1,5-disulfonic acid, 2- or 3-phosphoglycerate, glucose-6-phosphate, N-cyclohexylsulfamic acid (with the formation of cyclamates), or with other acid organic compounds, such as ascorbic acid. Pharmaceutically acceptable salts of compounds may also be prepared with a pharmaceutically acceptable cation. Suitable pharmaceutically acceptable cations are well known to those skilled in the art and include alkaline, alkaline earth, ammonium and quaternary ammonium cations. Carbonates or hydrogen carbonates are also possible.

For oligonucleotides, preferred examples of pharmaceutically acceptable salts include but are not limited to (a) salts formed with cations such as sodium, potassium, ammonium, magnesium, calcium, polyamines such as spermine and spermidine, etc.; (b) acid addition salts formed with inorganic acids, for example hydrochloric acid, hydrobromic acid, sulfuric acid, phosphoric acid, nitric acid and the like; (c) salts formed with organic acids such as, for example, acetic acid, oxalic acid, tartaric acid, succinic acid, maleic acid, fumaric acid, gluconic acid, citric acid, malic acid, ascorbic acid, benzoic acid, tannic acid, palmitic acid, alginic acid, polyglutamic acid, naphthalenesulfonic acid, methanesulfonic acid, p-toluenesulfonic acid, naphthalenedisulfonic acid, polygalacturonic acid, and the like; and (d) salts formed from elemental anions such as chlorine, bromine, and iodine.

The antisense compounds of the present invention can be utilized for diagnostics, therapeutics, prophylaxis and as research reagents and kits. For therapeutics, an animal, preferably a human, suspected of having a disease or disorder which can be treated by modulating the expression of apolipoprotein B is treated by administering antisense compounds in accordance with this invention. The compounds of the invention can be utilized in pharmaceutical compositions by adding an effective amount of an antisense compound to a suitable pharmaceutically acceptable diluent or carrier. Use of the antisense compounds and methods of the invention may also be useful prophylactically, e.g., to prevent or delay infection, inflammation or tumor formation, for example.

The antisense compounds of the invention are useful for research and diagnostics, because these compounds hybridize to nucleic acids encoding apolipoprotein B, enabling sandwich and other assays to easily be constructed to exploit this fact. Hybridization of the antisense oligonucleotides of the invention with a nucleic acid encoding apolipoprotein B can be detected by means known in the art. Such means may include conjugation of an enzyme to the oligonucleotide, radiolabelling of the oligonucleotide or any other suitable detection means. Kits using such detection means for detecting the level of apolipoprotein B in a sample may also be prepared.

The present invention also includes pharmaceutical compositions and formulations which include the antisense compounds of the invention. The pharmaceutical compositions of the present invention may be administered in a number of ways depending upon whether local or systemic treatment is desired and upon the area to be treated. Administration may be topical (including ophthalmic and to mucous membranes including vaginal and rectal delivery), pulmonary, e.g., by inhalation or insufflation of powders or aerosols, including by nebulizer; intratracheal, intranasal, epidermal and transdermal), oral or parenteral. Parenteral administration includes intravenous, intraarterial, subcutaneous, intraperitoneal or intramuscular injection or infusion; or intracranial, e.g., intrathecal or intraventricular, administration. Oligonucleotides with at least one 2'-O-methoxyethyl modification are believed to be particularly useful for oral administration.

Pharmaceutical compositions and formulations for topical administration may include transdermal patches, ointments, lotions, creams, gels, drops, suppositories, sprays, liquids and powders. Conventional pharmaceutical carriers, aqueous, powder or oily bases, thickeners and the like may be necessary or desirable. Coated condoms, gloves and the like may also be useful. Preferred topical formulations include those in which the oligonucleotides of the invention are in admixture with a topical delivery agent such as lipids, liposomes, fatty acids, fatty acid esters, steroids, chelating agents and surfactants. Preferred lipids and liposomes include neutral (e.g. dioleoylphosphatidyl DOPE ethanolamine, dimyristoylphosphatidyl choline DMPC, distearolyphosphatidyl choline) negative (e.g. dimyristoylphosphatidyl glycerol DMPG) and cationic (e.g. dioleoyltetramethylaminopropyl DOTAP and dioleoylphosphatidyl ethanolamine DOTMA). Oligonucleotides of the invention may be encapsulated within liposomes or may form complexes thereto, in particular to cationic liposomes. Alternatively, oligonucleotides may be complexed to lipids, in particular to cationic lipids. Preferred fatty acids and esters include but are not limited arachidonic acid, oleic acid, eicosanoic acid, lauric acid, caprylic acid, capric acid, myristic acid, palmitic acid, stearic acid, linoleic acid, linolenic acid, dicaprate, tricaprate, monoolein, dilaurin, glyceryl 1-monocaprate, 1-dodecylazacycloheptan-2-one, an acylcarnitine, an acylcholine, or a $C_{1-10}$ alkyl ester (e.g. isopropylmyristate IPM), monoglyceride, diglyceride or pharmaceutically acceptable salt thereof. Topical formulations are described in detail in U.S. patent application Ser. No. 09/315,298 filed on May 20, 1999 which is incorporated herein by reference in its entirety.

Compositions and formulations for oral administration include powders or granules, microparticulates, nanoparticulates, suspensions or solutions in water or non-aqueous media, capsules, gel capsules, sachets, tablets or minitablets. Thickeners, flavoring agents, diluents, emulsifiers, dispersing aids or binders may be desirable. Preferred oral formulations are those in which oligonucleotides of the invention are administered in conjunction with one or more penetration enhancers surfactants and chelators. Preferred surfactants include fatty acids and/or esters or salts thereof, bile acids and/or salts thereof. Preferred bile acids/salts include chenodeoxycholic acid (CDCA) and ursodeoxychenodeoxycholic acid (UDCA), cholic acid, dehydrocholic acid, deoxycholic acid, glucholic acid, glycholic acid, glycodeoxycholic acid, taurocholic acid, taurodeoxycholic acid, sodium tauro-24,25-dihydro-fusidate, sodium glycodihydrofusidate. Preferred fatty acids include arachidonic acid, undecanoic acid, oleic acid, lauric acid, caprylic acid, capric acid, myristic acid, palmitic acid, stearic acid, linoleic acid, linolenic acid, dicaprate, tricaprate, monoolein, dilaurin, glyceryl 1-monocaprate, 1-dodecylazacycloheptan-2-one, an acylcarnitine, an acylcholine, or a monoglyceride, a diglyceride or a pharmaceutically acceptable salt thereof (e.g. sodium). Also preferred are combinations of penetration enhancers, for example, fatty acids/salts in combination with bile acids/salts. A particularly preferred combination is the sodium salt of lauric acid, capric acid and UDCA. Further penetration enhancers include polyoxyethylene-9-lauryl ether, polyoxyethylene-20-cetyl ether. Oligonucleotides of the invention may be delivered orally in granular form including sprayed dried particles, or complexed to form micro or nanoparticles. Oligonucleotide complexing agents include poly-amino acids; polyimines; polyacrylates; polyalkylacrylates, polyoxethanes, polyalkylcyanoacrylates; cationized gelatins, albumins, starches, acrylates, polyethyleneglycols (PEG) and starches; polyalkylcyanoacrylates; DEAE-derivatized polyimines, pollulans, celluloses and starches. Particularly preferred complexing agents include chitosan, N-trimethylchitosan, poly-L-lysine, polyhistidine, polyornithine, polyspermines, protamine, polyvinylpyridine, polythiodiethylamino-methylethylene P (TDAE), polyaminostyrene (e.g. p-amino), poly(methylcyanoacrylate), poly(ethylcyanoacrylate), poly(butylcyanoacrylate), poly(isobutylcyanoacrylate), poly(isohexylcynaoacrylate), DEAE-methacrylate, DEAE-hexylacrylate, DEAE-acrylamide, DEAE-albumin and DEAE-dextran, polymethylacrylate, polyhexylacrylate, poly(D,L-lactic acid), poly(DL-lactic-co-glycolic acid (PLGA), alginate, and polyethyleneglycol (PEG). Oral formulations for oligonucleotides and their preparation are described in detail in U.S. application Ser. Nos. 08/886,829 (filed Jul. 1, 1997), 09/108,673 (filed Jul. 1, 1998), 09/256,515 (filed Feb. 23, 1999), 09/082,624 (filed May 21, 1998) and 09/315,298 (filed May 20, 1999) each of which is incorporated herein by reference in their entirety.

Compositions and formulations for parenteral, intrathecal or intraventricular administration may include sterile aqueous solutions which may also contain buffers, diluents and other suitable additives such as, but not limited to, penetration enhancers, carrier compounds and other pharmaceutically acceptable carriers or excipients.

Pharmaceutical compositions of the present invention include, but are not limited to, solutions, emulsions, and liposome-containing formulations. These compositions may be generated from a variety of components that include, but are not limited to, preformed liquids, self-emulsifying solids and self-emulsifying semisolids.

The pharmaceutical formulations of the present invention, which may conveniently be presented in unit dosage form, may be prepared according to conventional techniques well known in the pharmaceutical industry. Such techniques include the step of bringing into association the active ingredients with the pharmaceutical carrier(s) or excipient(s). In general the formulations are prepared by uniformly and intimately bringing into association the active ingredients with liquid carriers or finely divided solid carriers or both, and then, if necessary, shaping the product.

The compositions of the present invention may be formulated into any of many possible dosage forms such as, but not limited to, tablets, capsules, gel capsules, liquid syrups, soft gels, suppositories, and enemas. The compositions of the present invention may also be formulated as suspensions in aqueous, non-aqueous or mixed media. Aqueous suspensions may further contain substances which increase the viscosity of the suspension including, for example, sodium carboxymethylcellulose, sorbitol and/or dextran. The suspension may also contain stabilizers.

In one embodiment of the present invention the pharmaceutical compositions may be formulated and used as foams. Pharmaceutical foams include formulations such as, but not limited to, emulsions, microemulsions, creams, jellies and liposomes. While basically similar in nature these formulations vary in the components and the consistency of the final product. The preparation of such compositions and formulations is generally known to those skilled in the pharmaceutical and formulation arts and may be applied to the formulation of the compositions of the present invention.

Emulsions

The compositions of the present invention may be prepared and formulated as emulsions. Emulsions are typically heterogenous systems of one liquid dispersed in another in the form of droplets usually exceeding 0.1 μm in diameter (Idson, in *Pharmaceutical Dosage Forms*, Lieberman, Rieger and Banker (Eds.), 1988, Marcel Dekker, Inc., New York, N.Y., volume 1, p. 199; Rosoff, in *Pharmaceutical Dosage Forms*, Lieberman, Rieger and Banker (Eds.), 1988, Marcel Dekker, Inc., New York, N.Y., Volume 1, p. 245; Block in *Pharmaceutical Dosage Forms*, Lieberman, Rieger and Banker (Eds.), 1988, Marcel Dekker, Inc., New York, N.Y., volume 2, p. 335; Higuchi et al., in *Remington's Pharmaceutical Sciences*, Mack Publishing Co., Easton, Pa., 1985, p. 301). Emulsions are often biphasic systems comprising of two immiscible liquid phases intimately mixed and dispersed with each other. In general, emulsions may be either water-in-oil (w/o) or of the oil-in-water (o/w) variety. When an aqueous phase is finely divided into and dispersed as minute droplets into a bulk oily phase the resulting composition is called a water-in-oil (w/o) emulsion. Alternatively, when an oily phase is finely divided into and dispersed as minute droplets into a bulk aqueous phase the resulting composition is called an oil-in-water (o/w) emulsion. Emulsions may contain additional components in addition to the dispersed phases and the active drug which may be present as a solution in either the aqueous phase, oily phase or itself as a separate phase. Pharmaceutical excipients such as emulsifiers, stabilizers, dyes, and anti-oxidants may also be present in emulsions as needed. Pharmaceutical emulsions may also be multiple emulsions that are comprised of more than two phases such as, for example, in the case of oil-in-water-in-oil (o/w/o) and water-in-oil-in-water (w/o/w) emulsions. Such complex formulations often provide certain advantages that simple binary emulsions do not. Multiple emulsions in which individual oil droplets of an o/w emulsion enclose small water droplets constitute a w/o/w emulsion. Likewise a system of oil droplets enclosed in globules of water stabilized in an oily continuous provides an o/w/o emulsion.

Emulsions are characterized by little or no thermodynamic stability. Often, the dispersed or discontinuous phase of the emulsion is well dispersed into the external or continuous phase and maintained in this form through the means of emulsifiers or the viscosity of the formulation. Either of the phases of the emulsion may be a semisolid or a solid, as is the case of emulsion-style ointment bases and creams. Other means of stabilizing emulsions entail the use of emulsifiers that may be incorporated into either phase of the emulsion. Emulsifiers may broadly be classified into four categories: synthetic surfactants, naturally occurring emulsifiers, absorption bases, and finely dispersed solids (Idson, in *Pharmaceutical Dosage Forms*, Lieberman, Rieger and Banker (Eds.), 1988, Marcel Dekker, Inc., New York, N.Y., volume 1, p. 199).

Synthetic surfactants, also known as surface active agents, have found wide applicability in the formulation of emulsions and have been reviewed in the literature (Rieger, in *Pharmaceutical Dosage Forms*, Lieberman, Rieger and Banker (Eds.), 1988, Marcel Dekker, Inc., New York, N.Y., volume 1, p. 285; Idson, in *Pharmaceutical Dosage Forms*, Lieberman, Rieger and Banker (Eds.), Marcel Dekker, Inc., New York, N.Y., 1988, volume 1, p. 199). Surfactants are typically amphiphilic and comprise a hydrophilic and a hydrophobic portion. The ratio of the hydrophilic to the hydrophobic nature of the surfactant has been termed the hydrophile/lipophile balance (HLB) and is a valuable tool in categorizing and selecting surfactants in the preparation of formulations. Surfactants may be classified into different classes based on the nature of the hydrophilic group: nonionic, anionic, cationic and amphoteric (Rieger, in *Pharmaceutical Dosage Forms*, Lieberman, Rieger and Banker (Eds.), 1988, Marcel Dekker, Inc., New York, N.Y., volume 1, p. 285).

Naturally occurring emulsifiers used in emulsion formulations include lanolin, beeswax, phosphatides, lecithin and acacia. Absorption bases possess hydrophilic properties such that they can soak up water to form w/o emulsions yet retain their semisolid consistencies, such as anhydrous lanolin and hydrophilic petrolatum. Finely divided solids have also been used as good emulsifiers especially in combination with surfactants and in viscous preparations. These include polar inorganic solids, such as heavy metal hydroxides, nonswelling clays such as bentonite, attapulgite, hectorite, kaolin, montmorillonite, colloidal aluminum silicate and colloidal magnesium aluminum silicate, pigments and nonpolar solids such as carbon or glyceryl tristearate.

A large variety of non-emulsifying materials are also included in emulsion formulations and contribute to the properties of emulsions. These include fats, oils, waxes, fatty acids, fatty alcohols, fatty esters, humectants, hydrophilic colloids, preservatives and antioxidants (Block, in *Pharmaceutical Dosage Forms*, Lieberman, Rieger and Banker (Eds.), 1988, Marcel Dekker, Inc., New York, N.Y., volume 1, p. 335; Idson, in *Pharmaceutical Dosage Forms*, Lieberman, Rieger and Banker (Eds.), 1988, Marcel Dekker, Inc., New York, N.Y., volume 1, p. 199).

Hydrophilic colloids or hydrocolloids include naturally occurring gums and synthetic polymers such as polysaccharides (for example, acacia, agar, alginic acid, carrageenan, guar gum, karaya gum, and tragacanth), cellulose derivatives (for example, carboxymethylcellulose and carboxypropylcellulose), and synthetic polymers (for example, carbomers, cellulose ethers, and carboxyvinyl polymers). These disperse or swell in water to form colloidal solutions that stabilize emulsions by forming strong interfacial films around the dispersed-phase droplets and by increasing the viscosity of the external phase.

Since emulsions often contain a number of ingredients such as carbohydrates, proteins, sterols and phosphatides that may readily support the growth of microbes, these formulations often incorporate preservatives. Commonly used preservatives included in emulsion formulations include methyl paraben, propyl paraben, quaternary ammonium salts, benzalkonium chloride, esters of p-hydroxybenzoic acid, and boric acid. Antioxidants are also commonly added to emulsion formulations to prevent deterioration of the formulation. Antioxidants used may be free radical scavengers such as tocopherols, alkyl gallates, butylated hydroxyanisole, butylated hydroxytoluene, or reducing agents such as ascorbic acid and sodium metabisulfite, and antioxidant synergists such as citric acid, tartaric acid, and lecithin.

The application of emulsion formulations via dermatological, oral and parenteral routes and methods for their manufacture have been reviewed in the literature (Idson, in *Pharmaceutical Dosage Forms*, Lieberman, Rieger and Banker (Eds.), 1988, Marcel Dekker, Inc., New York, N.Y., volume 1, p. 199). Emulsion formulations for oral delivery have been very widely used because of reasons of ease of formulation, efficacy from an absorption and bioavailability standpoint. (Rosoff, in *Pharmaceutical Dosage Forms*, Lieberman, Rieger and Banker (Eds.), 1988, Marcel Dekker, Inc., New York, N.Y., volume 1, p. 245; Idson, in *Pharmaceutical Dosage Forms*, Lieberman, Rieger and Banker (Eds.), 1988, Marcel Dekker, Inc., New York, N.Y., volume 1, p. 199). Mineral-oil base laxatives, oil-soluble vitamins and high fat nutritive preparations are among the materials that have commonly been administered orally as o/w emulsions.

In one embodiment of the present invention, the compositions of oligonucleotides and nucleic acids are formulated as microemulsions. A microemulsion may be defined as a system of water, oil and amphiphile which is a single optically isotropic and thermodynamically stable liquid solution (Rosoff, in *Pharmaceutical Dosage Forms*, Lieberman, Rieger and Banker (Eds.), 1988, Marcel Dekker, Inc., New York, N.Y., volume 1, p. 245). Typically microemulsions are systems that are prepared by first dispersing an oil in an aqueous surfactant solution and then adding a sufficient amount of a fourth component, generally an intermediate chain-length alcohol to form a transparent system. Therefore, microemulsions have also been described as thermodynamically stable, isotropically clear dispersions of two immiscible liquids that are stabilized by interfacial films of surface-active molecules (Leung and Shah, in: *Controlled Release of Drugs: Polymers and Aggregate Systems*, Rosoff, M., Ed., 1989, VCH Publishers, New York, pages 185-215). Microemulsions commonly are prepared via a combination of three to five components that include oil, water, surfactant, cosurfactant and electrolyte. Whether the microemulsion is of the water-in-oil (w/o) or an oil-in-water (o/w) type is dependent on the properties of the oil and surfactant used and on the structure and geometric packing of the polar heads and hydrocarbon tails of the surfactant molecules (Schott, in *Remington's Pharmaceutical Sciences*, Mack Publishing Co., Easton, Pa., 1985, p. 271).

The phenomenological approach utilizing phase diagrams has been extensively studied and has yielded a comprehensive knowledge, to one skilled in the art, of how to formulate microemulsions (Rosoff, in *Pharmaceutical Dosage Forms*, Lieberman, Rieger and Banker (Eds.), 1988, Marcel Dekker, Inc., New York, N.Y., volume 1, p. 245; Block, in *Pharmaceutical Dosage Forms*, Lieberman, Rieger and Banker (Eds.), 1988, Marcel Dekker, Inc., New York, N.Y., volume 1, p. 335). Compared to conventional emulsions, microemulsions offer the advantage of solubilizing water-insoluble drugs in a formulation of thermodynamically stable droplets that are formed spontaneously.

Surfactants used in the preparation of microemulsions include, but are not limited to, ionic surfactants, non-ionic surfactants, Brij 96, polyoxyethylene oleyl ethers, polyglycerol fatty acid esters, tetraglycerol monolaurate (ML310), tetraglycerol monooleate (MO310), hexaglycerol monooleate (PO310), hexaglycerol pentaoleate (PO500), decaglycerol monocaprate (MCA750), decaglycerol monooleate (MO750), decaglycerol sequioleate (SO750), decaglycerol decaoleate (DAO750), alone or in combination with cosurfactants. The cosurfactant, usually a short-chain alcohol such as ethanol, 1-propanol, and 1-butanol, serves to increase the interfacial fluidity by penetrating into the surfactant film and consequently creating a disordered film because of the void space generated among surfactant molecules. Microemulsions may, however, be prepared without the use of cosurfactants and alcohol-free self-emulsifying microemulsion systems are known in the art. The aqueous phase may typically be, but is not limited to, water, an aqueous solution of the drug, glycerol, PEG300, PEG400, polyglycerols, propylene glycols, and derivatives of ethylene glycol. The oil phase may include, but is not limited to, materials such as Captex 300, Captex 355, Capmul MCM, fatty acid esters, medium chain (C8-C12) mono, di, and tri-glycerides, polyoxyethylated glyceryl fatty acid esters, fatty alcohols, polyglycolized glycerides, saturated polyglycolized C8-C10 glycerides, vegetable oils and silicone oil.

Microemulsions are particularly of interest from the standpoint of drug solubilization and the enhanced absorption of drugs. Lipid based microemulsions (both o/w and w/o) have been proposed to enhance the oral bioavailability of drugs, including peptides (Constantinides et al., *Pharmaceutical Research*, 1994, 11, 1385-1390; Ritschel, *Meth. Find. Exp. Clin. Pharmacol.*, 1993, 13, 205). Microemulsions afford advantages of improved drug solubilization, protection of drug from enzymatic hydrolysis, possible enhancement of drug absorption due to surfactant-induced alterations in membrane fluidity and permeability, ease of preparation, ease of oral administration over solid dosage forms, improved clinical potency, and decreased toxicity (Constantinides et al., *Pharmaceutical Research*, 1994, 11, 1385; Ho et al., *J. Pharm. Sci.*, 1996, 85, 138-143). Often microemulsions may form spontaneously when their components are brought together at ambient temperature. This may be particularly advantageous when formulating thermolabile drugs, peptides or oligonucleotides. Microemulsions have also been effective in the transdermal delivery of active components in both cosmetic and pharmaceutical applications. It is expected that the microemulsion compositions and formulations of the present invention will facilitate the increased systemic absorption of oligonucleotides and nucleic acids from the gastrointestinal tract, as well as improve the local cellular uptake of oligonucleotides and nucleic acids within the gastrointestinal tract, vagina, buccal cavity and other areas of administration.

Microemulsions of the present invention may also contain additional components and additives such as sorbitan monostearate (Grill 3), Labrasol, and penetration enhancers to improve the properties of the formulation and to enhance the absorption of the oligonucleotides and nucleic acids of the present invention. Penetration enhancers used in the microemulsions of the present invention may be classified as belonging to one of five broad categories—surfactants, fatty acids, bile salts, chelating agents, and non-chelating non-surfactants (Lee et al., *Critical Reviews in Therapeutic Drug Carrier Systems*, 1991, p. 92). Each of these classes has been discussed above.

Liposomes

There are many organized surfactant structures besides microemulsions that have been studied and used for the formulation of drugs. These include monolayers, micelles, bilayers and vesicles. Vesicles, such as liposomes, have attracted great interest because of their specificity and the duration of action they offer from the standpoint of drug delivery. As used in the present invention, the term "liposome" means a vesicle composed of amphiphilic lipids arranged in a spherical bilayer or bilayers.

Liposomes are unilamellar or multilamellar vesicles which have a membrane formed from a lipophilic material and an aqueous interior. The aqueous portion contains the composition to be delivered. Cationic liposomes possess the advantage of being able to fuse to the cell wall. Non-cationic liposomes, although not able to fuse as efficiently with the cell wall, are taken up by macrophages in vivo.

In order to cross intact mammalian skin, lipid vesicles must pass through a series of fine pores, each with a diameter less than 50 nm, under the influence of a suitable transdermal gradient. Therefore, it is desirable to use a liposome which is highly deformable and able to pass through such fine pores.

Further advantages of liposomes include; liposomes obtained from natural phospholipids are biocompatible and biodegradable; liposomes can incorporate a wide range of water and lipid soluble drugs; liposomes can protect encapsulated drugs in their internal compartments from metabolism and degradation (Rosoff, in *Pharmaceutical Dosage Forms*, Lieberman, Rieger and Banker (Eds.), 1988, Marcel Dekker, Inc., New York, N.Y., volume 1, p. 245). Important considerations in the preparation of liposome formulations are the lipid surface charge, vesicle size and the aqueous volume of the liposomes.

Liposomes are useful for the transfer and delivery of active ingredients to the site of action. Because the liposomal membrane is structurally similar to biological membranes, when liposomes are applied to a tissue, the liposomes start to merge with the cellular membranes. As the merging of the liposome and cell progresses, the liposomal contents are emptied into the cell where the active agent may act.

Liposomal formulations have been the focus of extensive investigation as the mode of delivery for many drugs. There is growing evidence that for topical administration, liposomes present several advantages over other formulations. Such advantages include reduced side-effects related to high systemic absorption of the administered drug, increased accumulation of the administered drug at the desired target, and the ability to administer a wide variety of drugs, both hydrophilic and hydrophobic, into the skin.

Several reports have detailed the ability of liposomes to deliver agents including high-molecular weight DNA into the skin. Compounds including analgesics, antibodies, hormones and high-molecular weight DNAs have been administered to the skin. The majority of applications resulted in the targeting of the upper epidermis.

Liposomes fall into two broad classes. Cationic liposomes are positively charged liposomes which interact with the negatively charged DNA molecules to form a stable complex. The positively charged DNA/liposome complex binds to the negatively charged cell surface and is internalized in an endosome. Due to the acidic pH within the endosome, the liposomes are ruptured, releasing their contents into the cell cytoplasm (Wang et al., *Biochem. Biophys. Res. Commun.*, 1987, 147, 980-985).

Liposomes which are pH-sensitive or negatively-charged, entrap DNA rather than complex with it. Since both the DNA and the lipid are similarly charged, repulsion rather than complex formation occurs. Nevertheless, some DNA is entrapped within the aqueous interior of these liposomes. pH-sensitive liposomes have been used to deliver DNA encoding the thymidine kinase gene to cell monolayers in culture. Expression of the exogenous gene was detected in the target cells (Zhou et al., *Journal of Controlled Release*, 1992, 19, 269-274).

One major type of liposomal composition includes phospholipids other than naturally-derived phosphatidylcholine. Neutral liposome compositions, for example, can be formed from dimyristoyl phosphatidylcholine (DMPC) or dipalmitoyl phosphatidylcholine (DPPC). Anionic liposome compositions generally are formed from dimyristoyl phosphatidylglycerol, while anionic fusogenic liposomes are formed primarily from dioleoyl phosphatidylethanolamine (DOPE). Another type of liposomal composition is formed from phosphatidylcholine (PC) such as, for example, soybean PC, and egg PC. Another type is formed from mixtures of phospholipid and/or phosphatidylcholine and/or cholesterol.

Several studies have assessed the topical delivery of liposomal drug formulations to the skin. Application of liposomes containing interferon to guinea pig skin resulted in a reduction of skin herpes sores while delivery of interferon via other means (e.g. as a solution or as an emulsion) were ineffective (Weiner et al., *Journal of Drug Targeting*, 1992, 2, 405-410). Further, an additional study tested the efficacy of interferon administered as part of a liposomal formulation to the administration of interferon using an aqueous system, and concluded that the liposomal formulation was superior to aqueous administration (du Plessis et al., *Antiviral Research*, 1992, 18, 259-265).

Non-ionic liposomal systems have also been examined to determine their utility in the delivery of drugs to the skin, in particular systems comprising non-ionic surfactant and cholesterol. Non-ionic liposomal formulations comprising Novasome™ I (glyceryl dilaurate/cholesterol/polyoxyethylene-10-stearyl ether) and Novasome™ II (glyceryl distearate/cholesterol/polyoxyethylene-10-stearyl ether) were used to deliver cyclosporin-A into the dermis of mouse skin. Results indicated that such non-ionic liposomal systems were effective in facilitating the deposition of cyclosporin-A into different layers of the skin (Hu et al. *S.T.P. Pharma. Sci.*, 1994, 4, 6, 466).

Liposomes also include "sterically stabilized" liposomes, a term which, as used herein, refers to liposomes comprising one or more specialized lipids that, when incorporated into liposomes, result in enhanced circulation lifetimes relative to liposomes lacking such specialized lipids. Examples of sterically stabilized liposomes are those in which part of the vesicle-forming lipid portion of the liposome (A) comprises one or more glycolipids, such as monosialoganglioside $G_{M1}$, or (B) is derivatized with one or more hydrophilic polymers, such as a polyethylene glycol (PEG) moiety. While not wishing to be bound by any particular theory, it is thought in the art that, at least for sterically stabilized liposomes containing gangliosides, sphingomyelin, or PEG-derivatized lipids, the enhanced circulation half-life of these sterically stabilized liposomes derives from a reduced uptake into cells of the reticuloendothelial system (RES) (Allen et al., *FEBS Letters*, 1987, 223, 42; Wu et al., *Cancer Research*, 1993, 53, 3765). Various liposomes comprising one or more glycolipids are known in the art. Papahadjopoulos et al. (*Ann. N.Y. Acad. Sci.*, 1987, 507, 64) reported the ability of monosialoganglioside $G_{M1}$, galactocerebroside sulfate and phosphatidylinositol to improve blood half-lives of liposomes. These findings were expounded upon by Gabizon et al. (*Proc. Natl. Acad. Sci. U.S.A.*, 1988, 85, 6949). U.S. Pat. No. 4,837,028 and WO 88/04924, both to Allen et al., disclose liposomes comprising (1) sphingomyelin and (2) the ganglioside $G_{M1}$ or a galactocerebroside sulfate ester. U.S. Pat. No. 5,543,152 (Webb et al.) discloses liposomes comprising sphingomyelin. Liposomes comprising 1,2-sn-dimyristoylphosphatidylcholine are disclosed in WO 97/13499 (Lim et al.).

Many liposomes comprising lipids derivatized with one or more hydrophilic polymers, and methods of preparation thereof, are known in the art. Sunamoto et al. (*Bull. Chem. Soc. Jpn.*, 1980, 53, 2778) described liposomes comprising a nonionic detergent, $2C_{12}15G$, that contains a PEG moiety. Illum et al. (*FEBS Lett.*, 1984, 167, 79) noted that hydrophilic coating of polystyrene particles with polymeric glycols results in significantly enhanced blood half-lives. Synthetic phospholipids modified by the attachment of carboxylic groups of polyalkylene glycols (e.g., PEG) are described by Sears (U.S. Pat. Nos. 4,426,330 and 4,534,899). Klibanov et al. (*FEBS Lett.*, 1990, 268, 235) described experiments demonstrating that liposomes comprising phosphatidylethanolamine (PE) derivatized with PEG or PEG stearate have significant increases in blood circulation half-lives. Blume et al. (*Biochimica et Biophysica Acta*, 1990, 1029, 91) extended such observations to other PEG-derivatized phospholipids, e.g., DSPE-PEG, formed from the combination of distearoylphosphatidylethanolamine (DSPE) and PEG. Liposomes having covalently bound PEG moieties on their external surface are described in European Patent No. EP 0 445 131 B1 and WO 90/04384 to Fisher. Liposome compositions containing 1-20 mole percent of PE derivatized with PEG, and methods of use thereof, are described by Woodle et al. (U.S. Pat. Nos. 5,013,556 and 5,356,633) and Martin et al. (U.S. Pat. No. 5,213,804 and European Patent No. EP 0 496 813 B1). Liposomes comprising a number of other lipid-polymer conjugates are disclosed in WO 91/05545 and U.S. Pat. No. 5,225,212 (both to Martin et al.) and in WO 94/20073 (Zalipsky et al.) Liposomes comprising PEG-modified ceramide lipids are described in WO 96/10391 (Choi et al.). U.S. Pat. No. 5,540,935 (Miyazaki et al.) and U.S. Pat. No. 5,556,948 (Tagawa et al.) describe PEG-containing liposomes that can be further derivatized with functional moieties on their surfaces.

A limited number of liposomes comprising nucleic acids are known in the art. WO 96/40062 to Thierry et al. discloses methods for encapsulating high molecular weight nucleic acids in liposomes. U.S. Pat. No. 5,264,221 to Tagawa et al. discloses protein-bonded liposomes and asserts that the contents of such liposomes may include an antisense RNA. U.S. Pat. No. 5,665,710 to Rahman et al. describes certain methods of encapsulating oligodeoxynucleotides in liposomes. WO 97/04787 to Love et al. discloses liposomes comprising antisense oligonucleotides targeted to the raf gene.

Transfersomes are yet another type of liposomes, and are highly deformable lipid aggregates which are attractive candidates for drug delivery vehicles. Transfersomes may be described as lipid droplets which are so highly deformable that they are easily able to penetrate through pores which are smaller than the droplet. Transfersomes are adaptable to the environment in which they are used, e.g. they are self-optimizing (adaptive to the shape of pores in the skin), self-repairing, frequently reach their targets without fragmenting, and often self-loading. To make transfersomes it is possible to add surface edge-activators, usually surfactants, to a standard liposomal composition. Transfersomes have been used to deliver serum albumin to the skin. The transfersome-mediated delivery of serum albumin has been shown to be as effective as subcutaneous injection of a solution containing serum albumin.

Surfactants find wide application in formulations such as emulsions (including microemulsions) and liposomes. The most common way of classifying and ranking the properties of the many different types of surfactants, both natural and synthetic, is by the use of the hydrophile/lipophile balance (HLB). The nature of the hydrophilic group (also known as the "head") provides the most useful means for categorizing the different surfactants used in formulations (Rieger, in *Pharmaceutical Dosage Forms*, Marcel Dekker, Inc., New York, N.Y., 1988, p. 285).

If the surfactant molecule is not ionized, it is classified as a nonionic surfactant. Nonionic surfactants find wide application in pharmaceutical and cosmetic products and are usable over a wide range of pH values. In general their HLB values range from 2 to about 18 depending on their structure. Nonionic surfactants include nonionic esters such as ethylene glycol esters, propylene glycol esters, glyceryl esters, polyglyceryl esters, sorbitan esters, sucrose esters, and ethoxylated esters. Nonionic alkanolamides and ethers such as fatty alcohol ethoxylates, propoxylated alcohols, and ethoxylated/propoxylated block polymers are also included in this class. The polyoxyethylene surfactants are the most popular members of the nonionic surfactant class.

If the surfactant molecule carries a negative charge when it is dissolved or dispersed in water, the surfactant is classified as anionic. Anionic surfactants include carboxylates such as soaps, acyl lactylates, acyl amides of amino acids, esters of sulfuric acid such as alkyl sulfates and ethoxylated alkyl sulfates, sulfonates such as alkyl benzene sulfonates, acyl isethionates, acyl taurates and sulfosuccinates, and phosphates. The most important members of the anionic surfactant class are the alkyl sulfates and the soaps.

If the surfactant molecule carries a positive charge when it is dissolved or dispersed in water, the surfactant is classified as cationic. Cationic surfactants include quaternary ammonium salts and ethoxylated amines. The quaternary ammonium salts are the most used members of this class.

If the surfactant molecule has the ability to carry either a positive or negative charge, the surfactant is classified as amphoteric. Amphoteric surfactants include acrylic acid derivatives, substituted alkylamides, N-alkylbetaines and phosphatides.

The use of surfactants in drug products, formulations and in emulsions has been reviewed (Rieger, in *Pharmaceutical Dosage Forms*, Marcel Dekker, Inc., New York, N.Y., 1988, p. 285).

Penetration Enhancers

In one embodiment, the present invention employs various penetration enhancers to effect the efficient delivery of nucleic acids, particularly oligonucleotides, to the skin of animals. Most drugs are present in solution in both ionized and nonionized forms. However, usually only lipid soluble or lipophilic drugs readily cross cell membranes. It has been discovered that even non-lipophilic drugs may cross cell membranes if the membrane to be crossed is treated with a penetration enhancer. In addition to aiding the diffusion of non-lipophilic drugs across cell membranes, penetration enhancers also enhance the permeability of lipophilic drugs.

Penetration enhancers may be classified as belonging to one of five broad categories, i.e., surfactants, fatty acids, bile salts, chelating agents, and non-chelating non-surfactants (Lee et al., *Critical Reviews in Therapeutic Drug Carrier Systems*, 1991, p. 92). Each of the above mentioned classes of penetration enhancers are described below in greater detail.

Surfactants: In connection with the present invention, surfactants (or "surface-active agents") are chemical entities which, when dissolved in an aqueous solution, reduce the surface tension of the solution or the interfacial tension between the aqueous solution and another liquid, with the result that absorption of oligonucleotides through the mucosa is enhanced. In addition to bile salts and fatty acids, these penetration enhancers include, for example, sodium lauryl sulfate, polyoxyethylene-9-lauryl ether and polyoxyethylene-20-cetyl ether) (Lee et al., *Critical Reviews in Therapeutic Drug Carrier Systems*, 1991, p. 92); and perfluorochemical emulsions, such as FC-43. Takahashi et al., *J. Pharm. Pharmacol.*, 1988, 40, 252).

Fatty acids: Various fatty acids and their derivatives which act as penetration enhancers include, for example, oleic acid, lauric acid, capric acid (n-decanoic acid), myristic acid, palmitic acid, stearic acid, linoleic acid, linolenic acid, dicaprate, tricaprate, monoolein (1-monooleoyl-rac-glycerol), dilaurin, caprylic acid, arachidonic acid, glycerol 1-monocaprate, 1-dodecylazacycloheptan-2-one, acylcarnitines, acylcholines, $C_{1-10}$ alkyl esters thereof (e.g., methyl, isopropyl and t-butyl), and mono- and di-glycerides thereof (i.e., oleate, laurate, caprate, myristate, palmitate, stearate, linoleate, etc.) (Lee et al., *Critical Reviews in Therapeutic Drug Carrier Systems*, 1991, p. 92; Muranishi, *Critical Reviews in Therapeutic Drug Carrier Systems*, 1990, 7, 1-33; El Hariri et al., *J. Pharm. Pharmacol.*, 1992, 44, 651-654).

Bile salts: The physiological role of bile includes the facilitation of dispersion and absorption of lipids and fat-soluble vitamins (Brunton, Chapter 38 in: Goodman & Gilman's *The Pharmacological Basis of Therapeutics*, 9th Ed., Hardman et al. Eds., McGraw-Hill, New York, 1996, pp. 934-935). Various natural bile salts, and their synthetic derivatives, act as penetration enhancers. Thus the term "bile salts" includes any of the naturally occurring components of bile as well as any of their synthetic derivatives. The bile salts of the invention include, for example, cholic acid (or its pharmaceutically acceptable sodium salt, sodium cholate), dehydrocholic acid (sodium dehydrocholate), deoxycholic acid (sodium deoxycholate), glucholic acid (sodium glucholate), glycholic acid (sodium glycocholate), glycodeoxycholic acid (sodium glycodeoxycholate), taurocholic acid (sodium taurocholate), taurodeoxycholic acid (sodium taurodeoxycholate), chenodeoxycholic acid (sodium chenodeoxycholate), ursodeoxycholic acid (UDCA), sodium tauro-24,25-dihydro-fusidate (STDHF), sodium glycodihydrofusidate and polyoxyethylene-9-lauryl ether (POE) (Lee et al., *Critical Reviews in Therapeutic Drug Carrier Systems*, 1991, page 92; Swinyard, Chapter 39 In: *Remington's Pharmaceutical Sciences*, 18th Ed., Gennaro, ed., Mack Publishing Co., Easton, Pa., 1990, pages 782-783; Muranishi, *Critical Reviews in Therapeutic Drug Carrier Systems*, 1990, 7, 1-33; Yamamoto et al., *J. Pharm. Exp. Ther.*, 1992, 263, 25; Yamashita et al., *J. Pharm. Sci.*, 1990, 79, 579-583).

Chelating Agents: Chelating agents, as used in connection with the present invention, can be defined as compounds that remove metallic ions from solution by forming complexes therewith, with the result that absorption of oligonucleotides through the mucosa is enhanced. With regards to their use as penetration enhancers in the present invention, chelating agents have the added advantage of also serving as DNase inhibitors, as most characterized DNA nucleases require a divalent metal ion for catalysis and are thus inhibited by chelating agents (Jarrett, *J. Chromatogr.*, 1993, 618, 315-339). Chelating agents of the invention include but are not limited to disodium ethylenediaminetetraacetate (EDTA), citric acid, salicylates (e.g., sodium salicylate, 5-methoxysalicylate and homovanilate), N-acyl derivatives of collagen, laureth-9 and N-amino acyl derivatives of beta-diketones (enamines)(Lee et al., *Critical Reviews in Therapeutic Drug Carrier Systems*, 1991, page 92; Muranishi, *Critical Reviews in Therapeutic Drug Carrier Systems*, 1990, 7, 1-33; Buur et al., *J. Control Rel.*, 1990, 14, 43-51).

Non-chelating non-surfactants: As used herein, non-chelating non-surfactant penetration enhancing compounds can be defined as compounds that demonstrate insignificant activity as chelating agents or as surfactants but that nonetheless enhance absorption of oligonucleotides through the alimentary mucosa (Muranishi, *Critical Reviews in Therapeutic Drug Carrier Systems*, 1990, 7, 1-33). This class of penetration enhancers include, for example, unsaturated cyclic ureas, 1-alkyl- and 1-alkenylazacyclo-alkanone derivatives (Lee et al., *Critical Reviews in Therapeutic Drug Carrier Systems*, 1991, page 92); and non-steroidal anti-inflammatory agents such as diclofenac sodium, indomethacin and phenylbutazone (Yamashita et al., *J. Pharm. Pharmacol.*, 1987, 39, 621-626).

Agents that enhance uptake of oligonucleotides at the cellular level may also be added to the pharmaceutical and other compositions of the present invention. For example, cationic lipids, such as lipofectin (Junichi et al, U.S. Pat. No. 5,705, 188), cationic glycerol derivatives, and polycationic molecules, such as polylysine (Lollo et al., PCT Application WO 97/30731), are also known to enhance the cellular uptake of oligonucleotides.

Other agents may be utilized to enhance the penetration of the administered nucleic acids, including glycols such as ethylene glycol and propylene glycol, pyrrols such as 2-pyrrol, azones, and terpenes such as limonene and menthone.

Carriers

Certain compositions of the present invention also incorporate carrier compounds in the formulation. As used herein, "carrier compound" or "carrier" can refer to a nucleic acid, or analog thereof, which is inert (i.e., does not possess biological activity per se) but is recognized as a nucleic acid by in vivo processes that reduce the bioavailability of a nucleic acid having biological activity by, for example, degrading the biologically active nucleic acid or promoting its removal from circulation. The coadministration of a nucleic acid and a carrier compound, typically with an excess of the latter substance, can result in a substantial reduction of the amount of nucleic acid recovered in the liver, kidney or other extracirculatory reservoirs, presumably due to competition between the carrier compound and the nucleic acid for a common receptor. For example, the recovery of a partially phosphorothioate oligonucleotide in hepatic tissue can be reduced when it is coadministered with polyinosinic acid, dextran sulfate, polycytidic acid or 4-acetamido-4'isothiocyano-stilbene-2,2'-disulfonic acid (Miyao et al., *Antisense Res. Dev.*, 1995, 5, 115-121; Takakura et al., *Antisense & Nucl. Acid Drug Dev.*, 1996, 6, 177-183).

Excipients

In contrast to a carrier compound, a "pharmaceutical carrier" or "excipient" is a pharmaceutically acceptable solvent, suspending agent or any other pharmacologically inert vehicle for delivering one or more nucleic acids to an animal. The excipient may be liquid or solid and is selected, with the planned manner of administration in mind, so as to provide for the desired bulk, consistency, etc., when combined with a nucleic acid and the other components of a given pharmaceutical composition. Typical pharmaceutical carriers include, but are not limited to, binding agents (e.g., pregelatinized maize starch, polyvinylpyrrolidone or hydroxypropyl methylcellulose, etc.); fillers (e.g., lactose and other sugars, microcrystalline cellulose, pectin, gelatin, calcium sulfate, ethyl cellulose, polyacrylates or calcium hydrogen phosphate, etc.); lubricants (e.g., magnesium stearate, talc, silica, colloidal silicon dioxide, stearic acid, metallic stearates, hydrogenated vegetable oils, corn starch, polyethylene glycols, sodium benzoate, sodium acetate, etc.); disintegrants (e.g., starch, sodium starch glycolate, etc.); and wetting agents (e.g., sodium lauryl sulphate, etc.).

Pharmaceutically acceptable organic or inorganic excipient suitable for non-parenteral administration which do not deleteriously react with nucleic acids can also be used to formulate the compositions of the present invention. Suitable pharmaceutically acceptable carriers include, but are not limited to, water, salt solutions, alcohols, polyethylene glycols, gelatin, lactose, amylose, magnesium stearate, talc, silicic acid, viscous paraffin, hydroxymethylcellulose, polyvinylpyrrolidone and the like.

Formulations for topical administration of nucleic acids may include sterile and non-sterile aqueous solutions, non-aqueous solutions in common solvents such as alcohols, or solutions of the nucleic acids in liquid or solid oil bases. The solutions may also contain buffers, diluents and other suitable additives. Pharmaceutically acceptable organic or inorganic excipients suitable for non-parenteral administration which do not deleteriously react with nucleic acids can be used.

Suitable pharmaceutically acceptable excipients include, but are not limited to, water, salt solutions, alcohol, polyethylene glycols, gelatin, lactose, amylose, magnesium stearate, talc, silicic acid, viscous paraffin, hydroxymethylcellulose, polyvinylpyrrolidone and the like.

Other Components

The compositions of the present invention may additionally contain other adjunct components conventionally found in pharmaceutical compositions, at their art-established usage levels. Thus, for example, the compositions may contain additional, compatible, pharmaceutically-active materials such as, for example, antipruritics, astringents, local anesthetics or anti-inflammatory agents, or may contain additional materials useful in physically formulating various dosage forms of the compositions of the present invention, such as dyes, flavoring agents, preservatives, antioxidants, opacifiers, thickening agents and stabilizers. However, such materials, when added, should not unduly interfere with the biological activities of the components of the compositions of the present invention. The formulations can be sterilized and, if desired, mixed with auxiliary agents, e.g., lubricants, preservatives, stabilizers, wetting agents, emulsifiers, salts for influencing osmotic pressure, buffers, colorings, flavorings and/or aromatic substances and the like which do not deleteriously interact with the nucleic acid(s) of the formulation.

Aqueous suspensions may contain substances which increase the viscosity of the suspension including, for example, sodium carboxymethylcellulose, sorbitol and/or dextran. The suspension may also contain stabilizers.

Certain embodiments of the invention provide pharmaceutical compositions containing (a) one or more antisense compounds and (b) one or more other chemotherapeutic agents which function by a non-antisense mechanism. Examples of such chemotherapeutic agents include but are not limited to daunorubicin, daunomycin, dactinomycin, doxorubicin, epirubicin, idarubicin, esorubicin, bleomycin, mafosfamide, ifosfamide, cytosine arabinoside, bis-chloroethylnitrosurea, busulfan, mitomycin C, actinomycin D, mithramycin, prednisone, hydroxyprogesterone, testosterone, tamoxifen, dacarbazine, procarbazine, hexamethylmelamine, pentamethylmelamine, mitoxantrone, amsacrine, chlorambucil, methylcyclohexylnitrosurea, nitrogen mustards, melphalan, cyclophosphamide, 6-mercaptopurine, 6-thioguanine, cytarabine, 5-azacytidine, hydroxyurea, deoxycoformycin, 4-hydroxyperoxycyclophosphoramide, 5-fluorouracil (5-FU), 5-fluorodeoxyuridine (5-FUdR), methotrexate (MTX), colchicine, taxol, vincristine, vinblastine, etoposide (VP-16), trimetrexate, irinotecan, topotecan, gemcitabine, teniposide, cisplatin and diethylstilbestrol (DES). See, generally, *The Merck Manual of Diagnosis and Therapy*, 15th Ed. 1987, pp. 1206-1228, Berkow et al., eds., Rahway, N.J. When used with the compounds of the invention, such chemotherapeutic agents may be used individually (e.g., 5-FU and oligonucleotide), sequentially (e.g., 5-FU and oligonucleotide for a period of time followed by MTX and oligonucleotide), or in combination with one or more other such chemotherapeutic agents (e.g., 5-FU, MTX and oligonucleotide, or 5-FU, radiotherapy and oligonucleotide). Anti-inflammatory drugs, including but not limited to nonsteroidal anti-inflammatory drugs and corticosteroids, and antiviral drugs, including but not limited to ribivirin, vidarabine, acyclovir and ganciclovir, may also be combined in compositions of the invention. See, generally, *The Merck Manual of Diagnosis and Therapy*, 15th Ed., Berkow et al., eds., 1987, Rahway, N.J., pages 2499-2506 and 46-49, respectively). Other non-antisense chemotherapeutic agents are also within the scope of this invention. Two or more combined compounds may be used together or sequentially.

In another related embodiment, compositions of the invention may contain one or more antisense compounds, particularly oligonucleotides, targeted to a first nucleic acid and one or more additional antisense compounds targeted to a second nucleic acid target. Numerous examples of antisense compounds are known in the art. Two or more combined compounds may be used together or sequentially.

The formulation of therapeutic compositions and their subsequent administration is believed to be within the skill of those in the art. Dosing is dependent on severity and responsiveness of the disease state to be treated, with the course of treatment lasting from several days to several months, or until a cure is effected or a diminution of the disease state is achieved. Optimal dosing schedules can be calculated from measurements of drug accumulation in the body of the patient. Persons of ordinary skill can easily determine optimum dosages, dosing methodologies and repetition rates. Optimum dosages may vary depending on the relative potency of individual oligonucleotides, and can generally be estimated based on $EC_{50}$s found to be effective in in vitro and in vivo animal models. In general, dosage is from 0.01 ug to 100 g per kg of body weight, and may be given once or more daily, weekly, monthly or yearly, or even once every 2 to 20 years. Persons of ordinary skill in the art can easily estimate repetition rates for dosing based on measured residence times and concentrations of the drug in bodily fluids or tissues. Following successful treatment, it may be desirable to have the patient undergo maintenance therapy to prevent the recurrence of the disease state, wherein the oligonucleotide is administered in maintenance doses, ranging from 0.01 ug to 100 g per kg of body weight, once or more daily, to once every 20 years.

While the present invention has been described with specificity in accordance with certain of its preferred embodiments, the following examples serve only to illustrate the invention and are not intended to limit the same.

EXAMPLES

Example 1

Nucleoside Phosphoramidites for Oligonucleotide Synthesis Deoxy and 2'-alkoxy Amidites 2'-Deoxy and 2'-methoxy beta-cyanoethyldiisopropyl phosphoramidites were purchased from commercial sources (e.g. Chemgenes, Needham Mass. or Glen Research, Inc. Sterling Va.). Other 2'-O-alkoxy substituted nucleoside amidites are prepared as described in U.S. Pat. No. 5,506,351, herein incorporated by reference. For oligonucleotides synthesized using 2'-alkoxy amidites, the standard cycle for unmodified oligonucleotides was utilized, except the wait step after pulse delivery of tetrazole and base was increased to 360 seconds.

Oligonucleotides containing 5-methyl-2'-deoxycytidine (5-Me-C) nucleotides were synthesized according to published methods [Sanghvi, et. al., *Nucleic Acids Research*, 1993, 21, 3197-3203] using commercially available phosphoramidites (Glen Research, Sterling Va. or ChemGenes, Needham Mass.).

2'-Fluoro Amidites

2'-Fluorodeoxyadenosine Amidites

2'-fluoro oligonucleotides were synthesized as described previously [Kawasaki, et. al., *J. Med. Chem.*, 1993, 36, 831-841] and U.S. Pat. No. 5,670,633, herein incorporated by reference. Briefly, the protected nucleoside N6-benzoyl-2'-deoxy-2'-fluoroadenosine was synthesized utilizing commercially available 9-beta-D-arabinofuranosyladenine as starting material and by modifying literature procedures whereby the 2'-alpha-fluoro atom is introduced by a $S_N2$-displacement of a 2'-beta-trityl group. Thus N6-benzoyl-9-beta-D-arabinofuranosyladenine was selectively protected in moderate yield as the 3',5'-ditetrahydropyranyl (THP) intermediate. Deprotection of the THP and N6-benzoyl groups was accomplished using standard methodologies and standard methods were used to obtain the 5'-dimethoxytrityl-(DMT) and 5'-DMT-3'-phosphoramidite intermediates.

2'-Fluorodeoxyguanosine

The synthesis of 2'-deoxy-2'-fluoroguanosine was accomplished using tetraisopropyldisiloxanyl (TPDS) protected 9-beta-D-arabinofuranosylguanine as starting material, and conversion to the intermediate diisobutyryl-arabinofuranosylguanosine. Deprotection of the TPDS group was followed by protection of the hydroxyl group with THP to give diisobutyryl di-THP protected arabinofuranosylguanine. Selective O-deacylation and triflation was followed by treatment of the crude product with fluoride, then deprotection of the THP groups.

Standard methodologies were used to obtain the 5'-DMT- and 5'-DMT-3'-phosphoramidites.

2'-Fluorouridine

Synthesis of 2'-deoxy-2'-fluorouridine was accomplished by the modification of a literature procedure in which 2,2'-anhydro-1-beta-D-arabinofuranosyluracil was treated with 70% hydrogen fluoride-pyridine. Standard procedures were used to obtain the 5'-DMT and 5'-DMT-3'phosphoramidites.

2'-Fluorodeoxycytidine

2'-deoxy-2'-fluorocytidine was synthesized via amination of 2'-deoxy-2'-fluorouridine, followed by selective protection to give N4-benzoyl-2'-deoxy-2'-fluorocytidine. Standard procedures were used to obtain the 5'-DMT and 5'-DMT-3'phosphoramidites.

2'-O-(2-Methoxyethyl) Modified Amidites

2'-O-Methoxyethyl-substituted nucleoside amidites are prepared as follows, or alternatively, as per the methods of Martin, P., *Helvetica Chimica Acta*, 1995, 78, 486-504.

2,2'-Anhydro[1-(beta-D-arabinofuranosyl)-5-methyluridine]

5-Methyluridine (ribosylthymine, commercially available through Yamasa, Choshi, Japan) (72.0 g, 0.279 M), diphenylcarbonate (90.0 g, 0.420 M) and sodium bicarbonate (2.0 g, 0.024 M) were added to DMF (300 mL). The mixture was heated to reflux, with stirring, allowing the evolved carbon dioxide gas to be released in a controlled manner. After 1 hour, the slightly darkened solution was concentrated under reduced pressure. The resulting syrup was poured into diethylether (2.5 L), with stirring. The product formed a gum. The ether was decanted and the residue was dissolved in a minimum amount of methanol (ca. 400 mL). The solution was poured into fresh ether (2.5 L) to yield a stiff gum. The ether was decanted and the gum was dried in a vacuum oven (60° C. at 1 mm Hg for 24 h) to give a solid that was crushed to a light tan powder (57 g, 85% crude yield). The NMR spectrum was consistent with the structure, contaminated with phenol as its sodium salt (ca. 5%). The material was used as is for further reactions (or it can be purified further by column chromatography using a gradient of methanol in ethyl acetate (10-25%) to give a white solid, mp 222-4° C.)

2'-O-Methoxyethyl-5-methyluridine 2,2'-Anhydro-5-methyluridine (195 g, 0.81 M), tris(2-methoxyethyl)borate (231 g, 0.98 M) and 2-methoxyethanol (1.2 L) were added to a 2 L stainless steel pressure vessel and placed in a pre-heated oil bath at 160° C. After heating for 48 hours at 155-160° C., the vessel was opened and the solution evaporated to dryness and triturated with MeOH (200 mL). The residue was suspended in hot acetone (1 L). The insoluble salts were filtered, washed with acetone (150 mL) and the filtrate evaporated. The residue (280 g) was dissolved in $CH_3CN$ (600 mL) and evaporated. A silica gel column (3 kg) was packed in $CH_2Cl_2$/acetone/MeOH (20:5:3) containing 0.5% $Et_3NH$. The residue was dissolved in $CH_2Cl_2$ (250 mL) and adsorbed onto silica (150 g) prior to loading onto the column. The product was eluted with the packing solvent to give 160 g (63%) of product. Additional material was obtained by reworking impure fractions.

2'-O-Methoxyethyl-5'-O-dimethoxytrityl-5-methyluridine

2'-O-Methoxyethyl-5-methyluridine (160 g, 0.506 M) was co-evaporated with pyridine (250 mL) and the dried residue dissolved in pyridine (1.3 L). A first aliquot of dimethoxytrityl chloride (94.3 g, 0.278 M) was added and the mixture stirred at room temperature for one hour. A second aliquot of dimethoxytrityl chloride (94.3 g, 0.278 M) was added and the reaction stirred for an additional one hour. Methanol (170 mL) was then added to stop the reaction. HPLC showed the presence of approximately 70% product. The solvent was evaporated and triturated with $CH_3CN$ (200 mL). The residue was dissolved in $CHCl_3$ (1.5 L) and extracted with 2×500 mL of saturated $NaHCO_3$ and 2×500 mL of saturated NaCl. The organic phase was dried over $Na_2SO_4$, filtered and evaporated. 275 g of residue was obtained. The residue was purified on a 3.5 kg silica gel column, packed and eluted with EtOAc/hexane/acetone (5:5:1) containing 0.5% $Et_3NH$. The pure fractions were evaporated to give 164 g of product. Approximately 20 g additional was obtained from the impure fractions to give a total yield of 183 g (57%).

3'-O-Acetyl-2'-O-methoxyethyl-5'-O-dimethoxytrityl-5-methyluridine

2'-O-Methoxyethyl-5'-O-dimethoxytrityl-5-methyluridine (106 g, 0.167 M), DMF/pyridine (750 mL of a 3:1 mixture prepared from 562 mL of DMF and 188 mL of pyridine) and acetic anhydride (24.38 mL, 0.258 M) were combined and stirred at room temperature for 24 hours. The reaction was monitored by TLC by first quenching the TLC sample with the addition of MeOH. Upon completion of the reaction, as judged by TLC, MeOH (50 mL) was added and the mixture evaporated at 35° C. The residue was dissolved in $CHCl_3$ (800 mL) and extracted with 2×200 mL of saturated sodium bicarbonate and 2×200 mL of saturated NaCl. The water layers were back extracted with 200 mL of $CHCl_3$. The combined organics were dried with sodium sulfate and evaporated to give 122 g of residue (approx. 90% product). The residue was purified on a 3.5 kg silica gel column and eluted using EtOAc/hexane (4:1). Pure product fractions were evaporated to yield 96 g (84%). An additional 1.5 g was recovered from later fractions.

3'-O-Acetyl-2'-O-methoxyethyl-5'-O-dimethoxytrityl-5-methyl-4-triazoleuridine A first solution was prepared by dissolving 3'-O-acetyl-2'-O-methoxyethyl-5'-O-dimethoxytrityl-5-methyluridine (96 g, 0.144 M) in $CH_3CN$ (700 mL) and set aside. Triethylamine (189 mL, 1.44 M) was added to a solution of triazole (90 g, 1.3 M) in $CH_3CN$ (1 L), cooled to −5° C. and stirred for 0.5 h using an overhead stirrer. $POCl_3$ was added dropwise, over a 30 minute period, to the stirred solution maintained at 0-10° C., and the resulting mixture stirred for an additional 2 hours. The first solution was added dropwise, over a 45 minute period, to the latter solution. The resulting reaction mixture was stored overnight in a cold room. Salts were filtered from the reaction mixture and the solution was evaporated. The residue was dissolved in EtOAc (1 L) and the insoluble solids were removed by filtration. The filtrate was washed with 1×300 mL of $NaHCO_3$ and 2×300 mL of saturated NaCl, dried over sodium sulfate and evaporated. The residue was triturated with EtOAc to give the title compound.

2'-O-Methoxyethyl-5'-O-dimethoxytrityl-5-methylcytidine

A solution of 3'-O-acetyl-2'-O-methoxyethyl-5'-O-dimethoxytrityl-5-methyl-4-triazoleuridine (103 g, 0.141 M) in dioxane (500 mL) and $NH_4OH$ (30 mL) was stirred at room temperature for 2 hours. The dioxane solution was evaporated and the residue azeotroped with MeOH (2×200 mL). The residue was dissolved in MeOH (300 mL) and transferred to a 2 liter stainless steel pressure vessel. MeOH (400 mL) saturated with $NH_3$ gas was added and the vessel heated to 100° C. for 2 hours (TLC showed complete conversion). The vessel contents were evaporated to dryness and the residue was dissolved in EtOAc (500 mL) and washed once with saturated NaCl (200 mL). The organics were dried over sodium sulfate and the solvent was evaporated to give 85 g (95%) of the title compound.

N4-Benzoyl-2'-O-methoxyethyl-5'-O-dimethoxytrityl-5-methylcytidine

2'-O-Methoxyethyl-5'-O-dimethoxytrityl-5-methylcytidine (85 g, 0.134 M) was dissolved in DMF (800 mL) and benzoic anhydride (37.2 g, 0.165 M) was added with stirring. After stirring for 3 hours, TLC showed the reaction to be approximately 95% complete. The solvent was evaporated and the residue azeotroped with MeOH (200 mL). The residue was dissolved in $CHCl_3$ (700 mL) and extracted with saturated $NaHCO_3$ (2×300 mL) and saturated NaCl (2×300 mL), dried over $MgSO_4$ and evaporated to give a residue (96 g). The residue was chromatographed on a 1.5 kg silica column using EtOAc/hexane (1:1) containing 0.5% $Et_3NH$ as the eluting solvent. The pure product fractions were evaporated to give 90 g (90%) of the title compound.

N4-Benzoyl-2'-O-methoxyethyl-5'-O-dimethoxytrityl-5-methylcytidine-3'-amidite N4-Benzoyl-2'-O-methoxyethyl-5'-O-dimethoxytrityl-5-methylcytidine (74 g, 0.10 M) was dissolved in $CH_2Cl_2$ (1 L) Tetrazole diisopropylamine (7.1 g) and 2-cyanoethoxy-tetra-(isopropyl)phosphite (40.5 mL, 0.123 M) were added with stirring, under a nitrogen atmosphere. The resulting mixture was stirred for 20 hours at room temperature (TLC showed the reaction to be 95% complete). The reaction mixture was extracted with saturated $NaHCO_3$ (1×300 mL) and saturated NaCl (3×300 mL). The aqueous washes were back-extracted with $CH_2Cl_2$ (300 mL), and the extracts were combined, dried over $MgSO_4$ and concentrated. The residue obtained was chromatographed on a 1.5 kg silica column using EtOAc/hexane (3:1) as the eluting solvent. The pure fractions were combined to give 90.6 g (87%) of the title compound.

2'-O-(Aminooxyethyl) Nucleoside Amidites and 2'-O-(dimethylaminooxyethyl) Nucleoside Amidites

2'-(Dimethylaminooxyethoxy) Nucleoside Amidites

2'-(Dimethylaminooxyethoxy) nucleoside amidites [also known in the art as 2'-O-(dimethylaminooxyethyl) nucleoside amidites] are prepared as described in the following paragraphs. Adenosine, cytidine and guanosine nucleoside amidites are prepared similarly to the thymidine (5-methyluridine) except the exocyclic amines are protected with a benzoyl moiety in the case of adenosine and cytidine and with isobutyryl in the case of guanosine.

5'-O-tert-Butyldiphenylsilyl-$O^2$-2'-anhydro-5-methyluridine $O^2$-2'-anhydro-5-methyluridine (Pro. Bio. Sint., Varese, Italy, 100.0 g, 0.416 mmol), dimethylaminopyridine (0.66 g, 0.013 eq, 0.0054 mmol) were dissolved in dry pyridine (500 ml) at ambient temperature under an argon atmosphere and with mechanical stirring. tert-Butyldiphenylchlorosilane (125.8 g, 119.0 mL, 1.1 eq, 0.458 mmol) was added in one portion. The reaction was stirred for 16 h at ambient temperature. TLC (Rf 0.22, ethyl acetate) indicated a complete reaction. The solution was concentrated under reduced pressure to a thick oil. This was partitioned between dichloromethane (1 L) and saturated sodium bicarbonate (2×1 L) and brine (1 L). The organic layer was dried over sodium sulfate and concentrated under reduced pressure to a thick oil. The oil was dissolved in a 1:1 mixture of ethyl acetate and ethyl ether (600 mL) and the solution was cooled to −10° C. The resulting crystalline product was collected by filtration, washed with ethyl ether (3×200 mL) and dried (40° C., 1 mm Hg, 24 h) to 149 g (74.8%) of white solid. TLC and NMR were consistent with pure product.

5'-O-tert-Butyldiphenylsilyl-2'-O-(2-hydroxyethyl)-5-methyluridine

In a 2 L stainless steel, unstirred pressure reactor was added borane in tetrahydrofuran (1.0 M, 2.0 eq, 622 mL). In the fume hood and with manual stirring, ethylene glycol (350 mL, excess) was added cautiously at first until the evolution of hydrogen gas subsided. 5'-O-tert-Butyldiphenylsilyl-$O^2$-2'-anhydro-5-methyluridine (149 g, 0.311 mol) and sodium bicarbonate (0.074 g, 0.003 eq) were added with manual stirring. The reactor was sealed and heated in an oil bath until an internal temperature of 160° C. was reached and then maintained for 16 h (pressure<100 psig). The reaction vessel was cooled to ambient and opened. TLC (Rf 0.67 for desired product and Rf 0.82 for ara-T side product, ethyl acetate)

indicated about 70% conversion to the product. In order to avoid additional side product formation, the reaction was stopped, concentrated under reduced pressure (10 to 1 mm Hg) in a warm water bath (40-100° C.) with the more extreme conditions used to remove the ethylene glycol. [Alternatively, once the low boiling solvent is gone, the remaining solution can be partitioned between ethyl acetate and water. The product will be in the organic phase.] The residue was purified by column chromatography (2 kg silica gel, ethyl acetate-hexanes gradient 1:1 to 4:1). The appropriate fractions were combined, stripped and dried to product as a white crisp foam (84 g, 50%), contaminated starting material (17.4 g) and pure reusable starting material 20 g. The yield based on starting material less pure recovered starting material was 58%. TLC and NMR were consistent with 99% pure product.

2'-O-([2-phthalimidoxy)ethyl]-5'-t-butyldiphenylsilyl-5-methyluridine

5'-O-tert-Butyldiphenylsilyl-2'-O-(2-hydroxyethyl)-5-methyluridine (20 g, 36.98 mmol) was mixed with triphenylphosphine (11.63 g, 44.36 mmol) and N-hydroxyphthalimide (7.24 g, 44.36 mmol). It was then dried over $P_2O_5$ under high vacuum for two days at 40° C. The reaction mixture was flushed with argon and dry THF (369.8 mL, Aldrich, sure seal bottle) was added to get a clear solution. Diethyl-azodicarboxylate (6.98 mL, 44.36 mmol) was added dropwise to the reaction mixture. The rate of addition is maintained such that resulting deep red coloration is just discharged before adding the next drop. After the addition was complete, the reaction was stirred for 4 hrs. By that time TLC showed the completion of the reaction (ethylacetate:hexane, 60:40). The solvent was evaporated in vacuum. Residue obtained was placed on a flash column and eluted with ethyl acetate:hexane (60:40), to get 2'-O-([2-phthalimidoxy)ethyl]-5'-t-butyldiphenylsilyl-5-methyluridine as white foam (21.819 g, 86%).

5'-O-tert-butyldiphenylsilyl-2'-O-[(2-formadoximinooxy) ethyl]-5-methyluridine

2'-O-([2-phthalimidoxy)ethyl]-5'-t-butyldiphenylsilyl-5-methyluridine (3.1 g, 4.5 mmol) was dissolved in dry $CH_2Cl_2$ (4.5 mL) and methylhydrazine (300 mL, 4.64 mmol) was added dropwise at −10° C. to 0° C. After 1 h the mixture was filtered, the filtrate was washed with ice cold $CH_2Cl_2$ and the combined organic phase was washed with water, brine and dried over anhydrous $Na_2SO_4$. The solution was concentrated to get 2'-O-(aminooxyethyl) thymidine, which was then dissolved in MeOH (67.5 mL). To this formaldehyde (20% aqueous solution, w/w, 1.1 eq.) was added and the resulting mixture was stirred for 1 h. Solvent was removed under vacuum; residue chromatographed to get 5'-O-tert-butyldiphenylsilyl-2'-O-[(2-formadoximinooxy) ethyl]-5-methyluridine as white foam (1.95 g, 78%).

5'-O-tert-Butyldiphenylsilyl-2'-O—[N,N-dimethylaminooxyethyl]-5-methyluridine

5'-O-tert-butyldiphenylsilyl-2'-O-[(2-formadoximinooxy) ethyl]-5-methyluridine (1.77 g, 3.12 mmol) was dissolved in a solution of 1M pyridinium p-toluenesulfonate (PPTS) in dry MeOH (30.6 mL). Sodium cyanoborohydride (0.39 g, 6.13 mmol) was added to this solution at 10° C. under inert atmosphere. The reaction mixture was stirred for 10 minutes at 10° C. After that the reaction vessel was removed from the ice bath and stirred at room temperature for 2 h, the reaction monitored by TLC (5% MeOH in $CH_2Cl_2$). Aqueous $NaHCO_3$ solution (5%, 10 mL) was added and extracted with ethyl acetate (2×20 mL). Ethyl acetate phase was dried over anhydrous $Na_2SO_4$, evaporated to dryness. Residue was dissolved in a solution of 1M PPTS in MeOH (30.6 mL). Formaldehyde (20% w/w, 30 mL, 3.37 mmol) was added and the reaction mixture was stirred at room temperature for 10 minutes. Reaction mixture cooled to 10° C. in an ice bath, sodium cyanoborohydride (0.39 g, 6.13 mmol) was added and reaction mixture stirred at 10° C. for 10 minutes. After 10 minutes, the reaction mixture was removed from the ice bath and stirred at room temperature for 2 hrs. To the reaction mixture 5% $NaHCO_3$ (25 mL) solution was added and extracted with ethyl acetate (2×25 mL). Ethyl acetate layer was dried over anhydrous $Na_2SO_4$ and evaporated to dryness. The residue obtained was purified by flash column chromatography and eluted with 5% MeOH in $CH_2Cl_2$ to get 5'-O-tert-butyldiphenylsilyl-2'-O-[N,N-dimethylaminooxyethyl]-5-methyluridine as a white foam (14.6 g, 80%).

2'-O-(dimethylaminooxyethyl)-5-methyluridine

Triethylamine trihydrofluoride (3.91 mL, 24.0 mmol) was dissolved in dry THF and triethylamine (1.67 mL, 12 mmol, dry, kept over KOH). This mixture of triethylamine-2HF was then added to 5'-O-tert-butyldiphenylsilyl-2'-O—[N,N-dimethylaminooxyethyl]-5-methyluridine (1.40 g, 2.4 mmol) and stirred at room temperature for 24 hrs. Reaction was monitored by TLC (5% MeOH in $CH_2Cl_2$). Solvent was removed under vacuum and the residue placed on a flash column and eluted with 10% MeOH in $CH_2Cl_2$ to get 2'-O-(dimethylaminooxyethyl)-5-methyluridine (766 mg, 92.5%).

5'-O-DMT-2'-O-(dimethylaminooxyethyl)-5-methyluridine

2'-O-(dimethylaminooxyethyl)-5-methyluridine (750 mg, 2.17 mmol) was dried over $P_2O_5$ under high vacuum overnight at 40° C. It was then co-evaporated with anhydrous pyridine (20 mL). The residue obtained was dissolved in pyridine (11 mL) under argon atmosphere. 4-dimethylaminopyridine (26.5 mg, 2.60 mmol), 4,4'-dimethoxytrityl chloride (880 mg, 2.60 mmol) was added to the mixture and the reaction mixture was stirred at room temperature until all of the starting material disappeared. Pyridine was removed under vacuum and the residue chromatographed and eluted with 10% MeOH in $CH_2Cl_2$ (containing a few drops of pyridine) to get 5'-O-DMT-2'-O-(dimethylamino-oxyethyl)-5-methyluridine (1.13 g, 80%).

5'-O-DMT-2'-O-(2-N,N-dimethylaminooxyethyl)-5-methyluridine-3'-[(2-cyanoethyl)-N,N-diisopropylphosphoramidite]

5'-O-DMT-2'-O-(dimethylaminooxyethyl)-5-methyluridine (1.08 g, 1.67 mmol) was co-evaporated with toluene (20 mL). To the residue N,N-diisopropylamine tetrazonide (0.29 g, 1.67 mmol) was added and dried over $P_2O_5$ under high vacuum overnight at 40° C. Then the reaction mixture was dissolved in anhydrous acetonitrile (8.4 mL) and 2-cyanoethyl-N,N,$N^1$,$N^1$-tetraisopropylphosphoramidite (2.12 mL, 6.08 mmol) was added. The reaction mixture was stirred at ambient temperature for 4 hrs under inert atmosphere. The progress of the reaction was monitored by TLC (hexane:ethyl acetate 1:1). The solvent was evaporated, then the residue was dissolved in ethyl acetate (70 mL) and washed with 5% aqueous $NaHCO_3$ (40 mL). Ethyl acetate layer was dried over anhydrous $Na_2SO_4$ and concentrated. Residue obtained was chromatographed (ethyl acetate as eluent) to get 5'-O-DMT-2'-O-(2-N,N-dimethylaminooxyethyl)-5-methyluridine-3'-[(2-cyanoethyl)-N,N-diisopropylphosphoramidite] as a foam (1.04 g, 74.9%).

2'-(Aminooxyethoxy) Nucleoside Amidites

2'-(Aminooxyethoxy) nucleoside amidites [also known in the art as 2'-O-(aminooxyethyl) nucleoside amidites] are prepared as described in the following paragraphs. Adenosine, cytidine and thymidine nucleoside amidites are prepared similarly.

N2-isobutyryl-6-O-diphenylcarbamoyl-2'-O-(2-ethylacetyl)-5'-O-(4,4'-dimethoxytrityl)guanosine-3'-[(2-cyanoethyl)-N,N-diisopropylphosphoramidite]

The 2'-O-aminooxyethyl guanosine analog may be obtained by selective 2'-O-alkylation of diaminopurine riboside. Multigram quantities of diaminopurine riboside may be purchased from Schering AG (Berlin) to provide 2'-O-(2-ethylacetyl) diaminopurine riboside along with a minor amount of the 3'-O-isomer. 2'-O-(2-ethylacetyl) diaminopurine riboside may be resolved and converted to 2'-O-(2-ethylacetyl)guanosine by treatment with adenosine deaminase. (McGee, D. P. C., Cook, P. D., Guinosso, C. J., WO 94/02501 A1 940203.) Standard protection procedures should afford 2'-O-(2-ethylacetyl)-5'-O-(4,4'-dimethoxytrityl)guanosine and 2-N-isobutyryl-6-O-diphenylcarbamoyl-2'-O-(2-ethylacetyl)-5'-O-(4,4'-dimethoxytrityl)guanosine which may be reduced to provide 2-N-isobutyryl-6-O-diphenylcarbamoyl-2'-O-(2-hydroxyethyl)-5'-O-(4,4'-dimethoxytrityl)guanosine. As before the hydroxyl group may be displaced by N-hydroxyphthalimide via a Mitsunobu reaction, and the protected nucleoside may phosphitylated as usual to yield 2-N-isobutyryl-6-O-diphenylcarbamoyl-2'-O-([2-phthalmidoxy]ethyl)-5'-O-(4,4'-dimethoxytrityl)guanosine-3'-[(2-cyanoethyl)-N,N-diisopropylphosphoramidite].

2'-dimethylaminoethoxyethoxy (2'-DMAEOE) Nucleoside Amidites

2'-dimethylaminoethoxyethoxy nucleoside amidites (also known in the art as 2'-O-dimethylaminoethoxyethyl, i.e., 2'-O—$CH_2$—O—$CH_2$—$N(CH_2)_2$, or 2'-DMAEOE nucleoside amidites) are prepared as follows. Other nucleoside amidites are prepared similarly.

2'-O-[2(2-N,N-dimethylaminoethoxy)ethyl]-5-methyl Uridine

2[2-(Dimethylamino)ethoxy]ethanol (Aldrich, 6.66 g, 50 mmol) is slowly added to a solution of borane in tetrahydrofuran (1 M, 10 mL, 10 mmol) with stirring in a 100 mL bomb. Hydrogen gas evolves as the solid dissolves. $O^2$-, 2'-anhydro-5-methyluridine (1.2 g, 5 mmol), and sodium bicarbonate (2.5 mg) are added and the bomb is sealed, placed in an oil bath and heated to 155° C. for 26 hours. The bomb is cooled to room temperature and opened. The crude solution is concentrated and the residue partitioned between water (200 mL) and hexanes (200 mL). The excess phenol is extracted into the hexane layer. The aqueous layer is extracted with ethyl acetate (3×200 mL) and the combined organic layers is washed once with water, dried over anhydrous sodium sulfate and concentrated. The residue is columned on silica gel using methanol/methylene chloride 1:20 (which has 2% triethylamine) as the eluent. As the column fractions are concentrated a colorless solid forms which is collected to give the title compound as a white solid.

5'-O-dimethoxytrityl-2'-O-[2(2-N,N-dimethylaminoethoxy)-ethyl)]-5-methyl Uridine To 0.5 g (1.3 mmol) of 2'-O-[2(2-N,N-dimethylaminoethoxy)ethyl]-5-methyl uridine in anhydrous pyridine (8 mL), triethylamine (0.36 mL) and dimethoxytrityl chloride (DMT-Cl, 0.87 g, 2 eq.) are added and stirred for 1 hour. The reaction mixture is poured into water (200 mL) and extracted with $CH_2Cl_2$ (2×200 mL). The combined $CH_2Cl_2$ layers are washed with saturated $NaHCO_3$ solution, followed by saturated NaCl solution and dried over anhydrous sodium sulfate. Evaporation of the solvent followed by silica gel chromatography using MeOH:$CH_2Cl_2$:$Et_3N$ (20:1, v/v, with 1% triethylamine) gives the title compound.

5'-O-Dimethoxytrityl-2'-O-[2(2-N,N-dimethylaminoethoxy)ethyl)]-5-methyl uridine-3'-O-(cyanoethyl-N,N-diisopropyl)phosphoramidite Diisopropylaminotetrazolide (0.6 g) and 2-cyanoethoxy-N,N-diisopropyl phosphoramidite (1.1 mL, 2 eq.) are added to a solution of 5'-O-dimethoxytrityl-2'-O-[2(2-N,N-dimethylaminoethoxy)ethyl)]-5-methyluridine (2.17 g, 3 mmol) dissolved in $CH_2Cl_2$ (20 mL) under an atmosphere of argon. The reaction mixture is stirred overnight and the solvent evaporated. The resulting residue is purified by silica gel flash column chromatography with ethyl acetate as the eluent to give the title compound.

Example 2

Oligonucleotide Synthesis

Unsubstituted and substituted phosphodiester (P=O) oligonucleotides are synthesized on an automated DNA synthesizer (Applied Biosystems model 380B) using standard phosphoramidite chemistry with oxidation by iodine.

Phosphorothioates (P=S) are synthesized as for the phosphodiester oligonucleotides except the standard oxidation bottle was replaced by 0.2 M solution of 3H-1,2-benzodithiole-3-one 1,1-dioxide in acetonitrile for the stepwise thiation of the phosphite linkages. The thiation wait step was increased to 68 sec and was followed by the capping step. After cleavage from the CPG column and deblocking in concentrated ammonium hydroxide at 55° C. (18 h), the oligonucleotides were purified by precipitating twice with 2.5 volumes of ethanol from a 0.5 M NaCl solution. Phosphinate oligonucleotides are prepared as described in U.S. Pat. No. 5,508,270, herein incorporated by reference.

Alkyl phosphonate oligonucleotides are prepared as described in U.S. Pat. No. 4,469,863, herein incorporated by reference.

3'-Deoxy-3'-methylene phosphonate oligonucleotides are prepared as described in U.S. Pat. Nos. 5,610,289 or 5,625,050, herein incorporated by reference.

Phosphoramidite oligonucleotides are prepared as described in U.S. Pat. No. 5,256,775 or U.S. Pat. No. 5,366,878, herein incorporated by reference.

Alkylphosphonothioate oligonucleotides are prepared as described in published PCT applications PCT/US94/00902 and PCT/US93/06976 (published as WO 94/17093 and WO 94/02499, respectively), herein incorporated by reference.

3'-Deoxy-3'-amino phosphoramidate oligonucleotides are prepared as described in U.S. Pat. No. 5,476,925, herein incorporated by reference.

Phosphotriester oligonucleotides are prepared as described in U.S. Pat. No. 5,023,243, herein incorporated by reference.

Borano phosphate oligonucleotides are prepared as described in U.S. Pat. Nos. 5,130,302 and 5,177,198, both herein incorporated by reference.

Example 3

Oligonucleoside Synthesis

Methylenemethylimino linked oligonucleosides, also identified as MMI linked oligonucleosides, methylenedimethylhydrazo linked oligonucleosides, also identified as MDH linked oligonucleosides, and methylenecarbonylamino linked oligonucleosides, also identified as amide-3 linked oligonucleosides, and methyleneaminocarbonyl linked oligonucleosides, also identified as amide-4 linked oligonucleosides, as well as mixed backbone compounds having, for instance, alternating MMI and P=O or P=S linkages are prepared as described in U.S. Pat. Nos. 5,378,825, 5,386,023, 5,489,677, 5,602,240 and 5,610,289, all of which are herein incorporated by reference.

Formacetal and thioformacetal linked oligonucleosides are prepared as described in U.S. Pat. Nos. 5,264,562 and 5,264,564, herein incorporated by reference.

Ethylene oxide linked oligonucleosides are prepared as described in U.S. Pat. No. 5,223,618, herein incorporated by reference.

Example 4

PNA Synthesis

Peptide nucleic acids (PNAs) are prepared in accordance with any of the various procedures referred to in Peptide Nucleic Acids (PNA): Synthesis, Properties and Potential Applications, *Bioorganic & Medicinal Chemistry*, 1996, 4, 5-23. They may also be prepared in accordance with U.S. Pat. Nos. 5,539,082, 5,700,922, and 5,719,262, herein incorporated by reference.

Example 5

Synthesis of Chimeric Oligonucleotides

Chimeric oligonucleotides, oligonucleosides or mixed oligonucleotides/oligonucleosides of the invention can be of several different types. These include a first type wherein the "gap" segment of linked nucleosides is positioned between 5' and 3' "wing" segments of linked nucleosides and a second "open end" type wherein the "gap" segment is located at either the 3' or the 5' terminus of the oligomeric compound. Oligonucleotides of the first type are also known in the art as "gapmers" or gapped oligonucleotides. Oligonucleotides of the second type are also known in the art as "hemimers" or "wingmers".

[2'-O-Me]-[2'-deoxy]-[2'-O-Me] Chimeric Phosphorothioate Oligonucleotides

Chimeric oligonucleotides having 2'-O-alkyl phosphorothioate and 2'-deoxy phosphorothioate oligonucleotide segments are synthesized using an Applied Biosystems automated DNA synthesizer Model 380B, as above. Oligonucleotides are synthesized using the automated synthesizer and 2'-deoxy-5'-dimethoxytrityl-3'-O-phosphoramidite for the DNA portion and 5'-dimethoxytrityl-2'-O-methyl-3'-O-phosphoramidite for 5' and 3' wings. The standard synthesis cycle is modified by increasing the wait step after the delivery of tetrazole and base to 600 s repeated four times for RNA and twice for 2'-O-methyl. The fully protected oligonucleotide is cleaved from the support and the phosphate group is deprotected in 3:1 ammonia/ethanol at room temperature overnight then lyophilized to dryness. Treatment in methanolic ammonia for 24 hrs at room temperature is then done to deprotect all bases and sample was again lyophilized to dryness. The pellet is resuspended in 1M TBAF in THF for 24 hrs at room temperature to deprotect the 2' positions. The reaction is then quenched with 1M TEAA and the sample is then reduced to ½ volume by rotovac before being desalted on a G25 size exclusion column. The oligo recovered is then analyzed spectrophotometrically for yield and for purity by capillary electrophoresis and by mass spectrometry.

[2'-O-(2-Methoxyethyl)]-[2'-deoxy]-[2'-O-(Methoxyethyl)] Chimeric Phosphorothioate Oligonucleotides

[2'-O-(2-methoxyethyl)]-[2'-deoxy]-[-2'-O-(methoxyethyl)] chimeric phosphorothioate oligonucleotides were prepared as per the procedure above for the 2'-O-methyl chimeric oligonucleotide, with the substitution of 2'-O-(methoxyethyl) amidites for the 2'-O-methyl amidites.

[2'-O-(2-Methoxyethyl)Phosphodiester]-[2'-deoxy Phosphorothioate]-[2'-O-(2-Methoxyethyl) Phosphodiester] Chimeric Oligonucleotides

[2'-O-(2-methoxyethyl phosphodiester]-[2'-deoxy phosphorothioate]-[2'-O-(methoxyethyl) phosphodiester] chimeric oligonucleotides are prepared as per the above procedure for the 2'-O-methyl chimeric oligonucleotide with the substitution of 2'-O-(methoxyethyl) amidites for the 2'-O-methyl amidites, oxidization with iodine to generate the phosphodiester internucleotide linkages within the wing portions of the chimeric structures and sulfurization utilizing 3,H-1,2 benzodithiole-3-one 1,1 dioxide (Beaucage Reagent) to generate the phosphorothioate internucleotide linkages for the center gap.

Other chimeric oligonucleotides, chimeric oligonucleosides and mixed chimeric oligonucleotides/oligonucleosides are synthesized according to U.S. Pat. No. 5,623,065, herein incorporated by reference.

Example 6

Oligonucleotide Isolation

After cleavage from the controlled pore glass column (Applied Biosystems) and deblocking in concentrated ammonium hydroxide at 55° C. for 18 hours, the oligonucleotides or oligonucleosides are purified by precipitation twice out of 0.5 M NaCl with 2.5 volumes ethanol. Synthesized oligonucleotides were analyzed by polyacrylamide gel electrophoresis on denaturing gels and judged to be at least 85% full length material. The relative amounts of phosphorothioate and phosphodiester linkages obtained in synthesis were periodically checked by $^{31}P$ nuclear magnetic resonance spectroscopy, and for some studies oligonucleotides were purified by HPLC, as described by Chiang et al., *J. Biol. Chem.* 1991, 266, 18162-18171. Results obtained with HPLC-purified material were similar to those obtained with non-HPLC purified material.

Example 7

Oligonucleotide Synthesis—96 Well Plate Format

Oligonucleotides were synthesized via solid phase P(III) phosphoramidite chemistry on an automated synthesizer capable of assembling 96 sequences simultaneously in a standard 96 well format. Phosphodiester internucleotide linkages were afforded by oxidation with aqueous iodine. Phosphorothioate internucleotide linkages were generated by sulfurization utilizing 3,H-1,2 benzodithiole-3-one 1,1 dioxide (Beaucage Reagent) in anhydrous acetonitrile. Standard base-protected beta-cyanoethyldiisopropyl phosphoramidites were purchased from commercial vendors (e.g. PE-Applied Biosystems, Foster City, Calif., or Pharmacia, Piscataway, N.J.). Non-standard nucleosides are synthesized as per known literature or patented methods. They are utilized as base protected beta-cyanoethyldiisopropyl phosphoramidites.

Oligonucleotides were cleaved from support and deprotected with concentrated $NH_4OH$ at elevated temperature (55-60° C.) for 12-16 hours and the released product then dried in vacuo. The dried product was then re-suspended in sterile water to afford a master plate from which all analytical and test plate samples are then diluted utilizing robotic pipettors.

Example 8

Oligonucleotide Analysis—96 Well Plate Format

The concentration of oligonucleotide in each well was assessed by dilution of samples and UV absorption spectroscopy. The full-length integrity of the individual products was evaluated by capillary electrophoresis (CE) in either the 96 well format (Beckman P/ACE™ MDQ) or, for individually prepared samples, on a commercial CE apparatus (e.g., Beckman P/ACE™ 5000, ABI 270). Base and backbone composition was confirmed by mass analysis of the compounds utilizing electrospray-mass spectroscopy. All assay test plates were diluted from the master plate using single and multichannel robotic pipettors. Plates were judged to be acceptable if at least 85% of the compounds on the plate were at least 85% full length.

Example 9

Cell Culture and Oligonucleotide Treatment

The effect of antisense compounds on target nucleic acid expression can be tested in any of a variety of cell types provided that the target nucleic acid is present at measurable levels. This can be routinely determined using, for example, PCR or Northern blot analysis. The following 7 cell types are provided for illustrative purposes, but other cell types can be routinely used, provided that the target is expressed in the cell type chosen. This can be readily determined by methods routine in the art, for example Northern blot analysis, Ribonuclease protection assays, or RT-PCR.

T-24 Cells:

The human transitional cell bladder carcinoma cell line T-24 was obtained from the American Type Culture Collection (ATCC) (Manassas, Va.). T-24 cells were routinely cultured in complete McCoy's 5A basal media (Gibco/Life Technologies, Gaithersburg, Md.) supplemented with 10% fetal calf serum (Gibco/Life Technologies, Gaithersburg, Md.), penicillin 100 units per mL, and streptomycin 100 micrograms per mL (Gibco/Life Technologies, Gaithersburg, Md.). Cells were routinely passaged by trypsinization and dilution when they reached 90% confluence. Cells were seeded into 96-well plates (Falcon-Primaria #3872) at a density of 7000 cells/well for use in RT-PCR analysis.

For Northern blotting or other analysis, cells may be seeded onto 100 mm or other standard tissue culture plates and treated similarly, using appropriate volumes of medium and oligonucleotide.

A549 Cells:

The human lung carcinoma cell line A549 was obtained from the American Type Culture Collection (ATCC) (Manassas, Va.). A549 cells were routinely cultured in DMEM basal media (Gibco/Life Technologies, Gaithersburg, Md.) supplemented with 10% fetal calf serum (Gibco/Life Technologies, Gaithersburg, Md.), penicillin 100 units per mL, and streptomycin 100 micrograms per mL (Gibco/Life Technologies, Gaithersburg, Md.). Cells were routinely passaged by trypsinization and dilution when they reached 90% confluence.

NHDF Cells:

Human neonatal dermal fibroblast (NHDF) were obtained from the Clonetics Corporation (Walkersville Md.). NHDFs were routinely maintained in Fibroblast Growth Medium (Clonetics Corporation, Walkersville Md.) supplemented as recommended by the supplier. Cells were maintained for up to 10 passages as recommended by the supplier.

HEK Cells:

Human embryonic keratinocytes (HEK) were obtained from the Clonetics Corporation (Walkersville Md.). HEKs were routinely maintained in Keratinocyte Growth Medium (Clonetics Corporation, Walkersville Md.) formulated as recommended by the supplier. Cells were routinely maintained for up to 10 passages as recommended by the supplier.

HepG2 Cells:

The human hepatoblastoma cell line HepG2 was obtained from the American Type Culture Collection (Manassas, Va.). HepG2 cells were routinely cultured in Eagle's MEM supplemented with 10% fetal calf serum, non-essential amino acids, and 1 mM sodium pyruvate (Gibco/Life Technologies, Gaithersburg, Md.). Cells were routinely passaged by trypsinization and dilution when they reached 90% confluence. Cells were seeded into 96-well plates (Falcon-Primaria #3872) at a density of 7000 cells/well for use in RT-PCR analysis.

For Northern blotting or other analyses, cells may be seeded onto 100 mm or other standard tissue culture plates and treated similarly, using appropriate volumes of medium and oligonucleotide.

AML12 Cells:

The AML12 (alpha mouse liver 12) cell line was established from hepatocytes from a mouse (CD1 strain, line MT42) transgenic for human TGF alpha. Cells are cultured in a 1:1 mixture of Dulbecco's modified Eagle's medium and Ham's F12 medium with 0.005 mg/ml insulin, 0.005 mg/ml transferrin, 5 ng/ml selenium, and 40 ng/ml dexamethasone, and 90%; 10% fetal bovine serum. For subculturing, spent medium is removed and fresh media of 0.25% trypsin, 0.03% EDTA solution is added. Fresh trypsin solution (1 to 2 ml) is added and the culture is left to sit at room temperature until the cells detach.

Cells were routinely passaged by trypsinization and dilution when they reached 90% confluence. Cells were seeded into 96-well plates (Falcon-Primaria #3872) at a density of 7000 cells/well for use in RT-PCR analysis.

For Northern blotting or other analyses, cells may be seeded onto 100 mm or other standard tissue culture plates and treated similarly, using appropriate volumes of medium and oligonucleotide.

Primary Mouse Hepatocytes:

Primary mouse hepatocytes were prepared from CD-1 mice purchased from Charles River Labs (Wilmington, Mass.) and were routinely cultured in Hepatoyte Attachment Media (Gibco) supplemented with 10% Fetal Bovine Serum (Gibco/Life Technologies, Gaithersburg, Md.), 250 nM dexamethasone (Sigma), and 10 nM bovine insulin (Sigma). Cells were seeded into 96-well plates (Falcon-Primaria #3872) at a density of 10000 cells/well for use in RT-PCR analysis.

For Northern blotting or other analyses, cells are plated onto 100 mm or other standard tissue culture plates coated with rat tail collagen (200 ug/mL) (Becton Dickinson) and treated similarly using appropriate volumes of medium and oligonucleotide.

Treatment with Antisense Compounds:

When cells reached 80% confluency, they were treated with oligonucleotide. For cells grown in 96-well plates, wells were washed once with 200 μL OPTI-MEM™-1 reduced-serum medium (Gibco BRL) and then treated with 130 μL of OPTI-MEM™-1 containing 3.75 μg/mL LIPOFECTIN™

(Gibco BRL) and the desired concentration of oligonucleotide. After 4-7 hours of treatment, the medium was replaced with fresh medium. Cells were harvested 16-24 hours after oligonucleotide treatment.

The concentration of oligonucleotide used varies from cell line to cell line. To determine the optimal oligonucleotide concentration for a particular cell line, the cells are treated with a positive control oligonucleotide at a range of concentrations. For human cells the positive control oligonucleotide is ISIS 13920, TCCGTCATCGCTCCTCAGGG, SEQ ID NO: 1, a 2'-O-methoxyethyl gapmer (2'-O-methoxyethyls shown in bold) with a phosphorothioate backbone which is targeted to human H-ras. For mouse or rat cells the positive control oligonucleotide is ISIS 15770, ATGCATTCTGC-CCCCAAGGA, SEQ ID NO: 2, a 2'-O-methoxyethyl gapmer (2'-O-methoxyethyls shown in bold) with a phosphorothioate backbone which is targeted to both mouse and rat c-raf. The concentration of positive control oligonucleotide that results in 80% inhibition of c-Ha-ras (for ISIS 13920) or c-raf (for ISIS 15770) mRNA is then utilized as the screening concentration for new oligonucleotides in subsequent experiments for that cell line. If 80% inhibition is not achieved, the lowest concentration of positive control oligonucleotide that results in 60% inhibition of H-ras or c-raf mRNA is then utilized as the oligonucleotide screening concentration in subsequent experiments for that cell line. If 60% inhibition is not achieved, that particular cell line is deemed as unsuitable for oligonucleotide transfection experiments.

Example 10

Analysis of Oligonucleotide Inhibition of Apolipoprotein B Expression

Antisense modulation of apolipoprotein B expression can be assayed in a variety of ways known in the art. For example, apolipoprotein B mRNA levels can be quantitated by, e.g., Northern blot analysis, competitive polymerase chain reaction (PCR), or real-time PCR (RT-PCR). Real-time quantitative PCR is presently preferred. RNA analysis can be performed on total cellular RNA or poly(A)+ mRNA. Methods of RNA isolation are taught in, for example, Ausubel, F. M. et al., Current Protocols in Molecular Biology, Volume 1, pp. 4.1.1-4.2.9 and 4.5.1-4.5.3, John Wiley & Sons, Inc., 1993. Northern blot analysis is routine in the art and is taught in, for example, Ausubel, F. M. et al., Current Protocols in Molecular Biology, Volume 1, pp. 4.2.1-4.2.9, John Wiley & Sons, Inc., 1996. Real-time quantitative (PCR) can be conveniently accomplished using the commercially available ABI PRISM™ 7700 Sequence Detection System, available from PE-Applied Biosystems, Foster City, Calif. and used according to manufacturer's instructions.

Protein levels of apolipoprotein B can be quantitated in a variety of ways well known in the art, such as immunoprecipitation, Western blot analysis (immunoblotting), ELISA or fluorescence-activated cell sorting (FACS). Antibodies directed to apolipoprotein B can be identified and obtained from a variety of sources, such as the MSRS catalog of antibodies (Aerie Corporation, Birmingham, Mich.), or can be prepared via conventional antibody generation methods. Methods for preparation of polyclonal antisera are taught in, for example, Ausubel, F. M. et al., Current Protocols in Molecular Biology, Volume 2, pp. 11.12.1-11.12.9, John Wiley & Sons, Inc., 1997. Preparation of monoclonal antibodies is taught in, for example, Ausubel, F. M. et al., Current Protocols in Molecular Biology, Volume 2, pp. 11.4.1-11.11.5, John Wiley & Sons, Inc., 1997.

Immunoprecipitation methods are standard in the art and can be found at, for example, Ausubel, F. M. et al., Current Protocols in Molecular Biology, Volume 2, pp. 10.16.1-10.16.11, John Wiley & Sons, Inc., 1998. Western blot (immunoblot) analysis is standard in the art and can be found at, for example, Ausubel, F. M. et al., Current Protocols in Molecular Biology, Volume 2, pp. 10.8.1-10.8.21, John Wiley & Sons, Inc., 1997. Enzyme-linked immunosorbent assays (ELISA) are standard in the art and can be found at, for example, Ausubel, F. M. et al., Current Protocols in Molecular Biology, Volume 2, pp. 11.2.1-11.2.22, John Wiley & Sons, Inc., 1991.

Example 11

Poly(A)+ mRNA Isolation

Poly(A)+ mRNA was isolated according to Miura et al., Clin. Chem., 1996, 42, 1758-1764. Other methods for poly (A)+ mRNA isolation are taught in, for example, Ausubel, F. M. et al., Current Protocols in Molecular Biology, Volume 1, pp. 4.5.1-4.5.3, John Wiley & Sons, Inc., 1993. Briefly, for cells grown on 96-well plates, growth medium was removed from the cells and each well was washed with 200 µL cold PBS. 60 µL lysis buffer (10 mM Tris-HCl, pH 7.6, 1 mM EDTA, 0.5 M NaCl, 0.5% NP-40, 20 mM vanadyl-ribonucleoside complex) was added to each well, the plate was gently agitated and then incubated at room temperature for five minutes. 55 µL of lysate was transferred to Oligo d(T) coated 96-well plates (AGCT Inc., Irvine Calif.). Plates were incubated for 60 minutes at room temperature, washed 3 times with 200 µL of wash buffer (10 mM Tris-HCl pH 7.6, 1 mM EDTA, 0.3 M NaCl). After the final wash, the plate was blotted on paper towels to remove excess wash buffer and then air-dried for 5 minutes. 60 µL of elution buffer (5 mM Tris-HCl pH 7.6), preheated to 70° C. was added to each well, the plate was incubated on a 90° C. hot plate for 5 minutes, and the eluate was then transferred to a fresh 96-well plate.

Cells grown on 100 mm or other standard plates may be treated similarly, using appropriate volumes of all solutions.

Example 12

Total RNA Isolation

Total RNA was isolated using an RNEASY 96™ kit and buffers purchased from Qiagen Inc. (Valencia Calif.) following the manufacturer's recommended procedures. Briefly, for cells grown on 96-well plates, growth medium was removed from the cells and each well was washed with 200 µL cold PBS. 100 µL Buffer RLT was added to each well and the plate vigorously agitated for 20 seconds. 100 µL of 70% ethanol was then added to each well and the contents mixed by pipetting three times up and down. The samples were then transferred to the RNEASY 96™ well plate attached to a QIAVAC™ manifold fitted with a waste collection tray and attached to a vacuum source. Vacuum was applied for 15 seconds. 1 mL of Buffer RW1 was added to each well of the RNEASY 96™ plate and the vacuum again applied for 15 seconds. 1 mL of Buffer RPE was then added to each well of the RNEASY 96™ plate and the vacuum applied for a period of 15 seconds. The Buffer RPE wash was then repeated and the vacuum was applied for an additional 10 minutes. The plate was then removed from the QIAVAC™ manifold and blotted dry on paper towels. The plate was then re-attached to the QIAVAC™ manifold fitted with a collection tube rack containing 1.2 mL collection tubes. RNA was then eluted by pipetting 60 µL water into each well, incubating 1 minute, and then applying the vacuum for 30 seconds. The elution step was repeated with an additional 60 µL water.

The repetitive pipetting and elution steps may be automated using a QIAGEN Bio-Robot 9604 (Qiagen, Inc., Valencia Calif.). Essentially, after lysing of the cells on the culture plate, the plate is transferred to the robot deck where the pipetting, DNase treatment and elution steps are carried out.

Example 13

Real-Time Quantitative PCR Analysis of Apolipoprotein B mRNA Levels

Quantitation of apolipoprotein B mRNA levels was determined by real-time quantitative PCR using the ABI PRISM™ 7700 Sequence Detection System (PE-Applied Biosystems, Foster City, Calif.) according to manufacturer's instructions. This is a closed-tube, non-gel-based, fluorescence detection system which allows high-throughput quantitation of polymerase chain reaction (PCR) products in real-time. As opposed to standard PCR, in which amplification products are quantitated after the PCR is completed, products in real-time quantitative PCR are quantitated as they accumulate. This is accomplished by including in the PCR reaction an oligonucleotide probe that anneals specifically between the forward and reverse PCR primers, and contains two fluorescent dyes. A reporter dye (e.g., JOE, FAM, or VIC, obtained from either Operon Technologies Inc., Alameda, Calif. or PE-Applied Biosystems, Foster City, Calif.) is attached to the 5' end of the probe and a quencher dye (e.g., TAMRA, obtained from either Operon Technologies Inc., Alameda, Calif. or PE-Applied Biosystems, Foster City, Calif.) is attached to the 3' end of the probe. When the probe and dyes are intact, reporter dye emission is quenched by the proximity of the 3' quencher dye. During amplification, annealing of the probe to the target sequence creates a substrate that can be cleaved by the 5'-exonuclease activity of Taq polymerase. During the extension phase of the PCR amplification cycle, cleavage of the probe by Taq polymerase releases the reporter dye from the remainder of the probe (and hence from the quencher moiety) and a sequence-specific fluorescent signal is generated. With each cycle, additional reporter dye molecules are cleaved from their respective probes, and the fluorescence intensity is monitored at regular intervals by laser optics built into the ABI PRISM™ 7700 Sequence Detection System. In each assay, a series of parallel reactions containing serial dilutions of mRNA from untreated control samples generates a standard curve that is used to quantitate the percent inhibition after antisense oligonucleotide treatment of test samples.

Prior to quantitative PCR analysis, primer-probe sets specific to the target gene being measured are evaluated for their ability to be "multiplexed" with a GAPDH amplification reaction. In multiplexing, both the target gene and the internal standard gene GAPDH are amplified concurrently in a single sample. In this analysis, mRNA isolated from untreated cells is serially diluted. Each dilution is amplified in the presence of primer-probe sets specific for GAPDH only, target gene only ("single-plexing"), or both (multiplexing). Following PCR amplification, standard curves of GAPDH and target mRNA signal as a function of dilution are generated from both the single-plexed and multiplexed samples. If both the slope and correlation coefficient of the GAPDH and target signals generated from the multiplexed samples fall within 10% of their corresponding values generated from the single-plexed samples, the primer-probe set specific for that target is deemed multiplexable. Other methods of PCR are also known in the art.

PCR reagents were obtained from PE-Applied Biosystems, Foster City, Calif. RT-PCR reactions were carried out by adding 25 µL PCR cocktail (1× TAQMAN™ buffer A, 5.5 mM MgCl$_2$, 300 µM each of dATP, dCTP and dGTP, 600 µM of dUTP, 100 nM each of forward primer, reverse primer, and probe, 20 Units RNAse inhibitor, 1.25 Units AMPLITAQ GOLD™, and 12.5 Units MuLV reverse transcriptase) to 96 well plates containing 25 µL total RNA solution. The RT reaction was carried out by incubation for 30 minutes at 48° C. Following a 10 minute incubation at 95° C. to activate the AMPLITAQ GOLD™, 40 cycles of a two-step PCR protocol were carried out: 95° C. for 15 seconds (denaturation) followed by 60° C. for 1.5 minutes (annealing/extension).

Gene target quantities obtained by real time RT-PCR are normalized using either the expression level of GAPDH, a gene whose expression is constant, or by quantifying total RNA using RiboGreen™ (Molecular Probes, Inc. Eugene, Oreg.). GAPDH expression is quantified by real time RT-PCR, by being run simultaneously with the target, multiplexing, or separately. Total RNA is quantified using RiboGreen™ RNA quantification reagent from Molecular Probes. Methods of RNA quantification by RiboGreen™ are taught in Jones, L. J., et al, *Analytical Biochemistry*, 1998, 265, 368-374.

In this assay, 175 µL of RiboGreen™ working reagent (RiboGreen™ reagent diluted 1:2865 in 10 mM Tris-HCl, 1 mM EDTA, pH 7.5) is pipetted into a 96-well plate containing 25 uL purified, cellular RNA. The plate is read in a CytoFluor 4000 (PE Applied Biosystems) with excitation at 480 nm and emission at 520 nm.

Probes and primers to human apolipoprotein B were designed to hybridize to a human apolipoprotein B sequence, using published sequence information (GenBank accession number NM_000384, incorporated herein as SEQ ID NO: 3).

For human apolipoprotein B the PCR primers were:
forward primer: TGCTAAAGGCACATATGGCCT (SEQ ID NO: 4)
reverse primer: CTCAGGTTGGACTCTCCATTGAG (SEQ ID NO: 5) and the PCR probe was: FAM-CTTGTCA-GAGGGATCCTAACACTGGCCG-TAMRA (SEQ ID NO: 6) where FAM (PE-Applied Biosystems, Foster City, Calif.) is the fluorescent reporter dye) and TAMRA (PE-Applied Biosystems, Foster City, Calif.) is the quencher dye.

For human GAPDH the PCR primers were:
forward primer: GAAGGTGAAGGTCGGAGTC (SEQ ID NO: 7)
reverse primer: GAAGATGGTGATGGGATTTC (SEQ ID NO: 8) and the PCR probe was: 5' JOE-CAAGCTTC-CCGTTCTCAGCC-TAMRA 3' (SEQ ID NO: 9) where JOE (PE-Applied Biosystems, Foster City, Calif.) is the fluorescent reporter dye) and TAMRA (PE-Applied Biosystems, Foster City, Calif.) is the quencher dye.

Probes and primers to mouse apolipoprotein B were designed to hybridize to a mouse apolipoprotein B sequence, using published sequence information (GenBank accession number M35186, incorporated herein as SEQ ID NO: 10). For mouse apolipoprotein B the PCR primers were:
forward primer: CGTGGGCTCCAGCATTCTA (SEQ ID NO: 11)
reverse primer: AGTCATTTCTGCCTTTGCGTC (SEQ ID NO: 12) and the PCR probe was: FAM-CCAATG-GTCGGGCACTGCTCAA-TAMRA (SEQ ID NO: 13) where FAM (PE-Applied Biosystems, Foster City, Calif.)

is the fluorescent reporter dye) and TAMRA (PE-Applied Biosystems, Foster City, Calif.) is the quencher dye.

For mouse GAPDH the PCR primers were:
forward primer: GGCAAATTCAACGGCACAGT (SEQ ID NO: 14)
reverse primer: GGGTCTCGCTCCTGGAAGAT (SEQ ID NO:15) and the PCR probe was: 5' JOE-AAGGC-CGAGAATGGGAAGCTTGTCATC-TAMRA 3' (SEQ ID NO: 16) where JOE (PE-Applied Biosystems, Foster City, Calif.) is the fluorescent reporter dye and TAMRA (PE-Applied Biosystems, Foster City, Calif.) is the quencher dye.

Example 14

Northern Blot Analysis of Apolipoprotein B mRNA Levels

Eighteen hours after antisense treatment, cell monolayers were washed twice with cold PBS and lysed in 1 mL RNA-ZOL™ (TEL-TEST "B" Inc., Friendswood, Tex.). Total RNA was prepared following manufacturer's recommended protocols. Twenty micrograms of total RNA was fractionated by electrophoresis through 1.2% agarose gels containing 1.1% formaldehyde using a MOPS buffer system (AM-RESCO, Inc. Solon, Ohio). RNA was transferred from the gel to HYBOND™-N+ nylon membranes (Amersham Pharmacia Biotech, Piscataway, N.J.) by overnight capillary transfer using a Northern/Southern Transfer buffer system (TEL-TEST "B" Inc., Friendswood, Tex.). RNA transfer was confirmed by UV visualization. Membranes were fixed by UV cross-linking using a STRATALINKER™ UV Crosslinker 2400 (Stratagene, Inc, La Jolla, Calif.) and then robed using QUICKHYB™ hybridization solution (Stratagene, La Jolla, Calif.) using manufacturer's recommendations for stringent conditions.

To detect human apolipoprotein B, a human apolipoprotein B specific probe was prepared by PCR using the forward primer TGCTAAAGGCACATATGGCCT (SEQ ID NO: 4) and the reverse primer CTCAGGTTGGACTCTCCAT-TGAG (SEQ ID NO: 5). To normalize for variations in loading and transfer efficiency membranes were stripped and probed for human glyceraldehyde-3-phosphate dehydrogenase (GAPDH) RNA (Clontech, Palo Alto, Calif.).

To detect mouse apolipoprotein B, a human apolipoprotein B specific probe was prepared by PCR using the forward primer CGTGGGCTCCAGCATTCTA (SEQ ID NO: 11) and the reverse primer AGTCATTTCTGCCTTTGCGTC (SEQ ID NO: 12). To normalize for variations in loading and transfer efficiency membranes were stripped and probed for mouse glyceraldehyde-3-phosphate dehydrogenase (GAPDH) RNA (Clontech, Palo Alto, Calif.).

Hybridized membranes were visualized and quantitated using a PHOSPHORIMAGER™ and IMAGEQUANT™ Software V3.3 (Molecular Dynamics, Sunnyvale, Calif.). Data was normalized to GAPDH levels in untreated controls.

Example 15

Antisense Inhibition of Human Apolipoprotein B Expression by Chimeric Phosphorothioate Oligonucleotides Having 2'-MOE Wings and a Deoxy Gap In accordance with the present invention, a series of oligonucleotides were designed to target different regions of the human apolipoprotein B RNA, using published sequence (GenBank accession number NM_000384, incorporated herein as SEQ ID NO: 3). The oligonucleotides are shown in Table 1. "Target site" indicates the first (5'-most) nucleotide number on the particular target sequence to which the oligonucleotide binds. All compounds in Table 1 are chimeric oligonucleotides ("gapmers") 20 nucleotides in length, composed of a central "gap" region consisting of ten 2'-deoxynucleotides, which is flanked on both sides (5' and 3' directions) by five-nucleotide "wings". The wings are composed of 2'-methoxyethyl (2'-MOE) nucleotides. The internucleoside (backbone) linkages are phosphorothioate (P=S) throughout the oligonucleotide. All cytidine residues are 5-methylcytidines. The compounds were analyzed for their effect on human apolipoprotein B mRNA levels in HepG2 cells by quantitative real-time PCR as described in other examples herein. Data are averages from two experiments. If present, "N.D." indicates "no data".

TABLE 1

Inhibition of human apolipoprotein B mRNA levels by chimeric phosphorothioate oligonucleotides having 2'-MOE wings and a deoxy gap

| ISIS # | REGION | TARGET SEQ ID NO | TARGET SITE | SEQUENCE | % INHIB | SEQ ID NO |
|---|---|---|---|---|---|---|
| 147780 | 5'UTR | 3 | 1 | CCGCAGGTCCCGGTGGGAAT | 40 | 17 |
| 147781 | 5'UTR | 3 | 21 | ACCGAGAAGGGCACTCAGCC | 35 | 18 |
| 147782 | 5'UTR | 3 | 71 | GCCTCGGCCTCGCGGCCCTG | 67 | 19 |
| 147783 | Start Codon | 3 | 114 | TCCATCGCCAGCTGCGGTGG | N.D. | 20 |
| 147784 | Coding | 3 | 151 | CAGCGCCAGCAGCGCCAGCA | 70 | 21 |
| 147785 | Coding | 3 | 181 | GCCCGCCAGCAGCAGCAGCA | 29 | 22 |
| 147786 | Coding | 3 | 321 | CTTGAATCAGCAGTCCCAGG | 34 | 23 |
| 147787 | Coding | 3 | 451 | CTTCAGCAAGGCTTTGCCCT | N.D. | 24 |
| 147788 | Coding | 3 | 716 | TTTCTGTTGCCACATTGCCC | 95 | 25 |
| 147789 | Coding | 3 | 911 | GGAAGAGGTGTTGCTCCTTG | 24 | 26 |
| 147790 | Coding | 3 | 951 | TGTGCTACCATCCCATACTT | 33 | 27 |
| 147791 | Coding | 3 | 1041 | TCAAATCCGAGGCCCATCTT | N.D. | 28 |
| 147792 | Coding | 3 | 1231 | GGACACCTCAATCAGCTGTG | 26 | 29 |
| 147793 | Coding | 3 | 1361 | TCAGGGCCACCAGGTAGGTG | N.D. | 30 |
| 147794 | Coding | 3 | 1561 | GTAATCTTCATCCCCAGTGC | 47 | 31 |
| 147795 | Coding | 3 | 1611 | TGCTCCATGGTTTGGCCCAT | N.D. | 32 |
| 147796 | Coding | 3 | 1791 | GCAGCCAGTCGCTTATCTCC | 8 | 33 |
| 147797 | Coding | 3 | 2331 | GTATAGCCPAAGTGGTCCAC | N.D. | 34 |
| 147798 | Coding | 3 | 2496 | CCCAGGAGCTGGAGGTCATG | N.D. | 35 |
| 147799 | Coding | 3 | 2573 | TTGAGCCCTTCCTGATCACC | N.D. | 36 |
| 147800 | Coding | 3 | 2811 | ATCTGGACCCCACTCCTAGC | N.D. | 37 |
| 147801 | Coding | 3 | 2842 | CAGACCCGACTCGTGGAAGA | 38 | 38 |
| 147802 | Coding | 3 | 3367 | GCCCTCAGTAGATTCATCAT | N.D. | 39 |
| 147803 | Coding | 3 | 3611 | GCCATGCCACCCTCTTGGAA | N.D. | 40 |
| 147804 | Coding | 3 | 3791 | AACCCACCTGCCGGAAAGTC | N.D. | 41 |
| 147805 | Coding | 3 | 3841 | ACTCCCAGATGCCTTCTGAA | N.D. | 42 |
| 147806 | Coding | 3 | 4281 | ATGTGGTAACGAGCCCGAAG | 100 | 43 |
| 147807 | Coding | 3 | 4391 | GGCGTAGAGACCCATCACAT | 25 | 44 |
| 147808 | Coding | 3 | 4641 | GTGTTAGGATCCCTCTGACA | N.D. | 45 |
| 147809 | Coding | 3 | 5241 | CCCAGTGATAGCTCTGTGAG | 60 | 46 |
| 147810 | Coding | 3 | 5355 | ATTTCAGCATATGAGCCCAT | 0 | 47 |
| 147811 | Coding | 3 | 5691 | CCCTGAACCTTAGCAACAGT | N.D. | 48 |
| 147812 | Coding | 3 | 5742 | GCTGAAGCCAGCCCAGCGAT | N.D. | 49 |
| 147813 | Coding | 3 | 5891 | ACAGCTGCCCAGTATGTTCT | N.D. | 50 |
| 147814 | Coding | 3 | 7087 | CCCAATAAGATTTATAACAA | 34 | 51 |
| 147815 | Coding | 3 | 7731 | TGGCCTACCAGAGACAGGTA | 45 | 52 |
| 147816 | Coding | 3 | 7841 | TCATACGTTTACCCCAATCT | 100 | 53 |
| 147817 | Coding | 3 | 7901 | GCATGGTCCCAAGGATGGTC | 0 | 54 |
| 147818 | Coding | 3 | 8491 | AGTGATGGAAGCTGCGATAC | 30 | 55 |
| 147819 | Coding | 3 | 9181 | ATGAGCATCATGCCTCCCAG | N.D. | 56 |
| 147820 | Coding | 3 | 9931 | GAACACATAGCCGAATGCCG | 100 | 57 |
| 147821 | Coding | 3 | 10263 | GTGGTGCCCTCTAATTTGTA | N.D. | 58 |
| 147822 | Coding | 3 | 10631 | CCCGAGAAAGAACCGAACCC | N.D. | 59 |
| 147823 | Coding | 3 | 10712 | TGCCCTGCAGCTTCACTGAA | 19 | 60 |
| 147824 | Coding | 3 | 11170 | GAAATCCCATAAGCTCTTGT | N.D. | 61 |
| 147825 | coding | 3 | 12301 | AGAAGCTGCCTCTTCTTCCC | 72 | 82 |
| 147826 | Coding | 3 | 12401 | TCAGGGTGACCCCTGTGTGT | 80 | 63 |
| 147827 | Coding | 3 | 12471 | CTAATGGCCCCTTGATAAAC | 13 | 64 |
| 147828 | Coding | 3 | 12621 | ACGTTATCCTTGAGTCCCTG | 12 | 65 |

TABLE 1-continued

Inhibition of human apolipoprotein B mRNA levels by chimeric phosphorothioate oligonucleotides having 2'-MOE wings and a deoxy gap

| ISIS # | REGION | TARGET SEQ ID NO | TARGET SITE | SEQUENCE | % INHIB | SEQ ID NO |
|---|---|---|---|---|---|---|
| 147829 | Coding | 3 | 12741 | TATATCCCAGGTTTCCCCGG | 64 | 66 |
| 147830 | Coding | 3 | 12801 | ACCTGGGACACTACCGTCCC | N.D. | 67 |
| 147831 | 3'UTR | 3 | 13921 | CTGCCTACTGCAAGGCTGGC | 0 | 68 |
| 147832 | 3'UTR | 3 | 13991 | AGAGACCTTCCGAGCCCTGG | N.D. | 69 |
| 147833 | 3'UTR | 3 | 14101 | ATGATACACAATAAAGACTC | 25 | 70 |

As shown in Table 1, SEQ ID NOs 17, 18, 19, 21, 23, 25, 27, 31, 38, 43, 46, 51, 52, 53, 55, 57, 62, 63 and 66 demonstrated at least 30% inhibition of human apolipoprotein B expression in this assay and are therefore preferred. The target sites to which these preferred sequences are complementary are herein referred to as "active sites" and are therefore preferred sites for targeting by compounds of the present invention. As apolipoprotein B exists in two forms in mammals (ApoB-48 and ApoB-100) which are colinear at the amino terminus, antisense oligonucleotides targeting nucleotides 1-6530 hybridize to both forms, while those targeting nucleotides 6531-14121 are specific to the long form of apolipoprotein B.

Example 16

Antisense Inhibition of Human Apolipoprotein B Expression by Chimeric Phosphorothioate Oligonucleotides Having 2'-MOE Wings and a Deoxy Gap-Dose Response Study In accordance with the present invention, a subset of the antisense oligonuclotides in Example 15 were further investigated in dose-response studies. Treatment doses were 50, 150 and 250 nM. The compounds were analyzed for their effect on human apolipoprotein B mRNA levels in HepG2 cells by quantitative real-time PCR as described in other examples herein. Data are averages from two experiments and are shown in Table 2.

TABLE 2

Inhibition of human apolipoprotein B mRNA levels by chimeric phosphorothioate oligonucleotides having 2'-MOE wings and a deoxy gap

| | Percent Inhibition | | |
|---|---|---|---|
| ISIS # | 50 nM | 150 nM | 250 nM |
| 147788 | 54 | 63 | 72 |
| 147806 | 23 | 45 | 28 |
| 147816 | 25 | 81 | 65 |
| 147820 | 10 | 0 | 73 |

Example 17

Antisense Inhibition of Mouse Apolipoprotein B Expression by Chimeric Phosphorothioate Oligonucleotides Having 2'-MOE Wings and a Deoxy Gap In accordance with the present invention, a series of oligonucleotides were designed to target different regions of the mouse apolipoprotein B RNA, using published sequence (GenBank accession number M35186, incorporated herein as SEQ ID NO: 10). The oligonucleotides are shown in Table 3. "Target site" indicates the first (5'-most) nucleotide number on the particular target sequence to which the oligonucleotide binds. All compounds in Table 3 are chimeric oligonucleotides ("gapmers") 20 nucleotides in length, composed of a central "gap" region consisting of ten 2'-deoxynucleotides, which is flanked on both sides (5' and 3' directions) by five-nucleotide "wings". The wings are composed of 2'-methoxyethyl (2'-MOE) nucleotides. The internucleoside (backbone) linkages are phosphorothioate (P=S) throughout the oligonucleotide. All cytidine residues are 5-methylcytidines. The compounds were analyzed for their effect on mouse apolipoprotein B mRNA levels in primary hepatocytes by quantitative real-time PCR as described in other examples herein. Data are averages from two experiments. If present, "N.D." indicates "no data".

TABLE 3

Inhibition of mouse apolipoprotein B mRNA levels by chimeric phosphorothioate oligonucleotides having 2'-MOE wings and a deoxy gap

| ISIS # | REGION | TARGET SEQ ID NO | TARGET SITE | SEQUENCE | % INHIB | SEQ ID NO |
|---|---|---|---|---|---|---|
| 147475 | Coding | 10 | 13 | ATTGTATGTGAGAGGTGAGG | 79 | 71 |
| 147476 | Coding | 10 | 66 | GAGGAGATTGGATCTTAAGG | 13 | 72 |
| 147477 | Coding | 10 | 171 | CTTCAAATTGGGACTCTCCT | N.D | 73 |
| 147478 | Coding | 10 | 211 | TCCAGGAATTGAGCTTGTGC | 78 | 74 |
| 147479 | Coding | 10 | 238 | TTCAGGACTGGAGGATGAGG | N.D | 75 |
| 147480 | Coding | 10 | 291 | TCTCACCCTCATGCTCCATT | 54 | 76 |
| 147481 | Coding | 10 | 421 | TGACTGTCAAGGGTGAGCTG | 24 | 77 |
| 147482 | Coding | 10 | 461 | GTCCAGCCTAGGAACACTCA | 59 | 78 |
| 147483 | Coding | 10 | 531 | ATGTCAATGCCACATGTCCA | N.D | 79 |
| 147484 | Coding | 10 | 581 | TTCATCCGAGAAGTTGGGAC | 49 | 80 |
| 147485 | Coding | 10 | 601 | ATTTGGGACGAATGTATGCC | 64 | 81 |
| 147486 | Coding | 10 | 711 | AGTTGAGGAAGCCAGATTCA | N.D | 82 |
| 147487 | Coding | 10 | 964 | TTCCCAGTCAGCTTTAGTGG | 73 | 83 |
| 147488 | Coding | 10 | 1023 | AGCTTGCTTGTTGGGCACGG | 72 | 84 |
| 147489 | Coding | 10 | 1111 | CCTATACTGGCTTCTATGTT | 5 | 85 |
| 147490 | Coding | 10 | 1191 | TGAACTCCCTCTAAGGCAAG | N.D | 86 |
| 147491 | Coding | 10 | 1216 | GAGAAATCCTTCAGTAAGGG | 71 | 87 |
| 147492 | Coding | 10 | 1323 | CAATGGAATGCTTGTCACTG | 68 | 88 |
| 147493 | Coding | 10 | 1441 | GCTTCATTATAGGAGGTGGT | 41 | 89 |
| 147494 | Coding | 10 | 1531 | ACAACTGGGATAGTGTAGCC | 84 | 90 |
| 147495 | Coding | 10 | 1631 | GTTAGGACCAGGGATTGTGA | 0 | 91 |
| 147496 | Coding | 10 | 1691 | ACCATGGAAAACTGGCAACT | 19 | 92 |
| 147497 | Coding | 10 | 1721 | TGGGAGGAAAAACTTGAATA | N.D | 93 |
| 147498 | Coding | 10 | 1861 | TGGGCAACGATATCTGATTG | 0 | 94 |
| 147499 | Coding | 10 | 1901 | CTGCAGGGCGTCAGTGACAA | 29 | 95 |
| 147500 | Coding | 10 | 1932 | GCATCAGACGTGATGTTCCC | N.D | 96 |
| 147501 | Coding | 10 | 2021 | CTTGGTTAAACTAATGGTGC | 18 | 97 |
| 147502 | Coding | 10 | 2071 | ATGGGAGCATGGAGGTTGGC | 16 | 98 |
| 147503 | Coding | 10 | 2141 | AATGCATGATGAAACAGTGG | 26 | 99 |
| 147504 | Coding | 10 | 2201 | ATCAATGCCTCCTGTTGCAG | N.D | 100 |
| 147505 | Coding | 10 | 2231 | GGAACTGAGACTTTCTAAGC | 76 | 101 |
| 147506 | Coding | 10 | 2281 | AGGAAGGAACTCTTGATATT | 58 | 102 |
| 147507 | Coding | 10 | 2321 | ATTGGCTTCATTGGCAACAC | 81 | 103 |
| 147759 | Coding | 10 | 1 | AGGTGAGGAAGTTCGAATTC | 19 | 104 |
| 147760 | Coding | 10 | 121 | TTGTTCCCTGAAGTTGTTAC | N.D | 105 |
| 147761 | Coding | 10 | 251 | GTTCATGGATTCCTTCAGGA | 45 | 106 |
| 147762 | Coding | 10 | 281 | ATGCTCCATTCTCACATGCT | 46 | 107 |
| 147763 | Coding | 10 | 338 | TGCGACTGTGTCTGATTTCC | 34 | 108 |
| 147764 | Coding | 10 | 541 | GTCCCTGAAGATGTCAATGC | 97 | 109 |
| 147765 | Coding | 10 | 561 | AGGCCCAGTTCCATGACCCT | 59 | 110 |
| 147766 | Coding | 10 | 761 | GCAGCCCACGTGCTGAGATT | 59 | 111 |
| 147767 | Coding | 10 | 801 | CGTCCTTGAGCAGTGCCCGA | 5 | 112 |
| 147768 | Coding | 10 | 1224 | CCCATATGGACAAATCCTTC | 24 | 113 |
| 147769 | Coding | 10 | 1581 | CATGCCTGGAAGCCAGTGTC | 89 | 114 |
| 147770 | Coding | 10 | 1741 | GTGTTGAATCCCTTGAAATC | 67 | 115 |
| 147771 | Coding | 10 | 1781 | GGTAAAGTTGCCCATGGCTG | 68 | 116 |
| 147772 | Coding | 10 | 1841 | GTTATAAAGTCCAGCATTGG | 78 | 117 |

TABLE 3-continued

Inhibition of mouse apolipoprotein B mRNA levels by chimeric phosphorothioate oligonucleotides having 2'-MOE wings and a deoxy gap

| ISIS # | REGION | TARGET SEQ ID NO | TARGET SITE | SEQUENCE | % INHIB | SEQ ID NO |
|---|---|---|---|---|---|---|
| 147773 | Coding | 10 | 1931 | CATCAGACGTGATGTTCCCT | 85 | 118 |
| 147774 | Coding | 10 | 1956 | TCGCTAGTTTCAATCCCCTT | 84 | 119 |
| 147775 | Coding | 10 | 2002 | CTGTCATGACTGCCCTTTAC | 52 | 120 |
| 147776 | Coding | 10 | 2091 | GCTTGAAGTTCATTGAGAAT | 92 | 121 |
| 147777 | Coding | 10 | 2291 | TTCCTCAGAAAGGAAGGAAC | N.D | 122 |
| 147778 | Coding | 10 | 2331 | TCAGATATACATTGCCTTCA | 14 | 123 |

As shown in Table 3, SEQ ID Nos 71, 74, 76, 78, 81, 83, 84, 87, 88, 90, 101, 102, 103, 109, 111, 111, 114, 115, 116, 117, 118, 119, 120 and 121 demonstrated at least 50% inhibition of mouse apolipoprotein B expression in this assay and are therefore preferred. The target sites to which these preferred sequences are complementary are herein referred to as "active sites" and are therefore preferred sites for targeting by compounds of the present invention.

Example 18

Antisense Inhibition Mouse Apolipoprotein B Expression by Chimeric Phosphorothioate Oligonucleotides Having 2'-MOE Wings and a Deoxy Gap-Dose Response Study In accordance with the present invention, a subset of the antisense oligonuclotides in Example 17 were further investigated in dose-response studies. Treatment doses were 50, 150 and 300 nM. The compounds were analyzed for their effect on mouse apolipoprotein B mRNA levels in primary hepatocytes cells by quantitative real-time PCR as described in other examples herein. Data are averages from two experiments and are shown in Table 4.

TABLE 4

Inhibition of mouse apolipoprotein B mRNA levels by chimeric phosphorothioate oligonucleotides having 2'-MOE wings and a deoxy gap

| | Percent Inhibition | | |
|---|---|---|---|
| ISIS # | 50 nM | 150 nM | 300 nM |
| 147483 | 56 | 88 | 89 |
| 147764 | 48 | 84 | 90 |
| 147769 | 3 | 14 | 28 |
| 147776 | 0 | 17 | 44 |

Example 19

Western Blot Analysis of Apolipoprotein B Protein Levels

Western blot analysis (immunoblot analysis) was carried out using standard methods. Cells were harvested 16-20 h after oligonucleotide treatment, washed once with PBS, suspended in Laemmli buffer (100 ul/well), boiled for 5 minutes and loaded on a 16% SDS-PAGE gel. Gels were run for 1.5 hours at 150 V, and transferred to membrane for western blotting. Appropriate primary antibody directed to apolipoprotein B was used, with a radiolabelled or fluorescently labeled secondary antibody directed against the primary antibody species. Bands were visualized using a PHOSPHORIMAGER™ (Molecular Dynamics, Sunnyvale Calif.).

What is claimed is:

1. An oligonucleotide 12 to 30 nucleobases in length, or a salt thereof, targeted to a nucleic acid molecule encoding apolipoprotein B, wherein the oligonucleotide is 100% complementary to SEQ ID NO: 3 and wherein the oligonucleotide comprises at least 8 consecutive nucleobases of SEQ ID NO:27.

2. The oligonucleotide of claim 1 comprising at least one modified nucleobase.

3. The oligonucleotide of claim 2 wherein the modified nucleobase is a 5-methylcytosine.

4. The oligonucleotide of claim 1 wherein the oligonucleotide is a chimeric oligonucleotide.

5. The oligonucleotide of claim 1, wherein the oligonucleotide inhibits the expression of the long form of apolipoprotein B, ApoB-100.

6. The oligonucleotide of claim 1, wherein the oligonucleotide comprises a modified sugar moiety.

7. The oligonucleotide of claim 6, wherein the modified sugar moiety is a 2' substituted sugar moiety or a bicyclic sugar moiety.

8. The oligonucleotide of claim 7, wherein the 2' substituted sugar moiety is a 2'-O-methoxyethyl sugar moiety.

9. The oligonucleotide of claim 7, wherein the bicyclic sugar moiety is a locked nucleic acid.

10. The oligonucleotide of claim 7, wherein the bicyclic sugar moiety has a $(-CH_2-)_n$ group forming a bridge between the 2' oxygen and the 4' carbon atoms of the sugar ring, wherein n is 1 or 2.

11. The oligonucleotide of claim 1, wherein the oligonucleotide comprises at least one modified internucleoside linkage.

12. The oligonucleotide of claim 11, wherein the modified internucleoside linkage is a phosphorothioate linkage.

13. The oligonucleotide of claim 1, having
  i. a gap segment of ten linked 2'-deoxynucleosides,
  ii. a 5' wing segment of five linked nucleosides, and
  iii. a 3' wing segment of five linked nucleosides,
  wherein the gap segment is positioned between the 5' wing segment and the 3' wing segment, wherein each nucleoside of each wing segment comprises a 2'-O-methoxyethyl sugar modification, and wherein each internucleoside linkage is a phosphorothioate internucleoside linkage.

14. The oligonucleotide of claim 13, the oligonucleotide comprising at least one cytosine, wherein each cytosine is a 5-methylcytosine.

15. The oligonucleotide of claim 1, wherein the oligonucleotide comprises 20 nucleobases.

16. The oligonucleotide of claim 15, wherein the oligonucleotide consists of 20 nucleobases.

17. The oligonucleotide of claim 1, wherein the oligonucleotide is an oligonucleotide salt.

18. The oligonucleotide of claim 15, wherein the salt is a sodium salt.

19. A composition comprising the oligonucleotide of claim 1 and a pharmaceutically acceptable carrier or diluent.

20. The composition of claim 19 further comprising a colloidal dispersion system.

* * * * *

SEQUENCE LISTING

<160> NUMBER OF SEQ ID NOS: 123

<210> SEQ ID NO 1
<211> LENGTH: 20
<212> TYPE: DNA
<213> ORGANISM: Artificial Sequence
<220> FEATURE:
<223> OTHER INFORMATION: Antisense Oligonucleotide

<400> SEQUENCE: 1
tccgtcatcg ctcctcaggg                                            20

<210> SEQ ID NO 2
<211> LENGTH: 20
<212> TYPE: DNA
<213> ORGANISM: Artificial Sequence
<220> FEATURE:
<223> OTHER INFORMATION: Antisense Oligonucleotide

<400> SEQUENCE: 2
atgcattctg cccccaagga                                            20

<210> SEQ ID NO 3
<211> LENGTH: 14121
<212> TYPE: DNA
<213> ORGANISM: Homo sapiens
<220> FEATURE:
<221> NAME/KEY: CDS -continued

<222> LOCATION: (129)...(13820)

<400> SEQUENCE: 3

```
attcccaccg ggacctgcgg ggctgagtgc ccttctcggt tgctgccgct gaggagcccg      60
cccagccagc cagggccgcg aggccgaggc caggccgcag cccaggagcc gccccaccgc     120 agctggcg atg gac ccg ccg agg ccc gcg ctg ctg gcg ctg ctg gcg ctg     170
         Met Asp Pro Pro Arg Pro Ala Leu Leu Ala Leu Leu Ala Leu
           1               5                  10 cct gcg ctg ctg ctg ctg ctg gcg ggc gcc agg gcc gaa gag gaa           218
Pro Ala Leu Leu Leu Leu Leu Ala Gly Ala Arg Ala Glu Glu Glu
 15                  20                  25                  30 atg ctg gaa aat gtc agc ctg gtc tgt cca aaa gat gcg acc cga ttc       266
Met Leu Glu Asn Val Ser Leu Val Cys Pro Lys Asp Ala Thr Arg Phe
                     35                  40                  45 aag cac ctc cgg aag tac aca tac aac tat gag gct gag agt tcc agt       314
Lys His Leu Arg Lys Tyr Thr Tyr Asn Tyr Glu Ala Glu Ser Ser Ser
                 50                  55                  60 gga gtc cct ggg act gct gat tca aga agt gcc acc agg atc aac tgc       362
Gly Val Pro Gly Thr Ala Asp Ser Arg Ser Ala Thr Arg Ile Asn Cys
             65                  70                  75 aag gtt gag ctg gag gtt ccc cag ctc tgc agc ttc atc ctg aag acc       410
Lys Val Glu Leu Glu Val Pro Gln Leu Cys Ser Phe Ile Leu Lys Thr
         80                  85                  90 agc cag tgc acc ctg aaa gag gtg tat ggc ttc aac cct gag ggc aaa       458
Ser Gln Cys Thr Leu Lys Glu Val Tyr Gly Phe Asn Pro Glu Gly Lys
 95                 100                 105                 110 gcc ttg ctg aag aaa acc aag aac tct gag gag ttt gct gca gcc atg       506
Ala Leu Leu Lys Lys Thr Lys Asn Ser Glu Glu Phe Ala Ala Ala Met
                 115                 120                 125 tcc agg tat gag ctc aag ctg gcc att cca gaa ggg aag cag gtt ttc       554
Ser Arg Tyr Glu Leu Lys Leu Ala Ile Pro Glu Gly Lys Gln Val Phe
             130                 135                 140 ctt tac ccg gag aaa gat gaa cct act tac atc ctg aac atc aag agg       602
Leu Tyr Pro Glu Lys Asp Glu Pro Thr Tyr Ile Leu Asn Ile Lys Arg
         145                 150                 155 ggc atc att tct gcc ctc ctg gtt ccc cca gag aca gaa gaa gcc aag       650
Gly Ile Ile Ser Ala Leu Leu Val Pro Pro Glu Thr Glu Glu Ala Lys
 160                 165                 170 caa gtg ttg ttt ctg gat acc gtg tat gga aac tgc tcc act cac ttt       698
Gln Val Leu Phe Leu Asp Thr Val Tyr Gly Asn Cys Ser Thr His Phe
175                 180                 185                 190 acc gtc aag acg agg aag ggc aat gtg gca aca gaa ata tcc act gaa       746
Thr Val Lys Thr Arg Lys Gly Asn Val Ala Thr Glu Ile Ser Thr Glu
                 195                 200                 205 aga gac ctg ggg cag tgt gat cgc ttc aag ccc atc cgc aca ggc atc       794
Arg Asp Leu Gly Gln Cys Asp Arg Phe Lys Pro Ile Arg Thr Gly Ile
             210                 215                 220 agc cca ctt gct ctc atc aaa ggc atg acc cgc ccc ttg tca act ctg       842
Ser Pro Leu Ala Leu Ile Lys Gly Met Thr Arg Pro Leu Ser Thr Leu
         225                 230                 235 atc agc agc agc cag tcc tgt cag tac aca ctg gac gct aag agg aag       890
Ile Ser Ser Ser Gln Ser Cys Gln Tyr Thr Leu Asp Ala Lys Arg Lys
 240                 245                 250 cat gtg gca gaa gcc atc tgc aag gag caa cac ctc ttc ctg cct ttc       938
His Val Ala Glu Ala Ile Cys Lys Glu Gln His Leu Phe Leu Pro Phe
255                 260                 265                 270 tcc tac aac aat aag tat ggg atg gta gca caa gtg aca cag act ttg       986
Ser Tyr Asn Asn Lys Tyr Gly Met Val Ala Gln Val Thr Gln Thr Leu
                 275                 280                 285
```

-continued

| | | |
|---|---|---|
| aaa ctt gaa gac aca cca aag atc aac agc cgc ttc ttt ggt gaa ggt<br>Lys Leu Glu Asp Thr Pro Lys Ile Asn Ser Arg Phe Phe Gly Glu Gly<br>290                                 295                          300 | 1034 |
| act aag aag atg ggc ctc gca ttt gag agc acc aaa tcc aca tca cct<br>Thr Lys Lys Met Gly Leu Ala Phe Glu Ser Thr Lys Ser Thr Ser Pro<br>      305                           310                           315 | 1082 |
| cca aag cag gcc gaa gct gtt ttg aag act ctc cag gaa ctg aaa aaa<br>Pro Lys Gln Ala Glu Ala Val Leu Lys Thr Leu Gln Glu Leu Lys Lys<br>320                                325                        330 | 1130 |
| cta acc atc tct gag caa aat atc cag aga gct aat ctc ttc aat aag<br>Leu Thr Ile Ser Glu Gln Asn Ile Gln Arg Ala Asn Leu Phe Asn Lys<br>335                          340                        345                        350 | 1178 |
| ctg gtt act gag ctg aga ggc ctc agt gat gaa gca gtc aca tct ctc<br>Leu Val Thr Glu Leu Arg Gly Leu Ser Asp Glu Ala Val Thr Ser Leu<br>                          355                        360                        365 | 1226 |
| ttg cca cag ctg att gag gtg tcc agc ccc atc act tta caa gcc ttg<br>Leu Pro Gln Leu Ile Glu Val Ser Ser Pro Ile Thr Leu Gln Ala Leu<br>                    370                        375                        380 | 1274 |
| gtt cag tgt gga cag cct cag tgc tcc act cac atc ctc cag tgg ctg<br>Val Gln Cys Gly Gln Pro Gln Cys Ser Thr His Ile Leu Gln Trp Leu<br>385                                390                        395 | 1322 |
| aaa cgt gtg cat gcc aac ccc ctt ctg ata gat gtg gtc acc tac ctg<br>Lys Arg Val His Ala Asn Pro Leu Leu Ile Asp Val Val Thr Tyr Leu<br>      400                           405                           410 | 1370 |
| gtg gcc ctg atc ccc gag ccc tca gca cag cag ctg cga gag atc ttc<br>Val Ala Leu Ile Pro Glu Pro Ser Ala Gln Gln Leu Arg Glu Ile Phe<br>415                                420                        425                        430 | 1418 |
| aac atg gcg agg gat cag cgc agc cga gcc acc ttg tat gcg ctg agc<br>Asn Met Ala Arg Asp Gln Arg Ser Arg Ala Thr Leu Tyr Ala Leu Ser<br>                            435                        440                        445 | 1466 |
| cac gcg gtc aac aac tat cat aag aca aac cct aca ggg acc cag gag<br>His Ala Val Asn Asn Tyr His Lys Thr Asn Pro Thr Gly Thr Gln Glu<br>                    450                        455                        460 | 1514 |
| ctg ctg gac att gct aat tac ctg atg gaa cag att caa gat gac tgc<br>Leu Leu Asp Ile Ala Asn Tyr Leu Met Glu Gln Ile Gln Asp Asp Cys<br>465                                470                        475 | 1562 |
| act ggg gat gaa gat tac acc tat ttg att ctg cgg gtc att gga aat<br>Thr Gly Asp Glu Asp Tyr Thr Tyr Leu Ile Leu Arg Val Ile Gly Asn<br>      480                           485                           490 | 1610 |
| atg ggc caa acc atg gag cag tta act cca gaa ctc aag tct tca atc<br>Met Gly Gln Thr Met Glu Gln Leu Thr Pro Glu Leu Lys Ser Ser Ile<br>495                                500                        505                        510 | 1658 |
| ctc aaa tgt gtc caa agt aca aag cca tca ctg atg atc cag aaa gct<br>Leu Lys Cys Val Gln Ser Thr Lys Pro Ser Leu Met Ile Gln Lys Ala<br>                    515                        520                        525 | 1706 |
| gcc atc cag gct ctg cgg aaa atg gag cct aaa gac aag gac cag gag<br>Ala Ile Gln Ala Leu Arg Lys Met Glu Pro Lys Asp Lys Asp Gln Glu<br>530                                535                        540 | 1754 |
| gtt ctt ctt cag act ttc ctt gat gat gct tct ccg gga gat aag cga<br>Val Leu Leu Gln Thr Phe Leu Asp Asp Ala Ser Pro Gly Asp Lys Arg<br>                          545                        550                        555 | 1802 |
| ctg gct gcc tat ctt atg ttg atg agg agt cct tca cag gca gat att<br>Leu Ala Ala Tyr Leu Met Leu Met Arg Ser Pro Ser Gln Ala Asp Ile<br>      560                           565                           570 | 1850 |
| aac aaa att gtc caa att cta cca tgg gaa cag aat gag caa gtg aag<br>Asn Lys Ile Val Gln Ile Leu Pro Trp Glu Gln Asn Glu Gln Val Lys<br>575                                580                        585                        590 | 1898 |
| aac ttt gtg gct tcc cat att gcc aat atc ttg aac tca gaa gaa ttg<br>Asn Phe Val Ala Ser His Ile Ala Asn Ile Leu Asn Ser Glu Glu Leu | 1946 |

-continued

|  |  |  |  | 595 |  |  |  | 600 |  |  |  | 605 |  |  |  |  |
|---|---|---|---|---|---|---|---|---|---|---|---|---|---|---|---|---|
| gat | atc | caa | gat | ctg | aaa | aag | tta | gtg | aaa | gaa | gct | ctg | aaa | gaa | tct | 1994 |
| Asp | Ile | Gln | Asp | Leu | Lys | Lys | Leu | Val | Lys | Glu | Ala | Leu | Lys | Glu | Ser |  |
|  |  |  | 610 |  |  |  | 615 |  |  |  | 620 |  |  |  |  |  |
| caa | ctt | cca | act | gtc | atg | gac | ttc | aga | aaa | ttc | tct | cgg | aac | tat | caa | 2042 |
| Gln | Leu | Pro | Thr | Val | Met | Asp | Phe | Arg | Lys | Phe | Ser | Arg | Asn | Tyr | Gln |  |
|  |  | 625 |  |  |  | 630 |  |  |  | 635 |  |  |  |  |  |  |
| ctc | tac | aaa | tct | gtt | tct | ctt | cca | tca | ctt | gac | cca | gcc | tca | gcc | aaa | 2090 |
| Leu | Tyr | Lys | Ser | Val | Ser | Leu | Pro | Ser | Leu | Asp | Pro | Ala | Ser | Ala | Lys |  |
|  | 640 |  |  |  | 645 |  |  |  | 650 |  |  |  |  |  |  |  |
| ata | gaa | ggg | aat | ctt | ata | ttt | gat | cca | aat | aac | tac | ctt | cct | aaa | gaa | 2138 |
| Ile | Glu | Gly | Asn | Leu | Ile | Phe | Asp | Pro | Asn | Asn | Tyr | Leu | Pro | Lys | Glu |  |
| 655 |  |  |  | 660 |  |  |  | 665 |  |  |  | 670 |  |  |  |  |
| agc | atg | ctg | aaa | act | acc | ctc | act | gcc | ttt | gga | ttt | gct | tca | gct | gac | 2186 |
| Ser | Met | Leu | Lys | Thr | Thr | Leu | Thr | Ala | Phe | Gly | Phe | Ala | Ser | Ala | Asp |  |
|  |  |  | 675 |  |  |  | 680 |  |  |  | 685 |  |  |  |  |  |
| ctc | atc | gag | att | ggc | ttg | gaa | gga | aaa | ggc | ttt | gag | cca | aca | ttg | gaa | 2234 |
| Leu | Ile | Glu | Ile | Gly | Leu | Glu | Gly | Lys | Gly | Phe | Glu | Pro | Thr | Leu | Glu |  |
|  |  | 690 |  |  |  | 695 |  |  |  | 700 |  |  |  |  |  |  |
| gct | ctt | ttt | ggg | aag | caa | gga | ttt | ttc | cca | gac | agt | gtc | aac | aaa | gct | 2282 |
| Ala | Leu | Phe | Gly | Lys | Gln | Gly | Phe | Phe | Pro | Asp | Ser | Val | Asn | Lys | Ala |  |
|  | 705 |  |  |  | 710 |  |  |  | 715 |  |  |  |  |  |  |  |
| ttg | tac | tgg | gtt | aat | ggt | caa | gtt | cct | gat | ggt | gtc | tct | aag | gtc | tta | 2330 |
| Leu | Tyr | Trp | Val | Asn | Gly | Gln | Val | Pro | Asp | Gly | Val | Ser | Lys | Val | Leu |  |
| 720 |  |  |  | 725 |  |  |  | 730 |  |  |  |  |  |  |  |  |
| gtg | gac | cac | ttt | ggc | tat | acc | aaa | gat | gat | aaa | cat | gag | cag | gat | atg | 2378 |
| Val | Asp | His | Phe | Gly | Tyr | Thr | Lys | Asp | Asp | Lys | His | Glu | Gln | Asp | Met |  |
| 735 |  |  |  | 740 |  |  |  | 745 |  |  |  | 750 |  |  |  |  |
| gta | aat | gga | ata | atg | ctc | agt | gtt | gag | aag | ctg | att | aaa | gat | ttg | aaa | 2426 |
| Val | Asn | Gly | Ile | Met | Leu | Ser | Val | Glu | Lys | Leu | Ile | Lys | Asp | Leu | Lys |  |
|  |  |  | 755 |  |  |  | 760 |  |  |  | 765 |  |  |  |  |  |
| tcc | aaa | gaa | gtc | ccg | gaa | gcc | aga | gcc | tac | ctc | cgc | atc | ttg | gga | gag | 2474 |
| Ser | Lys | Glu | Val | Pro | Glu | Ala | Arg | Ala | Tyr | Leu | Arg | Ile | Leu | Gly | Glu |  |
|  |  | 770 |  |  |  | 775 |  |  |  | 780 |  |  |  |  |  |  |
| gag | ctt | ggt | ttt | gcc | agt | ctc | cat | gac | ctc | cag | ctc | ctg | gga | aag | ctg | 2522 |
| Glu | Leu | Gly | Phe | Ala | Ser | Leu | His | Asp | Leu | Gln | Leu | Leu | Gly | Lys | Leu |  |
|  | 785 |  |  |  | 790 |  |  |  | 795 |  |  |  |  |  |  |  |
| ctt | ctg | atg | ggt | gcc | cgc | act | ctg | cag | ggg | atc | ccc | cag | atg | att | gga | 2570 |
| Leu | Leu | Met | Gly | Ala | Arg | Thr | Leu | Gln | Gly | Ile | Pro | Gln | Met | Ile | Gly |  |
| 800 |  |  |  | 805 |  |  |  | 810 |  |  |  |  |  |  |  |  |
| gag | gtc | atc | agg | aag | ggc | tca | aag | aat | gac | ttt | ttt | ctt | cac | tac | atc | 2618 |
| Glu | Val | Ile | Arg | Lys | Gly | Ser | Lys | Asn | Asp | Phe | Phe | Leu | His | Tyr | Ile |  |
| 815 |  |  |  | 820 |  |  |  | 825 |  |  |  | 830 |  |  |  |  |
| ttc | atg | gag | aat | gcc | ttt | gaa | ctc | ccc | act | gga | gct | gga | tta | cag | ttg | 2666 |
| Phe | Met | Glu | Asn | Ala | Phe | Glu | Leu | Pro | Thr | Gly | Ala | Gly | Leu | Gln | Leu |  |
|  |  |  | 835 |  |  |  | 840 |  |  |  | 845 |  |  |  |  |  |
| caa | ata | tct | tca | tct | gga | gtc | att | gct | ccc | gga | gcc | aag | gct | gga | gta | 2714 |
| Gln | Ile | Ser | Ser | Ser | Gly | Val | Ile | Ala | Pro | Gly | Ala | Lys | Ala | Gly | Val |  |
|  |  | 850 |  |  |  | 855 |  |  |  | 860 |  |  |  |  |  |  |
| aaa | ctg | gaa | gta | gcc | aac | atg | cag | gct | gaa | ctg | gtg | gca | aaa | ccc | tcc | 2762 |
| Lys | Leu | Glu | Val | Ala | Asn | Met | Gln | Ala | Glu | Leu | Val | Ala | Lys | Pro | Ser |  |
|  | 865 |  |  |  | 870 |  |  |  | 875 |  |  |  |  |  |  |  |
| gtg | tct | gtg | gag | ttt | gtg | aca | aat | atg | ggc | atc | atc | att | ccg | gac | ttc | 2810 |
| Val | Ser | Val | Glu | Phe | Val | Thr | Asn | Met | Gly | Ile | Ile | Ile | Pro | Asp | Phe |  |
| 880 |  |  |  | 885 |  |  |  | 890 |  |  |  |  |  |  |  |  |
| gct | agg | agt | ggg | gtc | cag | atg | aac | acc | aac | ttc | ttc | cac | gag | tcg | ggt | 2858 |
| Ala | Arg | Ser | Gly | Val | Gln | Met | Asn | Thr | Asn | Phe | Phe | His | Glu | Ser | Gly |  |
| 895 |  |  |  | 900 |  |  |  | 905 |  |  |  | 910 |  |  |  |  |
| ctg | gag | gct | cat | gtt | gcc | cta | aaa | gct | ggg | aag | ctg | aag | ttt | atc | att | 2906 |

```
Leu Glu Ala His Val Ala Leu Lys Ala Gly Lys Leu Lys Phe Ile Ile
            915                 920                 925 cct tcc cca aag aga cca gtc aag ctg ctc agt gga ggc aac aca tta       2954
Pro Ser Pro Lys Arg Pro Val Lys Leu Leu Ser Gly Gly Asn Thr Leu
            930                 935                 940 cat ttg gtc tct acc acc aaa acg gag gtg atc cca cct ctc att gag       3002
His Leu Val Ser Thr Thr Lys Thr Glu Val Ile Pro Pro Leu Ile Glu
            945                 950                 955 aac agg cag tcc tgg tca gtt tgc aag caa gtc ttt cct ggc ctg aat       3050
Asn Arg Gln Ser Trp Ser Val Cys Lys Gln Val Phe Pro Gly Leu Asn
            960                 965                 970 tac tgc acc tca ggc gct tac tcc aac gcc agc tcc aca gac tcc gcc       3098
Tyr Cys Thr Ser Gly Ala Tyr Ser Asn Ala Ser Ser Thr Asp Ser Ala
975                 980                 985                 990 tcc tac tat ccg ctg acc ggg gac acc aga tta gag ctg gaa ctg agg       3146
Ser Tyr Tyr Pro Leu Thr Gly Asp Thr Arg Leu Glu Leu Glu Leu Arg
                995                 1000                1005 cct aca gga gag att gag cag tat tct gtc agc gca acc tat gag ctc       3194
Pro Thr Gly Glu Ile Glu Gln Tyr Ser Val Ser Ala Thr Tyr Glu Leu
                1010                1015                1020 cag aga gag gac aga gcc ttg gtg gat acc ctg aag ttt gta act caa       3242
Gln Arg Glu Asp Arg Ala Leu Val Asp Thr Leu Lys Phe Val Thr Gln
                1025                1030                1035 gca gaa ggt gcg aag cag act gag gct acc atg aca ttc aaa tat aat       3290
Ala Glu Gly Ala Lys Gln Thr Glu Ala Thr Met Thr Phe Lys Tyr Asn
                1040                1045                1050 cgg cag agt atg acc ttg tcc agt gaa gtc caa att ccg gat ttt gat       3338
Arg Gln Ser Met Thr Leu Ser Ser Glu Val Gln Ile Pro Asp Phe Asp
1055                1060                1065                1070 gtt gac ctc gga aca atc ctc aga gtt aat gat gaa tct act gag ggc       3386
Val Asp Leu Gly Thr Ile Leu Arg Val Asn Asp Glu Ser Thr Glu Gly
                1075                1080                1085 aaa acg tct tac aga ctc acc ctg gac att cag aac aag aaa att act       3434
Lys Thr Ser Tyr Arg Leu Thr Leu Asp Ile Gln Asn Lys Lys Ile Thr
                1090                1095                1100 gag gtc gcc ctc atg ggc cac cta agt tgt gac aca aag gaa gaa aga       3482
Glu Val Ala Leu Met Gly His Leu Ser Cys Asp Thr Lys Glu Glu Arg
                1105                1110                1115 aaa atc aag ggt gtt att tcc ata ccc cgt ttg caa gca gaa gcc aga       3530
Lys Ile Lys Gly Val Ile Ser Ile Pro Arg Leu Gln Ala Glu Ala Arg
                1120                1125                1130 agt gag atc ctc gcc cac tgg tcg cct gcc aaa ctg ctt ctc caa atg       3578
Ser Glu Ile Leu Ala His Trp Ser Pro Ala Lys Leu Leu Leu Gln Met
1135                1140                1145                1150 gac tca tct gct aca gct tat ggc tcc aca gtt tcc aag agg gtg gca       3626
Asp Ser Ser Ala Thr Ala Tyr Gly Ser Thr Val Ser Lys Arg Val Ala
                1155                1160                1165 tgg cat tat gat gaa gag aag att gaa ttt gaa tgg aac aca ggc acc       3674
Trp His Tyr Asp Glu Glu Lys Ile Glu Phe Glu Trp Asn Thr Gly Thr
                1170                1175                1180 aat gta gat acc aaa aaa atg act tcc aat ttc cct gtg gat ctc tcc       3722
Asn Val Asp Thr Lys Lys Met Thr Ser Asn Phe Pro Val Asp Leu Ser
                1185                1190                1195 gat tat cct aag agc ttg cat atg tat gct aat aga ctc ctg gat cac       3770
Asp Tyr Pro Lys Ser Leu His Met Tyr Ala Asn Arg Leu Leu Asp His
                1200                1205                1210 aga gtc cct gaa aca gac atg act ttc cgg cac gtg ggt tcc aaa tta       3818
Arg Val Pro Glu Thr Asp Met Thr Phe Arg His Val Gly Ser Lys Leu
1215                1220                1225                1230
```

```
ata gtt gca atg agc tca tgg ctt cag aag gca tct ggg agt ctt cct        3866
Ile Val Ala Met Ser Ser Trp Leu Gln Lys Ala Ser Gly Ser Leu Pro
                1235                1240                1245 tat acc cag act ttg caa gac cac ctc aat agc ctg aag gag ttc aac        3914
Tyr Thr Gln Thr Leu Gln Asp His Leu Asn Ser Leu Lys Glu Phe Asn
            1250                1255                1260 ctc cag aac atg gga ttg cca gac ttc cac atc cca gaa aac ctc ttc        3962
Leu Gln Asn Met Gly Leu Pro Asp Phe His Ile Pro Glu Asn Leu Phe
        1265                1270                1275 tta aaa agc gat ggc cgg gtc aaa tat acc ttg aac aag aac agt ttg        4010
Leu Lys Ser Asp Gly Arg Val Lys Tyr Thr Leu Asn Lys Asn Ser Leu
    1280                1285                1290 aaa att gag att cct ttg cct ttt ggt ggc aaa tcc tcc aga gat cta        4058
Lys Ile Glu Ile Pro Leu Pro Phe Gly Gly Lys Ser Ser Arg Asp Leu
1295                1300                1305                1310 aag atg tta gag act gtt agg aca cca gcc ctc cac ttc aag tct gtg        4106
Lys Met Leu Glu Thr Val Arg Thr Pro Ala Leu His Phe Lys Ser Val
                1315                1320                1325 gga ttc cat ctg cca tct cga gag ttc caa gtc cct act ttt acc att        4154
Gly Phe His Leu Pro Ser Arg Glu Phe Gln Val Pro Thr Phe Thr Ile
            1330                1335                1340 ccc aag ttg tat caa ctg caa gtg cct ctc ctg ggt gtt cta gac ctc        4202
Pro Lys Leu Tyr Gln Leu Gln Val Pro Leu Leu Gly Val Leu Asp Leu
        1345                1350                1355 tcc acg aat gtc tac agc aac ttg tac aac tgg tcc gcc tcc tac agt        4250
Ser Thr Asn Val Tyr Ser Asn Leu Tyr Asn Trp Ser Ala Ser Tyr Ser
    1360                1365                1370 ggt ggc aac acc agc aca gac cat ttc agc ctt cgg gct cgt tac cac        4298
Gly Gly Asn Thr Ser Thr Asp His Phe Ser Leu Arg Ala Arg Tyr His
1375                1380                1385                1390 atg aag gct gac tct gtg gtt gac ctg ctt tcc tac aat gtg caa gga        4346
Met Lys Ala Asp Ser Val Val Asp Leu Leu Ser Tyr Asn Val Gln Gly
                1395                1400                1405 tct gga gaa aca aca tat gac cac aag aat acg ttc aca cta tca tgt        4394
Ser Gly Glu Thr Thr Tyr Asp His Lys Asn Thr Phe Thr Leu Ser Cys
            1410                1415                1420 gat ggg tct cta cgc cac aaa ttt cta gat tcg aat atc aaa ttc agt        4442
Asp Gly Ser Leu Arg His Lys Phe Leu Asp Ser Asn Ile Lys Phe Ser
        1425                1430                1435 cat gta gaa aaa ctt gga aac aac cca gtc tca aaa ggt tta cta ata        4490
His Val Glu Lys Leu Gly Asn Asn Pro Val Ser Lys Gly Leu Leu Ile
    1440                1445                1450 ttc gat gca tct agt tcc tgg gga cca cag atg tct gct tca gtt cat        4538
Phe Asp Ala Ser Ser Ser Trp Gly Pro Gln Met Ser Ala Ser Val His
1455                1460                1465                1470 ttg gac tcc aaa aag aaa cag cat ttg ttt gtc aaa gaa gtc aag att        4586
Leu Asp Ser Lys Lys Lys Gln His Leu Phe Val Lys Glu Val Lys Ile
                1475                1480                1485 gat ggg cag ttc aga gtc tct tcg ttc tat gct aaa ggc aca tat ggc        4634
Asp Gly Gln Phe Arg Val Ser Ser Phe Tyr Ala Lys Gly Thr Tyr Gly
            1490                1495                1500 ctg tct tgt cag agg gat cct aac act ggc cgg ctc aat gga gag tcc        4682
Leu Ser Cys Gln Arg Asp Pro Asn Thr Gly Arg Leu Asn Gly Glu Ser
        1505                1510                1515 aac ctg agg ttt aac tcc tcc tac ctc caa ggc acc aac cag ata aca        4730
Asn Leu Arg Phe Asn Ser Ser Tyr Leu Gln Gly Thr Asn Gln Ile Thr
    1520                1525                1530 gga aga tat gaa gat gga acc ctc tcc ctc acc tcc acc tct gat ctg        4778
Gly Arg Tyr Glu Asp Gly Thr Leu Ser Leu Thr Ser Thr Ser Asp Leu
1535                1540                1545                1550
```

-continued

| | |
|---|---|
| caa agt ggc atc att aaa aat act gct tcc cta aag tat gag aac tac<br>Gln Ser Gly Ile Ile Lys Asn Thr Ala Ser Leu Lys Tyr Glu Asn Tyr<br>              1555                    1560                 1565 | 4826 |
| gag ctg act tta aaa tct gac acc aat ggg aag tat aag aac ttt gcc<br>Glu Leu Thr Leu Lys Ser Asp Thr Asn Gly Lys Tyr Lys Asn Phe Ala<br>1570                  1575                  1580 | 4874 |
| act tct aac aag atg gat atg acc ttc tct aag caa aat gca ctg ctg<br>Thr Ser Asn Lys Met Asp Met Thr Phe Ser Lys Gln Asn Ala Leu Leu<br>       1585                  1590                 1595 | 4922 |
| cgt tct gaa tat cag gct gat tac gag tca ttg agg ttc ttc agc ctg<br>Arg Ser Glu Tyr Gln Ala Asp Tyr Glu Ser Leu Arg Phe Phe Ser Leu<br>1600                  1605                  1610 | 4970 |
| ctt tct gga tca cta aat tcc cat ggt ctt gag tta aat gct gac atc<br>Leu Ser Gly Ser Leu Asn Ser His Gly Leu Glu Leu Asn Ala Asp Ile<br>1615                  1620                  1625                  1630 | 5018 |
| tta ggc act gac aaa att aat agt ggt gct cac aag gcg aca cta agg<br>Leu Gly Thr Asp Lys Ile Asn Ser Gly Ala His Lys Ala Thr Leu Arg<br>              1635                  1640                  1645 | 5066 |
| att ggc caa gat gga ata tct acc agt gca acg acc aac ttg aag tgt<br>Ile Gly Gln Asp Gly Ile Ser Thr Ser Ala Thr Thr Asn Leu Lys Cys<br>                1650                  1655                1660 | 5114 |
| agt ctc ctg gtg ctg gag aat gag ctg aat gca gag ctt ggc ctc tct<br>Ser Leu Leu Val Leu Glu Asn Glu Leu Asn Ala Glu Leu Gly Leu Ser<br>       1665                  1670                 1675 | 5162 |
| ggg gca tct atg aaa tta aca aca aat ggc cgc ttc agg gaa cac aat<br>Gly Ala Ser Met Lys Leu Thr Thr Asn Gly Arg Phe Arg Glu His Asn<br>1680                  1685                  1690 | 5210 |
| gca aaa ttc agt ctg gat ggg aaa gcc gcc ctc aca gag cta tca ctg<br>Ala Lys Phe Ser Leu Asp Gly Lys Ala Ala Leu Thr Glu Leu Ser Leu<br>1695                  1700                  1705                1710 | 5258 |
| gga agt gct tat cag gcc atg att ctg ggt gtc gac agc aaa aac att<br>Gly Ser Ala Tyr Gln Ala Met Ile Leu Gly Val Asp Ser Lys Asn Ile<br>                1715                  1720                1725 | 5306 |
| ttc aac ttc aag gtc agt caa gaa gga ctt aag ctc tca aat gac atg<br>Phe Asn Phe Lys Val Ser Gln Glu Gly Leu Lys Leu Ser Asn Asp Met<br>              1730                  1735                  1740 | 5354 |
| atg ggc tca tat gct gaa atg aaa ttt gac cac aca aac agt ctg aac<br>Met Gly Ser Tyr Ala Glu Met Lys Phe Asp His Thr Asn Ser Leu Asn<br>       1745                  1750                 1755 | 5402 |
| att gca ggc tta tca ctg gac ttc tct tca aaa ctt gac aac att tac<br>Ile Ala Gly Leu Ser Leu Asp Phe Ser Ser Lys Leu Asp Asn Ile Tyr<br>1760                  1765                  1770 | 5450 |
| agc tct gac aag ttt tat aag caa act gtt aat tta cag cta cag ccc<br>Ser Ser Asp Lys Phe Tyr Lys Gln Thr Val Asn Leu Gln Leu Gln Pro<br>1775                  1780                  1785                1790 | 5498 |
| tat tct ctg gta act act tta aac agt gac ctg aaa tac aat gct ctg<br>Tyr Ser Leu Val Thr Thr Leu Asn Ser Asp Leu Lys Tyr Asn Ala Leu<br>                1795                  1800                1805 | 5546 |
| gat ctc acc aac aat ggg aaa cta cgg cta gaa ccc ctg aag ctg cat<br>Asp Leu Thr Asn Asn Gly Lys Leu Arg Leu Glu Pro Leu Lys Leu His<br>              1810                  1815                1820 | 5594 |
| gtg gct ggt aac cta aaa gga gcc tac caa aat aat gaa ata aaa cac<br>Val Ala Gly Asn Leu Lys Gly Ala Tyr Gln Asn Asn Glu Ile Lys His<br>       1825                  1830                 1835 | 5642 |
| atc tat gcc atc tct tct gct gcc tta tca gca agc tat aaa gca gac<br>Ile Tyr Ala Ile Ser Ser Ala Ala Leu Ser Ala Ser Tyr Lys Ala Asp<br>1840                  1845                  1850 | 5690 |
| act gtt gct aag gtt cag ggt gtg gag ttt agc cat cgg ctc aac aca<br>Thr Val Ala Lys Val Gln Gly Val Glu Phe Ser His Arg Leu Asn Thr | 5738 |

-continued

| | |
|---|---|
| gac atc gct ggg ctg gct tca gcc att gac atg agc aca aac tat aat<br>Asp Ile Ala Gly Leu Ala Ser Ala Ile Asp Met Ser Thr Asn Tyr Asn<br>　　　　　　　　1875　　　　　　　　　1880　　　　　　　　　1885 | 5786 |
| tca gac tca ctg cat ttc agc aat gtc ttc cgt tct gta atg gcc ccg<br>Ser Asp Ser Leu His Phe Ser Asn Val Phe Arg Ser Val Met Ala Pro<br>　　　　　1890　　　　　　　　　1895　　　　　　　　　1900 | 5834 |
| ttt acc atg acc atc gat gca cat aca aat ggc aat ggg aaa ctc gct<br>Phe Thr Met Thr Ile Asp Ala His Thr Asn Gly Asn Gly Lys Leu Ala<br>　　　　　1905　　　　　　　　　1910　　　　　　　　　1915 | 5882 |
| ctc tgg gga gaa cat act ggg cag ctg tat agc aaa ttc ctg ttg aaa<br>Leu Trp Gly Glu His Thr Gly Gln Leu Tyr Ser Lys Phe Leu Leu Lys<br>　　1920　　　　　　　　　1925　　　　　　　　　1930 | 5930 |
| gca gaa cct ctg gca ttt act ttc tct cat gat tac aaa ggc tcc aca<br>Ala Glu Pro Leu Ala Phe Thr Phe Ser His Asp Tyr Lys Gly Ser Thr<br>1935　　　　　　　　　1940　　　　　　　　　1945　　　　　　　　　1950 | 5978 |
| agt cat cat ctc gtg tct agg aaa agc atc agt gca gct ctt gaa cac<br>Ser His His Leu Val Ser Arg Lys Ser Ile Ser Ala Ala Leu Glu His<br>　　　　　　　　　1955　　　　　　　　　1960　　　　　　　　　1965 | 6026 |
| aaa gtc agt gcc ctg ctt act cca gct gag cag aca ggc acc tgg aaa<br>Lys Val Ser Ala Leu Leu Thr Pro Ala Glu Gln Thr Gly Thr Trp Lys<br>　　　　　1970　　　　　　　　　1975　　　　　　　　　1980 | 6074 |
| ctc aag acc caa ttt aac aac aat gaa tac agc cag gac ttg gat gct<br>Leu Lys Thr Gln Phe Asn Asn Asn Glu Tyr Ser Gln Asp Leu Asp Ala<br>　　　　　1985　　　　　　　　　1990　　　　　　　　　1995 | 6122 |
| tac aac act aaa gat aaa att ggc gtg gag ctt act gga cga act ctg<br>Tyr Asn Thr Lys Asp Lys Ile Gly Val Glu Leu Thr Gly Arg Thr Leu<br>　　　　　2000　　　　　　　　　2005　　　　　　　　　2010 | 6170 |
| gct gac cta act cta cta gac tcc cca att aaa gtg cca ctt tta ctc<br>Ala Asp Leu Thr Leu Leu Asp Ser Pro Ile Lys Val Pro Leu Leu Leu<br>2015　　　　　　　　　2020　　　　　　　　　2025　　　　　　　　　2030 | 6218 |
| agt gag ccc atc aat atc att gat gct tta gag atg aga gat gcc gtt<br>Ser Glu Pro Ile Asn Ile Ile Asp Ala Leu Glu Met Arg Asp Ala Val<br>　　　　　　　　　2035　　　　　　　　　2040　　　　　　　　　2045 | 6266 |
| gag aag ccc caa gaa ttt aca att gtt gct ttt gta aag tat gat aaa<br>Glu Lys Pro Gln Glu Phe Thr Ile Val Ala Phe Val Lys Tyr Asp Lys<br>　　　　　2050　　　　　　　　　2055　　　　　　　　　2060 | 6314 |
| aac caa gat gtt cac tcc att aac ctc cca ttt ttt gag acc ttg caa<br>Asn Gln Asp Val His Ser Ile Asn Leu Pro Phe Phe Glu Thr Leu Gln<br>　　　　　2065　　　　　　　　　2070　　　　　　　　　2075 | 6362 |
| gaa tat ttt gag agg aat cga caa acc att ata gtt gta gtg gaa aac<br>Glu Tyr Phe Glu Arg Asn Arg Gln Thr Ile Ile Val Val Val Glu Asn<br>　　2080　　　　　　　　　2085　　　　　　　　　2090 | 6410 |
| gta cag aga aac ctg aag cac atc aat att gat caa ttt gta aga aaa<br>Val Gln Arg Asn Leu Lys His Ile Asn Ile Asp Gln Phe Val Arg Lys<br>2095　　　　　　　　　2100　　　　　　　　　2105　　　　　　　　　2110 | 6458 |
| tac aga gca gcc ctg gga aaa ctc cca cag caa gct aat gat tat ctg<br>Tyr Arg Ala Ala Leu Gly Lys Leu Pro Gln Gln Ala Asn Asp Tyr Leu<br>　　　　　　　　　2115　　　　　　　　　2120　　　　　　　　　2125 | 6506 |
| aat tca ttc aat tgg gag aga caa gtt tca cat gcc aag gag aaa ctg<br>Asn Ser Phe Asn Trp Glu Arg Gln Val Ser His Ala Lys Glu Lys Leu<br>　　　　　2130　　　　　　　　　2135　　　　　　　　　2140 | 6554 |
| act gct ctc aca aaa aag tat aga att aca gaa aat gat ata caa att<br>Thr Ala Leu Thr Lys Lys Tyr Arg Ile Thr Glu Asn Asp Ile Gln Ile<br>　　　　　2145　　　　　　　　　2150　　　　　　　　　2155 | 6602 |
| gca tta gat gat gcc aaa atc aac ttt aat gaa aaa cta tct caa ctg<br>Ala Leu Asp Asp Ala Lys Ile Asn Phe Asn Glu Lys Leu Ser Gln Leu<br>　　2160　　　　　　　　　2165　　　　　　　　　2170 | 6650 |
| cag aca tat atg ata caa ttt gat cag tat att aaa gat agt tat gat | 6698 |

```
Gln Thr Tyr Met Ile Gln Phe Asp Gln Tyr Ile Lys Asp Ser Tyr Asp
2175                2180                2185                2190 tta cat gat ttg aaa ata gct att gct aat att att gat gaa atc att    6746
Leu His Asp Leu Lys Ile Ala Ile Ala Asn Ile Ile Asp Glu Ile Ile
            2195                2200                2205 gaa aaa tta aaa agt ctt gat gag cac tat cat atc cgt gta aat tta    6794
Glu Lys Leu Lys Ser Leu Asp Glu His Tyr His Ile Arg Val Asn Leu
        2210                2215                2220 gta aaa aca atc cat gat cta cat ttg ttt att gaa aat att gat ttt    6842
Val Lys Thr Ile His Asp Leu His Leu Phe Ile Glu Asn Ile Asp Phe
    2225                2230                2235 aac aaa agt gga agt agt act gca tcc tgg att caa aat gtg gat act    6890
Asn Lys Ser Gly Ser Ser Thr Ala Ser Trp Ile Gln Asn Val Asp Thr
2240                2245                2250 aag tac caa atc aga atc cag ata caa gaa aaa ctg cag cag ctt aag    6938
Lys Tyr Gln Ile Arg Ile Gln Ile Gln Glu Lys Leu Gln Gln Leu Lys
2255                2260                2265                2270 aga cac ata cag aat ata gac atc cag cac cta gct gga aag tta aaa    6986
Arg His Ile Gln Asn Ile Asp Ile Gln His Leu Ala Gly Lys Leu Lys
            2275                2280                2285 caa cac att gag gct att gat gtt aga gtg ctt tta gat caa ttg gga    7034
Gln His Ile Glu Ala Ile Asp Val Arg Val Leu Leu Asp Gln Leu Gly
        2290                2295                2300 act aca att tca ttt gaa aga ata aat gat gtt ctt gag cat gtc aaa    7082
Thr Thr Ile Ser Phe Glu Arg Ile Asn Asp Val Leu Glu His Val Lys
    2305                2310                2315 cac ttt gtt ata aat ctt att ggg gat ttt gaa gta gct gag aaa atc    7130
His Phe Val Ile Asn Leu Ile Gly Asp Phe Glu Val Ala Glu Lys Ile
2320                2325                2330 aat gcc ttc aga gcc aaa gtc cat gag tta atc gag agg tat gaa gta    7178
Asn Ala Phe Arg Ala Lys Val His Glu Leu Ile Glu Arg Tyr Glu Val
2335                2340                2345                2350 gac caa caa atc cag gtt tta atg gat aaa tta gta gag ttg acc cac    7226
Asp Gln Gln Ile Gln Val Leu Met Asp Lys Leu Val Glu Leu Thr His
            2355                2360                2365 caa tac aag ttg aag gag act att cag aag cta agc aat gtc cta caa    7274
Gln Tyr Lys Leu Lys Glu Thr Ile Gln Lys Leu Ser Asn Val Leu Gln
        2370                2375                2380 caa gtt aag ata aaa gat tac ttt gag aaa ttg gtt gga ttt att gat    7322
Gln Val Lys Ile Lys Asp Tyr Phe Glu Lys Leu Val Gly Phe Ile Asp
    2385                2390                2395 gat gct gtg aag aag ctt aat gaa tta tct ttt aaa aca ttc att gaa    7370
Asp Ala Val Lys Lys Leu Asn Glu Leu Ser Phe Lys Thr Phe Ile Glu
2400                2405                2410 gat gtt aac aaa ttc ctt gac atg ttg ata aag aaa tta aag tca ttt    7418
Asp Val Asn Lys Phe Leu Asp Met Leu Ile Lys Lys Leu Lys Ser Phe
2415                2420                2425                2430 gat tac cac cag ttt gta gat gaa acc aat gac aaa atc cgt gag gtg    7466
Asp Tyr His Gln Phe Val Asp Glu Thr Asn Asp Lys Ile Arg Glu Val
            2435                2440                2445 act cag aga ctc aat ggt gaa att cag gct ctg gaa cta cca caa aaa    7514
Thr Gln Arg Leu Asn Gly Glu Ile Gln Ala Leu Glu Leu Pro Gln Lys
        2450                2455                2460 gct gaa gca tta aaa ctg ttt tta gag gaa acc aag gcc aca gtt gca    7562
Ala Glu Ala Leu Lys Leu Phe Leu Glu Glu Thr Lys Ala Thr Val Ala
    2465                2470                2475 gtg tat ctg gaa agc cta cag gac acc aaa ata acc tta atc atc aat    7610
Val Tyr Leu Glu Ser Leu Gln Asp Thr Lys Ile Thr Leu Ile Ile Asn
2480                2485                2490
```

```
tgg tta cag gag gct tta agt tca gca tct ttg gct cac atg aag gcc      7658
Trp Leu Gln Glu Ala Leu Ser Ser Ala Ser Leu Ala His Met Lys Ala
2495                2500                2505                2510 aaa ttc cga gag act cta gaa gat aca cga gac cga atg tat caa atg      7706
Lys Phe Arg Glu Thr Leu Glu Asp Thr Arg Asp Arg Met Tyr Gln Met
                2515                2520                2525 gac att cag cag gaa ctt caa cga tac ctg tct ctg gta ggc cag gtt      7754
Asp Ile Gln Gln Glu Leu Gln Arg Tyr Leu Ser Leu Val Gly Gln Val
            2530                2535                2540 tat agc aca ctt gtc acc tac att tct gat tgg tgg act ctt gct gct      7802
Tyr Ser Thr Leu Val Thr Tyr Ile Ser Asp Trp Trp Thr Leu Ala Ala
        2545                2550                2555 aag aac ctt act gac ttt gca gag caa tat tct atc caa gat tgg gct      7850
Lys Asn Leu Thr Asp Phe Ala Glu Gln Tyr Ser Ile Gln Asp Trp Ala
    2560                2565                2570 aaa cgt atg aaa gca ttg gta gag caa ggg ttc act gtt cct gaa atc      7898
Lys Arg Met Lys Ala Leu Val Glu Gln Gly Phe Thr Val Pro Glu Ile
2575                2580                2585                2590 aag acc atc ctt ggg acc atg cct gcc ttt gaa gtc agt ctt cag gct      7946
Lys Thr Ile Leu Gly Thr Met Pro Ala Phe Glu Val Ser Leu Gln Ala
                2595                2600                2605 ctt cag aaa gct acc ttc cag aca cct gat ttt ata gtc ccc cta aca      7994
Leu Gln Lys Ala Thr Phe Gln Thr Pro Asp Phe Ile Val Pro Leu Thr
            2610                2615                2620 gat ttg agg att cca tca gtt cag ata aac ttc aaa gac tta aaa aat      8042
Asp Leu Arg Ile Pro Ser Val Gln Ile Asn Phe Lys Asp Leu Lys Asn
        2625                2630                2635 ata aaa atc cca tcc agg ttt tcc aca cca gaa ttt acc atc ctt aac      8090
Ile Lys Ile Pro Ser Arg Phe Ser Thr Pro Glu Phe Thr Ile Leu Asn
    2640                2645                2650 acc ttc cac att cct tcc ttt aca att gac ttt gtc gaa atg aaa gta      8138
Thr Phe His Ile Pro Ser Phe Thr Ile Asp Phe Val Glu Met Lys Val
2655                2660                2665                2670 aag atc atc aga acc att gac cag atg cag aac agt gag ctg cag tgg      8186
Lys Ile Ile Arg Thr Ile Asp Gln Met Gln Asn Ser Glu Leu Gln Trp
                2675                2680                2685 ccc gtt cca gat ata tat ctc agg gat ctg aag gtg gag gac att cct      8234
Pro Val Pro Asp Ile Tyr Leu Arg Asp Leu Lys Val Glu Asp Ile Pro
            2690                2695                2700 cta gcg aga atc acc ctg cca gac ttc cgt tta cca gaa atc gca att      8282
Leu Ala Arg Ile Thr Leu Pro Asp Phe Arg Leu Pro Glu Ile Ala Ile
        2705                2710                2715 cca gaa ttc ata atc cca act ctc aac ctt aat gat ttt caa gtt cct      8330
Pro Glu Phe Ile Ile Pro Thr Leu Asn Leu Asn Asp Phe Gln Val Pro
    2720                2725                2730 gac ctt cac ata cca gaa ttc cag ctt ccc cac atc tca cac aca att      8378
Asp Leu His Ile Pro Glu Phe Gln Leu Pro His Ile Ser His Thr Ile
2735                2740                2745                2750 gaa gta cct act ttt ggc aag cta tac agt att ctg aaa atc caa tct      8426
Glu Val Pro Thr Phe Gly Lys Leu Tyr Ser Ile Leu Lys Ile Gln Ser
                2755                2760                2765 cct ctt ttc aca tta gat gca aat gct gac ata ggg aat gga acc acc      8474
Pro Leu Phe Thr Leu Asp Ala Asn Ala Asp Ile Gly Asn Gly Thr Thr
            2770                2775                2780 tca gca aac gaa gca ggt atc gca gct tcc atc act gcc aaa gga gag      8522
Ser Ala Asn Glu Ala Gly Ile Ala Ala Ser Ile Thr Ala Lys Gly Glu
        2785                2790                2795 tcc aaa tta gaa gtt ctc aat ttt gat ttt caa gca aat gca caa ctc      8570
Ser Lys Leu Glu Val Leu Asn Phe Asp Phe Gln Ala Asn Ala Gln Leu
    2800                2805                2810
```

-continued

| | |
|---|---|
| tca aac cct aag att aat ccg ctg gct ctg aag gag tca gtg aag ttc<br>Ser Asn Pro Lys Ile Asn Pro Leu Ala Leu Lys Glu Ser Val Lys Phe<br>2815              2820                  2825              2830 | 8618 |
| tcc agc aag tac ctg aga acg gag cat ggg agt gaa atg ctg ttt ttt<br>Ser Ser Lys Tyr Leu Arg Thr Glu His Gly Ser Glu Met Leu Phe Phe<br>              2835                  2840              2845 | 8666 |
| gga aat gct att gag gga aaa tca aac aca gtg gca agt tta cac aca<br>Gly Asn Ala Ile Glu Gly Lys Ser Asn Thr Val Ala Ser Leu His Thr<br>              2850                  2855              2860 | 8714 |
| gaa aaa aat aca ctg gag ctt agt aat gga gtg att gtc aag ata aac<br>Glu Lys Asn Thr Leu Glu Leu Ser Asn Gly Val Ile Val Lys Ile Asn<br>2865              2870                  2875 | 8762 |
| aat cag ctt acc ctg gat agc aac act aaa tac ttc cac aaa ttg aac<br>Asn Gln Leu Thr Leu Asp Ser Asn Thr Lys Tyr Phe His Lys Leu Asn<br>              2880                  2885              2890 | 8810 |
| atc ccc aaa ctg gac ttc tct agt cag gct gac ctg cgc aac gag atc<br>Ile Pro Lys Leu Asp Phe Ser Ser Gln Ala Asp Leu Arg Asn Glu Ile<br>2895              2900                  2905              2910 | 8858 |
| aag aca ctg ttg aaa gct ggc cac ata gca tgg act tct tct gga aaa<br>Lys Thr Leu Leu Lys Ala Gly His Ile Ala Trp Thr Ser Ser Gly Lys<br>              2915                  2920              2925 | 8906 |
| ggg tca tgg aaa tgg gcc tgc ccc aga ttc tca gat gag gga aca cat<br>Gly Ser Trp Lys Trp Ala Cys Pro Arg Phe Ser Asp Glu Gly Thr His<br>2930              2935                  2940 | 8954 |
| gaa tca caa att agt ttc acc ata gaa gga ccc ctc act tcc ttt gga<br>Glu Ser Gln Ile Ser Phe Thr Ile Glu Gly Pro Leu Thr Ser Phe Gly<br>              2945                  2950              2955 | 9002 |
| ctg tcc aat aag atc aat agc aaa cac cta aga gta aac caa aac ttg<br>Leu Ser Asn Lys Ile Asn Ser Lys His Leu Arg Val Asn Gln Asn Leu<br>2960              2965                  2970 | 9050 |
| gtt tat gaa tct ggc tcc ctc aac ttt tct aaa ctt gaa att caa tca<br>Val Tyr Glu Ser Gly Ser Leu Asn Phe Ser Lys Leu Glu Ile Gln Ser<br>2975              2980                  2985              2990 | 9098 |
| caa gtc gat tcc cag cat gtg ggc cac agt gtt cta act gct aaa ggc<br>Gln Val Asp Ser Gln His Val Gly His Ser Val Leu Thr Ala Lys Gly<br>              2995                  3000              3005 | 9146 |
| atg gca ctg ttt gga gaa ggg aag gca gag ttt act ggg agg cat gat<br>Met Ala Leu Phe Gly Glu Gly Lys Ala Glu Phe Thr Gly Arg His Asp<br>3010              3015                  3020 | 9194 |
| gct cat tta aat gga aag gtt att gga act ttg aaa aat tct ctt ttc<br>Ala His Leu Asn Gly Lys Val Ile Gly Thr Leu Lys Asn Ser Leu Phe<br>              3025                  3030              3035 | 9242 |
| ttt tca gcc cag cca ttt gag atc acg gca tcc aca aac aat gaa ggg<br>Phe Ser Ala Gln Pro Phe Glu Ile Thr Ala Ser Thr Asn Asn Glu Gly<br>3040              3045                  3050 | 9290 |
| aat ttg aaa gtt cgt ttt cca tta agg tta aca ggg aag ata gac ttc<br>Asn Leu Lys Val Arg Phe Pro Leu Arg Leu Thr Gly Lys Ile Asp Phe<br>3055              3060                  3065              3070 | 9338 |
| ctg aat aac tat gca ctg ttt ctg agt ccc agt gcc cag caa gca agt<br>Leu Asn Asn Tyr Ala Leu Phe Leu Ser Pro Ser Ala Gln Gln Ala Ser<br>              3075                  3080              3085 | 9386 |
| tgg caa gta agt gct agg ttc aat cag tat aag tac aac caa aat ttc<br>Trp Gln Val Ser Ala Arg Phe Asn Gln Tyr Lys Tyr Asn Gln Asn Phe<br>3090              3095                  3100 | 9434 |
| tct gct gga aac aac gag aac att atg gag gcc cat gta gga ata aat<br>Ser Ala Gly Asn Asn Glu Asn Ile Met Glu Ala His Val Gly Ile Asn<br>              3105                  3110              3115 | 9482 |
| gga gaa gca aat ctg gat ttc tta aac att cct tta aca att cct gaa<br>Gly Glu Ala Asn Leu Asp Phe Leu Asn Ile Pro Leu Thr Ile Pro Glu | 9530 |

-continued

```
        3120                3125                3130
atg cgt cta cct tac aca ata atc aca act cct cca ctg aaa gat ttc       9578
Met Arg Leu Pro Tyr Thr Ile Ile Thr Thr Pro Pro Leu Lys Asp Phe
3135                3140                3145                3150 tct cta tgg gaa aaa aca ggc ttg aag gaa ttc ttg aaa acg aca aag       9626
Ser Leu Trp Glu Lys Thr Gly Leu Lys Glu Phe Leu Lys Thr Thr Lys
                3155                3160                3165 caa tca ttt gat tta agt gta aaa gct cag tat aag aaa aac aaa cac       9674
Gln Ser Phe Asp Leu Ser Val Lys Ala Gln Tyr Lys Lys Asn Lys His
    3170                3175                3180 agg cat tcc atc aca aat cct ttg gct gtg ctt tgt gag ttt atc agt       9722
Arg His Ser Ile Thr Asn Pro Leu Ala Val Leu Cys Glu Phe Ile Ser
        3185                3190                3195 cag agc atc aaa tcc ttt gac agg cat ttt gaa aaa aac aga aac aat       9770
Gln Ser Ile Lys Ser Phe Asp Arg His Phe Glu Lys Asn Arg Asn Asn
3200                3205                3210 gca tta gat ttt gtc acc aaa tcc tat aat gaa aca aaa att aag ttt       9818
Ala Leu Asp Phe Val Thr Lys Ser Tyr Asn Glu Thr Lys Ile Lys Phe
3215                3220                3225                3230 gat aag tac aaa gct gaa aaa tct cac gac gag ctc ccc agg acc ttc       9866
Asp Lys Tyr Lys Ala Glu Lys Ser His Asp Glu Leu Pro Arg Thr Phe
                3235                3240                3245 caa att cct gga tac act gtt cca gtt gtc aat gtt gaa gtg tct cca       9914
Gln Ile Pro Gly Tyr Thr Val Pro Val Val Asn Val Glu Val Ser Pro
    3250                3255                3260 ttc acc ata gag atg tcg gca ttc ggc tat gtg ttc cca aaa gca gtc       9962
Phe Thr Ile Glu Met Ser Ala Phe Gly Tyr Val Phe Pro Lys Ala Val
        3265                3270                3275 agc atg cct agt ttc tcc atc cta ggt tct gac gtc cgt gtg cct tca      10010
Ser Met Pro Ser Phe Ser Ile Leu Gly Ser Asp Val Arg Val Pro Ser
3280                3285                3290 tac aca tta atc ctg cca tca tta gag ctg cca gtc ctt cat gtc cct      10058
Tyr Thr Leu Ile Leu Pro Ser Leu Glu Leu Pro Val Leu His Val Pro
3295                3300                3305                3310 aga aat ctc aag ctt tct ctt cca cat ttc aag gaa ttg tgt acc ata      10106
Arg Asn Leu Lys Leu Ser Leu Pro His Phe Lys Glu Leu Cys Thr Ile
                3315                3320                3325 agc cat att ttt att cct gcc atg ggc aat att acc tat gat ttc tcc      10154
Ser His Ile Phe Ile Pro Ala Met Gly Asn Ile Thr Tyr Asp Phe Ser
    3330                3335                3340 ttt aaa tca agt gtc atc aca ctg aat acc aat gct gaa ctt ttt aac      10202
Phe Lys Ser Ser Val Ile Thr Leu Asn Thr Asn Ala Glu Leu Phe Asn
        3345                3350                3355 cag tca gat att gtt gct cat ctc ctt tct tca tct tca tct gtc att      10250
Gln Ser Asp Ile Val Ala His Leu Leu Ser Ser Ser Ser Val Ile
3360                3365                3370 gat gca ctg cag tac aaa tta gag ggc acc aca aga ttg aca aga aaa      10298
Asp Ala Leu Gln Tyr Lys Leu Glu Gly Thr Thr Arg Leu Thr Arg Lys
3375                3380                3385                3390 agg gga ttg aag tta gcc aca gct ctg tct ctg agc aac aaa ttt gtg      10346
Arg Gly Leu Lys Leu Ala Thr Ala Leu Ser Leu Ser Asn Lys Phe Val
                3395                3400                3405 gag ggt agt cat aac agt act gtg agc tta acc acg aaa aat atg gaa      10394
Glu Gly Ser His Asn Ser Thr Val Ser Leu Thr Thr Lys Asn Met Glu
    3410                3415                3420 gtg tca gtg gca aaa acc aca aaa gcc gaa att cca att ttg aga atg      10442
Val Ser Val Ala Lys Thr Thr Lys Ala Glu Ile Pro Ile Leu Arg Met
        3425                3430                3435 aat ttc aag caa gaa ctt aat gga aat acc aag tca aaa cct act gtc      10490
```

-continued

```
                Asn Phe Lys Gln Glu Leu Asn Gly Asn Thr Lys Ser Lys Pro Thr Val
                    3440                3445                3450 tct tcc tcc atg gaa ttt aag tat gat ttc aat tct tca atg ctg tac           10538
Ser Ser Ser Met Glu Phe Lys Tyr Asp Phe Asn Ser Ser Met Leu Tyr
3455                3460                3465                3470 tct acc gct aaa gga gca gtt gac cac aag ctt agc ttg gaa agc ctc           10586
Ser Thr Ala Lys Gly Ala Val Asp His Lys Leu Ser Leu Glu Ser Leu
            3475                3480                3485 acc tct tac ttt tcc att gag tca tct acc aaa gga gat gtc aag ggt           10634
Thr Ser Tyr Phe Ser Ile Glu Ser Ser Thr Lys Gly Asp Val Lys Gly
        3490                3495                3500 tcg gtt ctt tct cgg gaa tat tca gga act att gct agt gag gcc aac           10682
Ser Val Leu Ser Arg Glu Tyr Ser Gly Thr Ile Ala Ser Glu Ala Asn
    3505                3510                3515 act tac ttg aat tcc aag agc aca cgg tct tca gtg aag ctg cag ggc           10730
Thr Tyr Leu Asn Ser Lys Ser Thr Arg Ser Ser Val Lys Leu Gln Gly
3520                3525                3530 act tcc aaa att gat gat atc tgg aac ctt gaa gta aaa gaa aat ttt           10778
Thr Ser Lys Ile Asp Asp Ile Trp Asn Leu Glu Val Lys Glu Asn Phe
3535                3540                3545                3550 gct gga gaa gcc aca ctc caa cgc ata tat tcc ctc tgg gag cac agt           10826
Ala Gly Glu Ala Thr Leu Gln Arg Ile Tyr Ser Leu Trp Glu His Ser
            3555                3560                3565 acg aaa aac cac tta cag cta gag ggc ctc ttt ttc acc aac gga gaa           10874
Thr Lys Asn His Leu Gln Leu Glu Gly Leu Phe Phe Thr Asn Gly Glu
        3570                3575                3580 cat aca agc aaa gcc acc ctg gaa ctc tct cca tgg caa atg tca gct           10922
His Thr Ser Lys Ala Thr Leu Glu Leu Ser Pro Trp Gln Met Ser Ala
    3585                3590                3595 ctt gtt cag gtc cat gca agt cag ccc agt tcc ttc cat gat ttc cct           10970
Leu Val Gln Val His Ala Ser Gln Pro Ser Ser Phe His Asp Phe Pro
3600                3605                3610 gac ctt ggc cag gaa gtg gcc ctg aat gct aac act aag aac cag aag           11018
Asp Leu Gly Gln Glu Val Ala Leu Asn Ala Asn Thr Lys Asn Gln Lys
3615                3620                3625                3630 atc aga tgg aaa aat gaa gtc cgg att cat tct ggg tct ttc cag agc           11066
Ile Arg Trp Lys Asn Glu Val Arg Ile His Ser Gly Ser Phe Gln Ser
            3635                3640                3645 cag gtc gag ctt tcc aat gac caa gaa aag gca cac ctt gac att gca           11114
Gln Val Glu Leu Ser Asn Asp Gln Glu Lys Ala His Leu Asp Ile Ala
        3650                3655                3660 gga tcc tta gaa gga cac cta agg ttc ctc aaa aat atc atc cta cca           11162
Gly Ser Leu Glu Gly His Leu Arg Phe Leu Lys Asn Ile Ile Leu Pro
    3665                3670                3675 gtc tat gac aag agc tta tgg gat ttc cta aag ctg gat gta acc acc           11210
Val Tyr Asp Lys Ser Leu Trp Asp Phe Leu Lys Leu Asp Val Thr Thr
3680                3685                3690 agc att ggt agg aga cag cat ctt cgt gtt tca act gcc ttt gtg tac           11258
Ser Ile Gly Arg Arg Gln His Leu Arg Val Ser Thr Ala Phe Val Tyr
3695                3700                3705                3710 acc aaa aac ccc aat ggc tat tca ttc tcc atc cct gta aaa gtt ttg           11306
Thr Lys Asn Pro Asn Gly Tyr Ser Phe Ser Ile Pro Val Lys Val Leu
            3715                3720                3725 gct gat aaa ttc att act cct ggg ctg aaa cta aat gat cta aat tca           11354
Ala Asp Lys Phe Ile Thr Pro Gly Leu Lys Leu Asn Asp Leu Asn Ser
        3730                3735                3740 gtt ctt gtc atg cct acg ttc cat gtc cca ttt aca gat ctt cag gtt           11402
Val Leu Val Met Pro Thr Phe His Val Pro Phe Thr Asp Leu Gln Val
    3745                3750                3755
```

|     |     |
| --- | --- |
| cca tcg tgc aaa ctt gac ttc aga gaa ata caa atc tat aag aag ctg<br>Pro Ser Cys Lys Leu Asp Phe Arg Glu Ile Gln Ile Tyr Lys Lys Leu<br>     3760                   3765                   3770 | 11450 |
| aga act tca tca ttt gcc ctc aac cta cca aca ctc ccc gag gta aaa<br>Arg Thr Ser Ser Phe Ala Leu Asn Leu Pro Thr Leu Pro Glu Val Lys<br>3775                 3780                   3785                   3790 | 11498 |
| ttc cct gaa gtt gat gtg tta aca aaa tat tct caa cca gaa gac tcc<br>Phe Pro Glu Val Asp Val Leu Thr Lys Tyr Ser Gln Pro Glu Asp Ser<br>     3795                   3800                   3805 | 11546 |
| ttg att ccc ttt ttt gag ata acc gtg cct gaa tct cag tta act gtg<br>Leu Ile Pro Phe Phe Glu Ile Thr Val Pro Glu Ser Gln Leu Thr Val<br>         3810                   3815                   3820 | 11594 |
| tcc cag ttc acg ctt cca aaa agt gtt tca gat ggc att gct gct ttg<br>Ser Gln Phe Thr Leu Pro Lys Ser Val Ser Asp Gly Ile Ala Ala Leu<br>     3825                   3830                   3835 | 11642 |
| gat cta aat gca gta gcc aac aag atc gca gac ttt gag ttg ccc acc<br>Asp Leu Asn Ala Val Ala Asn Lys Ile Ala Asp Phe Glu Leu Pro Thr<br>3840                 3845                   3850 | 11690 |
| atc atc gtg cct gag cag acc att gag att ccc tcc att aag ttc tct<br>Ile Ile Val Pro Glu Gln Thr Ile Glu Ile Pro Ser Ile Lys Phe Ser<br>3855                 3860                   3865                   3870 | 11738 |
| gta cct gct gga att gtc att cct tcc ttt caa gca ctg act gca cgc<br>Val Pro Ala Gly Ile Val Ile Pro Ser Phe Gln Ala Leu Thr Ala Arg<br>         3875                   3880                   3885 | 11786 |
| ttt gag gta gac tct ccc gtg tat aat gcc act tgg agt gcc agt ttg<br>Phe Glu Val Asp Ser Pro Val Tyr Asn Ala Thr Trp Ser Ala Ser Leu<br>     3890                   3895                   3900 | 11834 |
| aaa aac aaa gca gat tat gtt gaa aca gtc ctg gat tcc aca tgc agc<br>Lys Asn Lys Ala Asp Tyr Val Glu Thr Val Leu Asp Ser Thr Cys Ser<br>         3905                   3910                   3915 | 11882 |
| tca acc gta cag ttc cta gaa tat gaa cta aat gtt ttg gga aca cac<br>Ser Thr Val Gln Phe Leu Glu Tyr Glu Leu Asn Val Leu Gly Thr His<br>3920                 3925                   3930 | 11930 |
| aaa atc gaa gat ggt acg tta gcc tct aag act aaa gga aca ctt gca<br>Lys Ile Glu Asp Gly Thr Leu Ala Ser Lys Thr Lys Gly Thr Leu Ala<br>3935                 3940                   3945                   3950 | 11978 |
| cac cgt gac ttc agt gca gaa tat gaa gaa gat ggc aaa ttt gaa gga<br>His Arg Asp Phe Ser Ala Glu Tyr Glu Glu Asp Gly Lys Phe Glu Gly<br>     3955                   3960                   3965 | 12026 |
| ctt cag gaa tgg gaa gga aaa gcg cac ctc aat atc aaa agc cca gcg<br>Leu Gln Glu Trp Glu Gly Lys Ala His Leu Asn Ile Lys Ser Pro Ala<br>         3970                   3975                   3980 | 12074 |
| ttc acc gat ctc cat ctg cgc tac cag aaa gac aag aaa ggc atc tcc<br>Phe Thr Asp Leu His Leu Arg Tyr Gln Lys Asp Lys Lys Gly Ile Ser<br>     3985                   3990                   3995 | 12122 |
| acc tca gca gcc tcc cca gcc gta ggc acc gtg ggc atg gat atg gat<br>Thr Ser Ala Ala Ser Pro Ala Val Gly Thr Val Gly Met Asp Met Asp<br>         4000                   4005                   4010 | 12170 |
| gaa gat gac gac ttt tct aaa tgg aac ttc tac tac agc cct cag tcc<br>Glu Asp Asp Asp Phe Ser Lys Trp Asn Phe Tyr Tyr Ser Pro Gln Ser<br>4015                 4020                   4025                   4030 | 12218 |
| tct cca gat aaa aaa ctc acc ata ttc aaa act gag ttg agg gtc cgg<br>Ser Pro Asp Lys Lys Leu Thr Ile Phe Lys Thr Glu Leu Arg Val Arg<br>         4035                   4040                   4045 | 12266 |
| gaa tct gat gag gaa act cag atc aaa gtt aat tgg gaa gaa gag gca<br>Glu Ser Asp Glu Glu Thr Gln Ile Lys Val Asn Trp Glu Glu Glu Ala<br>         4050                   4055                   4060 | 12314 |
| gct tct ggc ttg cta acc tct ctg aaa gac aac gtg ccc aag gcc aca<br>Ala Ser Gly Leu Leu Thr Ser Leu Lys Asp Asn Val Pro Lys Ala Thr<br>4065                 4070                   4075 | 12362 |

|  |  |
|---|---:|
| ggg gtc ctt tat gat tat gtc aac aag tac cac tgg gaa cac aca ggg<br>Gly Val Leu Tyr Asp Tyr Val Asn Lys Tyr His Trp Glu His Thr Gly<br>    4080                      4085                    4090 | 12410 |
| ctc acc ctg aga gaa gtg tct tca aag ctg aga aga aat ctg cag aac<br>Leu Thr Leu Arg Glu Val Ser Ser Lys Leu Arg Arg Asn Leu Gln Asn<br>4095                  4100                    4105                4110 | 12458 |
| aat gct gag tgg gtt tat caa ggg gcc att agg caa att gat gat atc<br>Asn Ala Glu Trp Val Tyr Gln Gly Ala Ile Arg Gln Ile Asp Asp Ile<br>                4115                    4120                  4125 | 12506 |
| gac gtg agg ttc cag aaa gca gcc agt ggc acc act ggg acc tac caa<br>Asp Val Arg Phe Gln Lys Ala Ala Ser Gly Thr Thr Gly Thr Tyr Gln<br>        4130                    4135                    4140 | 12554 |
| gag tgg aag gac aag gcc cag aat ctg tac cag gaa ctg ttg act cag<br>Glu Trp Lys Asp Lys Ala Gln Asn Leu Tyr Gln Glu Leu Leu Thr Gln<br>                4145                    4150                  4155 | 12602 |
| gaa ggc caa gcc agt ttc cag gga ctc aag gat aac gtg ttt gat ggc<br>Glu Gly Gln Ala Ser Phe Gln Gly Leu Lys Asp Asn Val Phe Asp Gly<br>4160                  4165                    4170 | 12650 |
| ttg gta cga gtt act caa aaa ttc cat atg aaa gtc aag cat ctg att<br>Leu Val Arg Val Thr Gln Lys Phe His Met Lys Val Lys His Leu Ile<br>4175                  4180                  4185                4190 | 12698 |
| gac tca ctc att gat ttt ctg aac ttc ccc aga ttc cag ttt ccg ggg<br>Asp Ser Leu Ile Asp Phe Leu Asn Phe Pro Arg Phe Gln Phe Pro Gly<br>                4195                    4200                  4205 | 12746 |
| aaa cct ggg ata tac act agg gag gaa ctt tgc act atg ttc ata agg<br>Lys Pro Gly Ile Tyr Thr Arg Glu Glu Leu Cys Thr Met Phe Ile Arg<br>        4210                    4215                    4220 | 12794 |
| gag gta ggg acg gta ctg tcc cag gta tat tcg aaa gtc cat aat ggt<br>Glu Val Gly Thr Val Leu Ser Gln Val Tyr Ser Lys Val His Asn Gly<br>                4225                    4230                  4235 | 12842 |
| tca gaa ata ctg ttt tcc tat ttc caa gac cta gtg att aca ctt cct<br>Ser Glu Ile Leu Phe Ser Tyr Phe Gln Asp Leu Val Ile Thr Leu Pro<br>4240                  4245                    4250 | 12890 |
| ttc gag tta agg aaa cat aaa cta ata gat gta atc tcg atg tat agg<br>Phe Glu Leu Arg Lys His Lys Leu Ile Asp Val Ile Ser Met Tyr Arg<br>4255                  4260                    4265                4270 | 12938 |
| gaa ctg ttg aaa gat tta tca aaa gaa gcc caa gag gta ttt aaa gcc<br>Glu Leu Leu Lys Asp Leu Ser Lys Glu Ala Gln Glu Val Phe Lys Ala<br>                4275                    4280                  4285 | 12986 |
| att cag tct ctc aag acc aca gag gtg cta cgt aat ctt cag gac ctt<br>Ile Gln Ser Leu Lys Thr Thr Glu Val Leu Arg Asn Leu Gln Asp Leu<br>        4290                    4295                    4300 | 13034 |
| tta caa ttc att ttc caa cta ata gaa gat aac att aaa cag ctg aaa<br>Leu Gln Phe Ile Phe Gln Leu Ile Glu Asp Asn Ile Lys Gln Leu Lys<br>                4305                    4310                  4315 | 13082 |
| gag atg aaa ttt act tat ctt att aat tat atc caa gat gag atc aac<br>Glu Met Lys Phe Thr Tyr Leu Ile Asn Tyr Ile Gln Asp Glu Ile Asn<br>4320                  4325                    4330 | 13130 |
| aca atc ttc aat gat tat atc cca tat gtt ttt aaa ttg ttg aaa gaa<br>Thr Ile Phe Asn Asp Tyr Ile Pro Tyr Val Phe Lys Leu Leu Lys Glu<br>4335                  4340                    4345                4350 | 13178 |
| aac cta tgc ctt aat ctt cat aag ttc aat gaa ttt att caa aac gag<br>Asn Leu Cys Leu Asn Leu His Lys Phe Asn Glu Phe Ile Gln Asn Glu<br>                4355                    4360                  4365 | 13226 |
| ctt cag gaa gct tct caa gag tta cag cag atc cat caa tac att atg<br>Leu Gln Glu Ala Ser Gln Glu Leu Gln Gln Ile His Gln Tyr Ile Met<br>        4370                    4375                    4380 | 13274 |
| gcc ctt cgt gaa gaa tat ttt gat cca agt ata gtt ggc tgg aca gtg<br>Ala Leu Arg Glu Glu Tyr Phe Asp Pro Ser Ile Val Gly Trp Thr Val | 13322 |

```
                4385           4390           4395
aaa tat tat gaa ctt gaa gaa aag ata gtc agt ctg atc aag aac ctg    13370
Lys Tyr Tyr Glu Leu Glu Glu Lys Ile Val Ser Leu Ile Lys Asn Leu
    4400                4405                4410 tta gtt gct ctt aag gac ttc cat tct gaa tat att gtc agt gcc tct    13418
Leu Val Ala Leu Lys Asp Phe His Ser Glu Tyr Ile Val Ser Ala Ser
4415                4420                4425                4430 aac ttt act tcc caa ctc tca agt caa gtt gag caa ttt ctg cac aga    13466
Asn Phe Thr Ser Gln Leu Ser Ser Gln Val Glu Gln Phe Leu His Arg
        4435                4440                4445 aat att cag gaa tat ctt agc atc ctt acc gat cca gat gga aaa ggg    13514
Asn Ile Gln Glu Tyr Leu Ser Ile Leu Thr Asp Pro Asp Gly Lys Gly
            4450                4455                4460 aaa gag aag att gca gag ctt tct gcc act gct cag gaa ata att aaa    13562
Lys Glu Lys Ile Ala Glu Leu Ser Ala Thr Ala Gln Glu Ile Ile Lys
        4465                4470                4475 agc cag gcc att gcg acg aag aaa ata att tct gat tac cac cag cag    13610
Ser Gln Ala Ile Ala Thr Lys Lys Ile Ile Ser Asp Tyr His Gln Gln
    4480                4485                4490 ttt aga tat aaa ctg caa gat ttt tca gac caa ctc tct gat tac tat    13658
Phe Arg Tyr Lys Leu Gln Asp Phe Ser Asp Gln Leu Ser Asp Tyr Tyr
4495                4500                4505                4510 gaa aaa ttt att gct gaa tcc aaa aga ttg att gac ctg tcc att caa    13706
Glu Lys Phe Ile Ala Glu Ser Lys Arg Leu Ile Asp Leu Ser Ile Gln
        4515                4520                4525 aac tac cac aca ttt ctg ata tac atc acg gag tta ctg aaa aag ctg    13754
Asn Tyr His Thr Phe Leu Ile Tyr Ile Thr Glu Leu Leu Lys Lys Leu
            4530                4535                4540 caa tca acc aca gtc atg aac ccc tac atg aag ctt gct cca gga gaa    13802
Gln Ser Thr Thr Val Met Asn Pro Tyr Met Lys Leu Ala Pro Gly Glu
        4545                4550                4555 ctt act atc atc ctc taa ttttttaaaa gaaatcttca tttattcttc           13850
Leu Thr Ile Ile Leu
    4560 ttttccaatt gaactttcac atagcacaga aaaaattcaa actgcctata ttgataaaac  13910 catacagtga gccagccttg cagtaggcag tagactataa gcagaagcac atatgaactg  13970 gacctgcacc aaagctggca ccagggctcg gaaggtctct gaactcagaa ggatggcatt  14030 ttttgcaagt taaagaaaat caggatctga gttattttgc taaacttggg ggaggaggaa  14090 caaataaatg gagtctttat tgtgtatcat a                                 14121

<210> SEQ ID NO 4
<211> LENGTH: 21
<212> TYPE: DNA
<213> ORGANISM: Artificial Sequence
<220> FEATURE:
<223> OTHER INFORMATION: PCR Primer

<400> SEQUENCE: 4
tgctaaaggc acatatggcc t                                            21

<210> SEQ ID NO 5
<211> LENGTH: 23
<212> TYPE: DNA
<213> ORGANISM: Artificial Sequence
<220> FEATURE:
<223> OTHER INFORMATION: PCR Primer

<400> SEQUENCE: 5
ctcaggttgg actctccatt gag                                          23
```

<210> SEQ ID NO 6
<211> LENGTH: 28
<212> TYPE: DNA
<213> ORGANISM: Artificial Sequence
<220> FEATURE:
<223> OTHER INFORMATION: PCR Probe

<400> SEQUENCE: 6
cttgtcagag ggatcctaac actggccg                                          28

<210> SEQ ID NO 7
<211> LENGTH: 19
<212> TYPE: DNA
<213> ORGANISM: Artificial Sequence
<220> FEATURE:
<223> OTHER INFORMATION: PCR Primer

<400> SEQUENCE: 7
gaaggtgaag gtcggagtc                                                    19

<210> SEQ ID NO 8
<211> LENGTH: 20
<212> TYPE: DNA
<213> ORGANISM: Artificial Sequence
<220> FEATURE:
<223> OTHER INFORMATION: PCR Primer

<400> SEQUENCE: 8
gaagatggtg atgggatttc                                                   20

<210> SEQ ID NO 9
<211> LENGTH: 20
<212> TYPE: DNA
<213> ORGANISM: Artificial Sequence
<220> FEATURE:
<223> OTHER INFORMATION: PCR Probe

<400> SEQUENCE: 9
caagcttccc gttctcagcc                                                   20

<210> SEQ ID NO 10
<211> LENGTH: 2354
<212> TYPE: DNA
<213> ORGANISM: Mus musculus

<400> SEQUENCE: 10
gaattccaac ttcctcacct ctcacataca attgaaatac ctgcttttgg caaactgcat        60
agcatcctta agatccaatc tcctctcttt atattagatg ctaatgccaa catacagaat       120
gtaacaactt cagggaacaa agcagagatt gtggcttctg tcactgctaa aggagagtcc       180
caatttgaag ctctcaattt tgattttcaa gcacaagctc aattcctgga gttaaatcct       240
catcctccag tcctgaagga atccatgaac ttctccagta agcatgtgag aatggagcat       300
gagggtgaga tagtatttga tggaaaggcc attgagggga atcagacac  agtcgcaagt       360 ttacacacag agaaaaatga agtagagttt aataatggta tgactgtcaa agtaaacaat       420
cagctcaccc ttgacagtca cacaaagtac ttccacaagt tgagtgttcc taggctggac       480
ttctccagta aggcttctct taataatgaa atcaagacac tattagaagc tggacatgtg       540
gcattgacat cttcagggac agggtcatgg aactgggcct gtcccaactt ctcggatgaa       600
ggcatacatt cgtcccaaat tagctttact gtggatggtc ccattgcttt tgttggacta       660

-continued

```
tccaataaca taaatggcaa acacttacgg gtcatccaaa aactgactta tgaatctggc    720
ttcctcaact attctaagtt tgaagttgag tcaaaagttg aatctcagca cgtgggctcc    780
agcattctaa cagccaatgg tcgggcactg ctcaaggacg caaaggcaga atgactggt    840 gagcacaatg ccaacttaaa tggaaaagtt attggaactt tgaaaaattc tctcttcttt    900
tcagcacaac catttgagat tactgcatcc acaaataatg aaggaaattt gaaagtgggt    960
tttccactaa agctgactgg gaaaatagac ttcctgaata actatgcatt gtttctgagt   1020
ccccgtgccc aacaagcaag ctggcaagcg agtaccagat tcaatcagta caaatacaat   1080
caaaactttt ctgctataaa caatgaacac aacatagaag ccagtatagg aatgaatgga   1140
gatgccaacc tggatttctt aaacatacct ttaacaattc ctgaaattaa cttgccttac   1200
acggagttca aaactcccTT actgaaggat ttctccatat gggaagaaac aggcttgaaa   1260
gaatttttga agacaacaaa gcaatcattt gatttgagtg taaaggctca atataaaaag   1320
aacagtgaca agcattccat tgttgtccct ctgggtatgt tttatgaatt tattctcaac   1380
aatgtcaatt cgtgggacag aaaatttgag aaagtcagaa acaatgcttt acattttctt   1440
accacctcct ataatgaagc aaaaattaag gttgataagt acaaaactga aaattcccTT   1500
aatcagccct ctgggacctt tcaaaatcat ggctacacta tcccagttgt caacattgaa   1560
gtatctccat tgctgtagta gacactggct tccaggcatg tgatccccac agcaataagc   1620
accccaagtg tcacaatccc tggtcctaac atcatggtgc cttcatacaa gttagtgctg   1680
ccaccccTGG agttgccagt tttccatggt cctgggaatc tattcaagtt tttcctccca   1740
gatttcaagg gattcaacac tattgacaat atttatattc cagccatggg caactttacc   1800
tatgactTTT ctTTTaaatc aagtgtcatc acactgaata ccaatgctgg actttataac   1860
caatcagata tcgttgccca tttcctttct tcctcttcat ttgtcactga cgccctgcag   1920
tacaaattag agggaacatc acgtctgatg cgaaaaaggg gattgaaact agccacagct   1980
gtctctctaa ctaacaaatt tgtaaagggc agtcatgaca gcaccattag tttaaccaag   2040
aaaaacatgg aagcatcagt gagaacaact gccaacctcc atgctcccat attctcaatg   2100
aacttcaagc aggaacttaa tggaaatacc aagtcaaaac ccactgtttc atcatccatt   2160
gaactaaact atgacttcaa ttcctcaaag ctgcactcta ctgcaacagg aggcattgat   2220
cacaagttca gcttagaaag tctcacttcc tactttTCca ttgagtcatt caccaaagga   2280
aatatcaaga gttccttcct ttctcaggaa tattcaggaa gtgttgccaa tgaagccaat   2340
gtatatctga attc                                                     2354
```

```
<210> SEQ ID NO 11
<211> LENGTH: 19
<212> TYPE: DNA
<213> ORGANISM: Artificial Sequence
<220> FEATURE:
<223> OTHER INFORMATION: PCR Primer

<400> SEQUENCE: 11
cgtgggctcc agcattcta                                                  19

<210> SEQ ID NO 12
<211> LENGTH: 21
<212> TYPE: DNA
<213> ORGANISM: Artificial Sequence
<220> FEATURE:
<223> OTHER INFORMATION: PCR Primer

<400> SEQUENCE: 12
```
agtcatttct gcctttgcgt c					21

<210> SEQ ID NO 13
<211> LENGTH: 22
<212> TYPE: DNA
<213> ORGANISM: Artificial Sequence
<220> FEATURE:
<223> OTHER INFORMATION: PCR Probe

<400> SEQUENCE: 13
ccaatggtcg ggcactgctc aa					22

<210> SEQ ID NO 14
<211> LENGTH: 20
<212> TYPE: DNA
<213> ORGANISM: Artificial Sequence
<220> FEATURE:
<223> OTHER INFORMATION: PCR Primer

<400> SEQUENCE: 14
ggcaaattca acggcacagt					20

<210> SEQ ID NO 15
<211> LENGTH: 20
<212> TYPE: DNA
<213> ORGANISM: Artificial Sequence
<220> FEATURE:
<223> OTHER INFORMATION: PCR Primer

<400> SEQUENCE: 15
gggtctcgct cctggaagat					20

<210> SEQ ID NO 16
<211> LENGTH: 27
<212> TYPE: DNA
<213> ORGANISM: Artificial Sequence
<220> FEATURE:
<223> OTHER INFORMATION: PCR Probe

<400> SEQUENCE: 16
aaggccgaga atgggaagct tgtcatc					27

<210> SEQ ID NO 17
<211> LENGTH: 20
<212> TYPE: DNA
<213> ORGANISM: Artificial Sequence
<220> FEATURE:
<223> OTHER INFORMATION: Antisense Oligonucleotide

<400> SEQUENCE: 17
ccgcaggtcc cggtgggaat					20

<210> SEQ ID NO 18
<211> LENGTH: 20
<212> TYPE: DNA
<213> ORGANISM: Artificial Sequence
<220> FEATURE:
<223> OTHER INFORMATION: Antisense Oligonucleotide

<400> SEQUENCE: 18
accgagaagg gcactcagcc					20

<210> SEQ ID NO 19
<211> LENGTH: 20
<212> TYPE: DNA

<213> ORGANISM: Artificial Sequence
<220> FEATURE:
<223> OTHER INFORMATION: Antisense Oligonucleotide

<400> SEQUENCE: 19
gcctcggcct cgcggccctg     20

<210> SEQ ID NO 20
<211> LENGTH: 20
<212> TYPE: DNA
<213> ORGANISM: Artificial Sequence
<220> FEATURE:
<223> OTHER INFORMATION: Antisense Oligonucleotide

<400> SEQUENCE: 20
tccatcgcca gctgcggtgg     20

<210> SEQ ID NO 21
<211> LENGTH: 20
<212> TYPE: DNA
<213> ORGANISM: Artificial Sequence
<220> FEATURE:
<223> OTHER INFORMATION: Antisense Oligonucleotide

<400> SEQUENCE: 21
cagcgccagc agcgccagca     20

<210> SEQ ID NO 22
<211> LENGTH: 20
<212> TYPE: DNA
<213> ORGANISM: Artificial Sequence
<220> FEATURE:
<223> OTHER INFORMATION: Antisense Oligonucleotide

<400> SEQUENCE: 22
gcccgccagc agcagcagca     20

<210> SEQ ID NO 23
<211> LENGTH: 20
<212> TYPE: DNA
<213> ORGANISM: Artificial Sequence
<220> FEATURE:
<223> OTHER INFORMATION: Antisense Oligonucleotide

<400> SEQUENCE: 23
cttgaatcag cagtcccagg     20

<210> SEQ ID NO 24
<211> LENGTH: 20
<212> TYPE: DNA
<213> ORGANISM: Artificial Sequence
<220> FEATURE:
<223> OTHER INFORMATION: Antisense Oligonucleotide

<400> SEQUENCE: 24
cttcagcaag gctttgccct     20

<210> SEQ ID NO 25
<211> LENGTH: 20
<212> TYPE: DNA
<213> ORGANISM: Artificial Sequence
<220> FEATURE:
<223> OTHER INFORMATION: Antisense Oligonucleotide

<400> SEQUENCE: 25
tttctgttgc cacattgccc     20

```
<210> SEQ ID NO 26
<211> LENGTH: 20
<212> TYPE: DNA
<213> ORGANISM: Artificial Sequence
<220> FEATURE:
<223> OTHER INFORMATION: Antisense Oligonucleotide

<400> SEQUENCE: 26
ggaagaggtg ttgctccttg                                                   20

<210> SEQ ID NO 27
<211> LENGTH: 20
<212> TYPE: DNA
<213> ORGANISM: Artificial Sequence
<220> FEATURE:
<223> OTHER INFORMATION: Antisense Oligonucleotide

<400> SEQUENCE: 27
tgtgctacca tcccatactt                                                   20

<210> SEQ ID NO 28
<211> LENGTH: 20
<212> TYPE: DNA
<213> ORGANISM: Artificial Sequence
<220> FEATURE:
<223> OTHER INFORMATION: Antisense Oligonucleotide

<400> SEQUENCE: 28
tcaaatgcga ggcccatctt                                                   20

<210> SEQ ID NO 29
<211> LENGTH: 20
<212> TYPE: DNA
<213> ORGANISM: Artificial Sequence
<220> FEATURE:
<223> OTHER INFORMATION: Antisense Oligonucleotide

<400> SEQUENCE: 29
ggacacctca atcagctgtg                                                   20

<210> SEQ ID NO 30
<211> LENGTH: 20
<212> TYPE: DNA
<213> ORGANISM: Artificial Sequence
<220> FEATURE:
<223> OTHER INFORMATION: Antisense Oligonucleotide

<400> SEQUENCE: 30
tcagggccac caggtaggtg                                                   20

<210> SEQ ID NO 31
<211> LENGTH: 20
<212> TYPE: DNA
<213> ORGANISM: Artificial Sequence
<220> FEATURE:
<223> OTHER INFORMATION: Antisense Oligonucleotide

<400> SEQUENCE: 31
gtaatcttca tccccagtgc                                                   20

<210> SEQ ID NO 32
<211> LENGTH: 20
<212> TYPE: DNA
<213> ORGANISM: Artificial Sequence
<220> FEATURE:
```

<223> OTHER INFORMATION: Antisense Oligonucleotide

<400> SEQUENCE: 32
tgctccatgg tttggcccat                                              20

<210> SEQ ID NO 33
<211> LENGTH: 20
<212> TYPE: DNA
<213> ORGANISM: Artificial Sequence
<220> FEATURE:
<223> OTHER INFORMATION: Antisense Oligonucleotide

<400> SEQUENCE: 33
gcagccagtc gcttatctcc                                              20

<210> SEQ ID NO 34
<211> LENGTH: 20
<212> TYPE: DNA
<213> ORGANISM: Artificial Sequence
<220> FEATURE:
<223> OTHER INFORMATION: Antisense Oligonucleotide

<400> SEQUENCE: 34
gtatagccaa agtggtccac                                              20

<210> SEQ ID NO 35
<211> LENGTH: 20
<212> TYPE: DNA
<213> ORGANISM: Artificial Sequence
<220> FEATURE:
<223> OTHER INFORMATION: Antisense Oligonucleotide

<400> SEQUENCE: 35
cccaggagct ggaggtcatg                                              20

<210> SEQ ID NO 36
<211> LENGTH: 20
<212> TYPE: DNA
<213> ORGANISM: Artificial Sequence
<220> FEATURE:
<223> OTHER INFORMATION: Antisense Oligonucleotide

<400> SEQUENCE: 36 ttgagcccctt cctgatgacc                                             20

<210> SEQ ID NO 37
<211> LENGTH: 20
<212> TYPE: DNA
<213> ORGANISM: Artificial Sequence
<220> FEATURE:
<223> OTHER INFORMATION: Antisense Oligonucleotide

<400> SEQUENCE: 37
atctggaccc cactcctagc                                              20

<210> SEQ ID NO 38
<211> LENGTH: 20
<212> TYPE: DNA
<213> ORGANISM: Artificial Sequence
<220> FEATURE:
<223> OTHER INFORMATION: Antisense Oligonucleotide

<400> SEQUENCE: 38
cagacccgac tcgtggaaga                                              20

<210> SEQ ID NO 39
<211> LENGTH: 20
<212> TYPE: DNA
<213> ORGANISM: Artificial Sequence
<220> FEATURE:
<223> OTHER INFORMATION: Antisense Oligonucleotide

<400> SEQUENCE: 39
gccctcagta gattcatcat                                               20

<210> SEQ ID NO 40
<211> LENGTH: 20
<212> TYPE: DNA
<213> ORGANISM: Artificial Sequence
<220> FEATURE:
<223> OTHER INFORMATION: Antisense Oligonucleotide

<400> SEQUENCE: 40
gccatgccac cctcttggaa                                               20

<210> SEQ ID NO 41
<211> LENGTH: 20
<212> TYPE: DNA
<213> ORGANISM: Artificial Sequence
<220> FEATURE:
<223> OTHER INFORMATION: Antisense Oligonucleotide

<400> SEQUENCE: 41
aacccacgtg ccggaaagtc                                               20

<210> SEQ ID NO 42
<211> LENGTH: 20
<212> TYPE: DNA
<213> ORGANISM: Artificial Sequence
<220> FEATURE:
<223> OTHER INFORMATION: Antisense Oligonucleotide

<400> SEQUENCE: 42
actcccagat gccttctgaa                                               20

<210> SEQ ID NO 43
<211> LENGTH: 20
<212> TYPE: DNA
<213> ORGANISM: Artificial Sequence
<220> FEATURE:
<223> OTHER INFORMATION: Antisense Oligonucleotide

<400> SEQUENCE: 43
atgtggtaac gagcccgaag                                               20

<210> SEQ ID NO 44
<211> LENGTH: 20
<212> TYPE: DNA
<213> ORGANISM: Artificial Sequence
<220> FEATURE:
<223> OTHER INFORMATION: Antisense Oligonucleotide

<400> SEQUENCE: 44
ggcgtagaga cccatcacat                                               20

<210> SEQ ID NO 45
<211> LENGTH: 20
<212> TYPE: DNA
<213> ORGANISM: Artificial Sequence
<220> FEATURE:
<223> OTHER INFORMATION: Antisense Oligonucleotide

```
<400> SEQUENCE: 45
gtgttaggat ccctctgaca                                               20

<210> SEQ ID NO 46
<211> LENGTH: 20
<212> TYPE: DNA
<213> ORGANISM: Artificial Sequence
<220> FEATURE:
<223> OTHER INFORMATION: Antisense Oligonucleotide

<400> SEQUENCE: 46
cccagtgata gctctgtgag                                               20

<210> SEQ ID NO 47
<211> LENGTH: 20
<212> TYPE: DNA
<213> ORGANISM: Artificial Sequence
<220> FEATURE:
<223> OTHER INFORMATION: Antisense Oligonucleotide

<400> SEQUENCE: 47
atttcagcat atgagcccat                                               20

<210> SEQ ID NO 48
<211> LENGTH: 20
<212> TYPE: DNA
<213> ORGANISM: Artificial Sequence
<220> FEATURE:
<223> OTHER INFORMATION: Antisense Oligonucleotide

<400> SEQUENCE: 48
ccctgaacct tagcaacagt                                               20

<210> SEQ ID NO 49
<211> LENGTH: 20
<212> TYPE: DNA
<213> ORGANISM: Artificial Sequence
<220> FEATURE:
<223> OTHER INFORMATION: Antisense Oligonucleotide

<400> SEQUENCE: 49
gctgaagcca gcccagcgat                                               20

<210> SEQ ID NO 50
<211> LENGTH: 20
<212> TYPE: DNA
<213> ORGANISM: Artificial Sequence
<220> FEATURE:
<223> OTHER INFORMATION: Antisense Oligonucleotide

<400> SEQUENCE: 50
acagctgccc agtatgttct                                               20

<210> SEQ ID NO 51
<211> LENGTH: 20
<212> TYPE: DNA
<213> ORGANISM: Artificial Sequence
<220> FEATURE:
<223> OTHER INFORMATION: Antisense Oligonucleotide

<400> SEQUENCE: 51
cccaataaga tttataacaa                                               20

<210> SEQ ID NO 52
<211> LENGTH: 20
```

```
<212> TYPE: DNA
<213> ORGANISM: Artificial Sequence
<220> FEATURE:
<223> OTHER INFORMATION: Antisense Oligonucleotide

<400> SEQUENCE: 52
tggcctacca gagacaggta                                                    20

<210> SEQ ID NO 53
<211> LENGTH: 20
<212> TYPE: DNA
<213> ORGANISM: Artificial Sequence
<220> FEATURE:
<223> OTHER INFORMATION: Antisense Oligonucleotide

<400> SEQUENCE: 53
tcatacgttt agcccaatct                                                    20

<210> SEQ ID NO 54
<211> LENGTH: 20
<212> TYPE: DNA
<213> ORGANISM: Artificial Sequence
<220> FEATURE:
<223> OTHER INFORMATION: Antisense Oligonucleotide

<400> SEQUENCE: 54
gcatggtccc aaggatggtc                                                    20

<210> SEQ ID NO 55
<211> LENGTH: 20
<212> TYPE: DNA
<213> ORGANISM: Artificial Sequence
<220> FEATURE:
<223> OTHER INFORMATION: Antisense Oligonucleotide

<400> SEQUENCE: 55
agtgatggaa gctgcgatac                                                    20

<210> SEQ ID NO 56
<211> LENGTH: 20
<212> TYPE: DNA
<213> ORGANISM: Artificial Sequence
<220> FEATURE:
<223> OTHER INFORMATION: Antisense Oligonucleotide

<400> SEQUENCE: 56
atgagcatca tgcctcccag                                                    20

<210> SEQ ID NO 57
<211> LENGTH: 20
<212> TYPE: DNA
<213> ORGANISM: Artificial Sequence
<220> FEATURE:
<223> OTHER INFORMATION: Antisense Oligonucleotide

<400> SEQUENCE: 57
gaacacatag ccgaatgccg                                                    20

<210> SEQ ID NO 58
<211> LENGTH: 20
<212> TYPE: DNA
<213> ORGANISM: Artificial Sequence
<220> FEATURE:
<223> OTHER INFORMATION: Antisense Oligonucleotide

<400> SEQUENCE: 58
```

```
gtggtgccct ctaatttgta                                              20

<210> SEQ ID NO 59
<211> LENGTH: 20
<212> TYPE: DNA
<213> ORGANISM: Artificial Sequence
<220> FEATURE:
<223> OTHER INFORMATION: Antisense Oligonucleotide

<400> SEQUENCE: 59
cccgagaaag aaccgaaccc                                              20

<210> SEQ ID NO 60
<211> LENGTH: 20
<212> TYPE: DNA
<213> ORGANISM: Artificial Sequence
<220> FEATURE:
<223> OTHER INFORMATION: Antisense Oligonucleotide

<400> SEQUENCE: 60
tgccctgcag cttcactgaa                                              20

<210> SEQ ID NO 61
<211> LENGTH: 20
<212> TYPE: DNA
<213> ORGANISM: Artificial Sequence
<220> FEATURE:
<223> OTHER INFORMATION: Antisense Oligonucleotide

<400> SEQUENCE: 61
gaaatcccat aagctcttgt                                              20

<210> SEQ ID NO 62
<211> LENGTH: 20
<212> TYPE: DNA
<213> ORGANISM: Artificial Sequence
<220> FEATURE:
<223> OTHER INFORMATION: Antisense Oligonucleotide

<400> SEQUENCE: 62
agaagctgcc tcttcttccc                                              20

<210> SEQ ID NO 63
<211> LENGTH: 20
<212> TYPE: DNA
<213> ORGANISM: Artificial Sequence
<220> FEATURE:
<223> OTHER INFORMATION: Antisense Oligonucleotide

<400> SEQUENCE: 63
tcagggtgag ccctgtgtgt                                              20

<210> SEQ ID NO 64
<211> LENGTH: 20
<212> TYPE: DNA
<213> ORGANISM: Artificial Sequence
<220> FEATURE:
<223> OTHER INFORMATION: Antisense Oligonucleotide

<400> SEQUENCE: 64
ctaatggccc cttgataaac                                              20

<210> SEQ ID NO 65
<211> LENGTH: 20
<212> TYPE: DNA
<213> ORGANISM: Artificial Sequence
```

```
<220> FEATURE:
<223> OTHER INFORMATION: Antisense Oligonucleotide

<400> SEQUENCE: 65
acgttatcct tgagtccctg                                              20

<210> SEQ ID NO 66
<211> LENGTH: 20
<212> TYPE: DNA
<213> ORGANISM: Artificial Sequence
<220> FEATURE:
<223> OTHER INFORMATION: Antisense Oligonucleotide

<400> SEQUENCE: 66
tatatcccag gtttccccgg                                              20

<210> SEQ ID NO 67
<211> LENGTH: 20
<212> TYPE: DNA
<213> ORGANISM: Artificial Sequence
<220> FEATURE:
<223> OTHER INFORMATION: Antisense Oligonucleotide

<400> SEQUENCE: 67
acctgggaca gtaccgtccc                                              20

<210> SEQ ID NO 68
<211> LENGTH: 20
<212> TYPE: DNA
<213> ORGANISM: Artificial Sequence
<220> FEATURE:
<223> OTHER INFORMATION: Antisense Oligonucleotide

<400> SEQUENCE: 68
ctgcctactg caaggctggc                                              20

<210> SEQ ID NO 69
<211> LENGTH: 20
<212> TYPE: DNA
<213> ORGANISM: Artificial Sequence
<220> FEATURE:
<223> OTHER INFORMATION: Antisense Oligonucleotide

<400> SEQUENCE: 69
agagaccttc cgagccctgg                                              20

<210> SEQ ID NO 70
<211> LENGTH: 20
<212> TYPE: DNA
<213> ORGANISM: Artificial Sequence
<220> FEATURE:
<223> OTHER INFORMATION: Antisense Oligonucleotide

<400> SEQUENCE: 70
atgatacaca ataaagactc                                              20

<210> SEQ ID NO 71
<211> LENGTH: 20
<212> TYPE: DNA
<213> ORGANISM: Artificial Sequence
<220> FEATURE:
<223> OTHER INFORMATION: Antisense Oligonucleotide

<400> SEQUENCE: 71
attgtatgtg agaggtgagg                                              20
```

<210> SEQ ID NO 72
<211> LENGTH: 20
<212> TYPE: DNA
<213> ORGANISM: Artificial Sequence
<220> FEATURE:
<223> OTHER INFORMATION: Antisense Oligonucleotide

<400> SEQUENCE: 72
gaggagattg gatcttaagg                                               20

<210> SEQ ID NO 73
<211> LENGTH: 20
<212> TYPE: DNA
<213> ORGANISM: Artificial Sequence
<220> FEATURE:
<223> OTHER INFORMATION: Antisense Oligonucleotide

<400> SEQUENCE: 73
cttcaaattg ggactctcct                                               20

<210> SEQ ID NO 74
<211> LENGTH: 20
<212> TYPE: DNA
<213> ORGANISM: Artificial Sequence
<220> FEATURE:
<223> OTHER INFORMATION: Antisense Oligonucleotide

<400> SEQUENCE: 74
tccaggaatt gagcttgtgc                                               20

<210> SEQ ID NO 75
<211> LENGTH: 20
<212> TYPE: DNA
<213> ORGANISM: Artificial Sequence
<220> FEATURE:
<223> OTHER INFORMATION: Antisense Oligonucleotide

<400> SEQUENCE: 75
ttcaggactg gaggatgagg                                               20

<210> SEQ ID NO 76
<211> LENGTH: 20
<212> TYPE: DNA
<213> ORGANISM: Artificial Sequence
<220> FEATURE:
<223> OTHER INFORMATION: Antisense Oligonucleotide

<400> SEQUENCE: 76
tctcaccctc atgctccatt                                               20

<210> SEQ ID NO 77
<211> LENGTH: 20
<212> TYPE: DNA
<213> ORGANISM: Artificial Sequence
<220> FEATURE:
<223> OTHER INFORMATION: Antisense Oligonucleotide

<400> SEQUENCE: 77
tgactgtcaa gggtgagctg                                               20

<210> SEQ ID NO 78
<211> LENGTH: 20
<212> TYPE: DNA
<213> ORGANISM: Artificial Sequence
<220> FEATURE:
<223> OTHER INFORMATION: Antisense Oligonucleotide

<400> SEQUENCE: 78
gtccagccta ggaacactca        20

<210> SEQ ID NO 79
<211> LENGTH: 20
<212> TYPE: DNA
<213> ORGANISM: Artificial Sequence
<220> FEATURE:
<223> OTHER INFORMATION: Antisense Oligonucleotide

<400> SEQUENCE: 79
atgtcaatgc cacatgtcca        20

<210> SEQ ID NO 80
<211> LENGTH: 20
<212> TYPE: DNA
<213> ORGANISM: Artificial Sequence
<220> FEATURE:
<223> OTHER INFORMATION: Antisense Oligonucleotide

<400> SEQUENCE: 80
ttcatccgag aagtttgggac        20

<210> SEQ ID NO 81
<211> LENGTH: 20
<212> TYPE: DNA
<213> ORGANISM: Artificial Sequence
<220> FEATURE:
<223> OTHER INFORMATION: Antisense Oligonucleotide

<400> SEQUENCE: 81
atttgggacg aatgtatgcc        20

<210> SEQ ID NO 82
<211> LENGTH: 20
<212> TYPE: DNA
<213> ORGANISM: Artificial Sequence
<220> FEATURE:
<223> OTHER INFORMATION: Antisense Oligonucleotide

<400> SEQUENCE: 82
agttgaggaa gccagattca        20

<210> SEQ ID NO 83
<211> LENGTH: 20
<212> TYPE: DNA
<213> ORGANISM: Artificial Sequence
<220> FEATURE:
<223> OTHER INFORMATION: Antisense Oligonucleotide

<400> SEQUENCE: 83
ttcccagtca gctttagtgg        20

<210> SEQ ID NO 84
<211> LENGTH: 20
<212> TYPE: DNA
<213> ORGANISM: Artificial Sequence
<220> FEATURE:
<223> OTHER INFORMATION: Antisense Oligonucleotide

<400> SEQUENCE: 84
agcttgcttg ttgggcacgg        20

<210> SEQ ID NO 85

-continued

```
<211> LENGTH: 20
<212> TYPE: DNA
<213> ORGANISM: Artificial Sequence
<220> FEATURE:
<223> OTHER INFORMATION: Antisense Oligonucleotide

<400> SEQUENCE: 85
cctatactgg cttctatgtt                                                 20

<210> SEQ ID NO 86
<211> LENGTH: 20
<212> TYPE: DNA
<213> ORGANISM: Artificial Sequence
<220> FEATURE:
<223> OTHER INFORMATION: Antisense Oligonucleotide

<400> SEQUENCE: 86
tgaactccgt gtaaggcaag                                                 20

<210> SEQ ID NO 87
<211> LENGTH: 20
<212> TYPE: DNA
<213> ORGANISM: Artificial Sequence
<220> FEATURE:
<223> OTHER INFORMATION: Antisense Oligonucleotide

<400> SEQUENCE: 87
gagaaatcct tcagtaaggg                                                 20

<210> SEQ ID NO 88
<211> LENGTH: 20
<212> TYPE: DNA
<213> ORGANISM: Artificial Sequence
<220> FEATURE:
<223> OTHER INFORMATION: Antisense Oligonucleotide

<400> SEQUENCE: 88
caatggaatg cttgtcactg                                                 20

<210> SEQ ID NO 89
<211> LENGTH: 20
<212> TYPE: DNA
<213> ORGANISM: Artificial Sequence
<220> FEATURE:
<223> OTHER INFORMATION: Antisense Oligonucleotide

<400> SEQUENCE: 89
gcttcattat aggaggtggt                                                 20

<210> SEQ ID NO 90
<211> LENGTH: 20
<212> TYPE: DNA
<213> ORGANISM: Artificial Sequence
<220> FEATURE:
<223> OTHER INFORMATION: Antisense Oligonucleotide

<400> SEQUENCE: 90
acaactggga tagtgtagcc                                                 20

<210> SEQ ID NO 91
<211> LENGTH: 20
<212> TYPE: DNA
<213> ORGANISM: Artificial Sequence
<220> FEATURE:
<223> OTHER INFORMATION: Antisense Oligonucleotide

<400> SEQUENCE: 91
```

```
gttaggacca gggattgtga                                              20

<210> SEQ ID NO 92
<211> LENGTH: 20
<212> TYPE: DNA
<213> ORGANISM: Artificial Sequence
<220> FEATURE:
<223> OTHER INFORMATION: Antisense Oligonucleotide

<400> SEQUENCE: 92
accatggaaa actggcaact                                              20

<210> SEQ ID NO 93
<211> LENGTH: 20
<212> TYPE: DNA
<213> ORGANISM: Artificial Sequence
<220> FEATURE:
<223> OTHER INFORMATION: Antisense Oligonucleotide

<400> SEQUENCE: 93
tgggaggaaa aacttgaata                                              20

<210> SEQ ID NO 94
<211> LENGTH: 20
<212> TYPE: DNA
<213> ORGANISM: Artificial Sequence
<220> FEATURE:
<223> OTHER INFORMATION: Antisense Oligonucleotide

<400> SEQUENCE: 94
tgggcaacga tatctgattg                                              20

<210> SEQ ID NO 95
<211> LENGTH: 20
<212> TYPE: DNA
<213> ORGANISM: Artificial Sequence
<220> FEATURE:
<223> OTHER INFORMATION: Antisense Oligonucleotide

<400> SEQUENCE: 95
ctgcagggcg tcagtgacaa                                              20

<210> SEQ ID NO 96
<211> LENGTH: 20
<212> TYPE: DNA
<213> ORGANISM: Artificial Sequence
<220> FEATURE:
<223> OTHER INFORMATION: Antisense Oligonucleotide

<400> SEQUENCE: 96
gcatcagacg tgatgttccc                                              20

<210> SEQ ID NO 97
<211> LENGTH: 20
<212> TYPE: DNA
<213> ORGANISM: Artificial Sequence
<220> FEATURE:
<223> OTHER INFORMATION: Antisense Oligonucleotide

<400> SEQUENCE: 97
cttggttaaa ctaatggtgc                                              20

<210> SEQ ID NO 98
<211> LENGTH: 20
<212> TYPE: DNA
```

```
<213> ORGANISM: Artificial Sequence
<220> FEATURE:
<223> OTHER INFORMATION: Antisense Oligonucleotide

<400> SEQUENCE: 98
atgggagcat ggaggttggc                                               20

<210> SEQ ID NO 99
<211> LENGTH: 20
<212> TYPE: DNA
<213> ORGANISM: Artificial Sequence
<220> FEATURE:
<223> OTHER INFORMATION: Antisense Oligonucleotide

<400> SEQUENCE: 99
aatggatgat gaaacagtgg                                               20

<210> SEQ ID NO 100
<211> LENGTH: 20
<212> TYPE: DNA
<213> ORGANISM: Artificial Sequence
<220> FEATURE:
<223> OTHER INFORMATION: Antisense Oligonucleotide

<400> SEQUENCE: 100
atcaatgcct cctgttgcag                                               20

<210> SEQ ID NO 101
<211> LENGTH: 20
<212> TYPE: DNA
<213> ORGANISM: Artificial Sequence
<220> FEATURE:
<223> OTHER INFORMATION: Antisense Oligonucleotide

<400> SEQUENCE: 101
ggaagtgaga ctttctaagc                                               20

<210> SEQ ID NO 102
<211> LENGTH: 20
<212> TYPE: DNA
<213> ORGANISM: Artificial Sequence
<220> FEATURE:
<223> OTHER INFORMATION: Antisense Oligonucleotide

<400> SEQUENCE: 102
aggaaggaac tcttgatatt                                               20

<210> SEQ ID NO 103
<211> LENGTH: 20
<212> TYPE: DNA
<213> ORGANISM: Artificial Sequence
<220> FEATURE:
<223> OTHER INFORMATION: Antisense Oligonucleotide

<400> SEQUENCE: 103
attggcttca ttggcaacac                                               20

<210> SEQ ID NO 104
<211> LENGTH: 20
<212> TYPE: DNA
<213> ORGANISM: Artificial Sequence
<220> FEATURE:
<223> OTHER INFORMATION: Antisense Oligonucleotide

<400> SEQUENCE: 104
aggtgaggaa gttggaattc                                               20
```

```
<210> SEQ ID NO 105
<211> LENGTH: 20
<212> TYPE: DNA
<213> ORGANISM: Artificial Sequence
<220> FEATURE:
<223> OTHER INFORMATION: Antisense Oligonucleotide

<400> SEQUENCE: 105
ttgttccctg aagttgttac                                              20

<210> SEQ ID NO 106
<211> LENGTH: 20
<212> TYPE: DNA
<213> ORGANISM: Artificial Sequence
<220> FEATURE:
<223> OTHER INFORMATION: Antisense Oligonucleotide

<400> SEQUENCE: 106
gttcatggat tccttcagga                                              20

<210> SEQ ID NO 107
<211> LENGTH: 20
<212> TYPE: DNA
<213> ORGANISM: Artificial Sequence
<220> FEATURE:
<223> OTHER INFORMATION: Antisense Oligonucleotide

<400> SEQUENCE: 107
atgctccatt ctcacatgct                                              20

<210> SEQ ID NO 108
<211> LENGTH: 20
<212> TYPE: DNA
<213> ORGANISM: Artificial Sequence
<220> FEATURE:
<223> OTHER INFORMATION: Antisense Oligonucleotide

<400> SEQUENCE: 108
tgcgactgtg tctgatttcc                                              20

<210> SEQ ID NO 109
<211> LENGTH: 20
<212> TYPE: DNA
<213> ORGANISM: Artificial Sequence
<220> FEATURE:
<223> OTHER INFORMATION: Antisense Oligonucleotide

<400> SEQUENCE: 109
gtccctgaag atgtcaatgc                                              20

<210> SEQ ID NO 110
<211> LENGTH: 20
<212> TYPE: DNA
<213> ORGANISM: Artificial Sequence
<220> FEATURE:
<223> OTHER INFORMATION: Antisense Oligonucleotide

<400> SEQUENCE: 110
aggcccagtt ccatgaccct                                              20

<210> SEQ ID NO 111
<211> LENGTH: 20
<212> TYPE: DNA
<213> ORGANISM: Artificial Sequence
<220> FEATURE:
```

<223> OTHER INFORMATION: Antisense Oligonucleotide

<400> SEQUENCE: 111
ggagcccacg tgctgagatt                                           20

<210> SEQ ID NO 112
<211> LENGTH: 20
<212> TYPE: DNA
<213> ORGANISM: Artificial Sequence
<220> FEATURE:
<223> OTHER INFORMATION: Antisense Oligonucleotide

<400> SEQUENCE: 112
cgtccttgag cagtgcccga                                           20

<210> SEQ ID NO 113
<211> LENGTH: 20
<212> TYPE: DNA
<213> ORGANISM: Artificial Sequence
<220> FEATURE:
<223> OTHER INFORMATION: Antisense Oligonucleotide

<400> SEQUENCE: 113
cccatatgga gaaatccttc                                           20

<210> SEQ ID NO 114
<211> LENGTH: 20
<212> TYPE: DNA
<213> ORGANISM: Artificial Sequence
<220> FEATURE:
<223> OTHER INFORMATION: Antisense Oligonucleotide

<400> SEQUENCE: 114
catgcctgga agccagtgtc                                           20

<210> SEQ ID NO 115
<211> LENGTH: 20
<212> TYPE: DNA
<213> ORGANISM: Artificial Sequence
<220> FEATURE:
<223> OTHER INFORMATION: Antisense Oligonucleotide

<400> SEQUENCE: 115
gtgttgaatc ccttgaaatc                                           20

<210> SEQ ID NO 116
<211> LENGTH: 20
<212> TYPE: DNA
<213> ORGANISM: Artificial Sequence
<220> FEATURE:
<223> OTHER INFORMATION: Antisense Oligonucleotide

<400> SEQUENCE: 116
ggtaaagttg cccatggctg                                           20

<210> SEQ ID NO 117
<211> LENGTH: 20
<212> TYPE: DNA
<213> ORGANISM: Artificial Sequence
<220> FEATURE:
<223> OTHER INFORMATION: Antisense Oligonucleotide

<400> SEQUENCE: 117
gttataaagt ccagcattgg                                           20

```
<210> SEQ ID NO 118
<211> LENGTH: 20
<212> TYPE: DNA
<213> ORGANISM: Artificial Sequence
<220> FEATURE:
<223> OTHER INFORMATION: Antisense Oligonucleotide

<400> SEQUENCE: 118
catcagacgt gatgttccct                                                    20

<210> SEQ ID NO 119
<211> LENGTH: 20
<212> TYPE: DNA
<213> ORGANISM: Artificial Sequence
<220> FEATURE:
<223> OTHER INFORMATION: Antisense Oligonucleotide

<400> SEQUENCE: 119
tggctagttt caatccccott                                                   20

<210> SEQ ID NO 120
<211> LENGTH: 20
<212> TYPE: DNA
<213> ORGANISM: Artificial Sequence
<220> FEATURE:
<223> OTHER INFORMATION: Antisense Oligonucleotide

<400> SEQUENCE: 120
ctgtcatgac tgccctttac                                                    20

<210> SEQ ID NO 121
<211> LENGTH: 20
<212> TYPE: DNA
<213> ORGANISM: Artificial Sequence
<220> FEATURE:
<223> OTHER INFORMATION: Antisense Oligonucleotide

<400> SEQUENCE: 121
gcttgaagtt cattgagaat                                                    20

<210> SEQ ID NO 122
<211> LENGTH: 20
<212> TYPE: DNA
<213> ORGANISM: Artificial Sequence
<220> FEATURE:
<223> OTHER INFORMATION: Antisense Oligonucleotide

<400> SEQUENCE: 122
ttcctgagaa aggaaggaac                                                    20

<210> SEQ ID NO 123
<211> LENGTH: 20
<212> TYPE: DNA
<213> ORGANISM: Artificial Sequence
<220> FEATURE:
<223> OTHER INFORMATION: Antisense Oligonucleotide

<400> SEQUENCE: 123
tcagatatac attggcttca                                                    20
```